United States Patent
Henninger et al.

(10) Patent No.: US 6,825,172 B2
(45) Date of Patent: Nov. 30, 2004

(54) 3-DESCLADINOSYL-6-O-CARBAMOYL AND 6-O-CARBONOYL MACROLIDE ANTIBACTERIAL AGENTS

(75) Inventors: Todd C. Henninger, High Bridge, NJ (US); Mark J. Macielag, Branchburg, NJ (US); Brett A. Marinelli, Hamilton, NJ (US); Bin Zhu, Hillsborough, NJ (US)

(73) Assignee: Janssen Pharmaceutica, NV, Beerse (BE)

( * ) Notice: Subject to any disclaimer, the term of this patent is extended or adjusted under 35 U.S.C. 154(b) by 0 days.

(21) Appl. No.: 10/447,058

(22) Filed: May 28, 2003

(65) Prior Publication Data

US 2004/0018994 A1 Jan. 29, 2004

Related U.S. Application Data

(60) Provisional application No. 60/384,483, filed on May 31, 2002.

(51) Int. Cl.⁷ .......................... A61K 31/70; C07H 17/08
(52) U.S. Cl. ............................ 514/29; 536/7.3; 536/7.4
(58) Field of Search ...................... 536/7.3, 7.4; 514/29

(56) References Cited

U.S. PATENT DOCUMENTS

| | | | |
|---|---|---|---|
| 4,826,820 A | 5/1989 | Brain | |
| 5,444,051 A | 8/1995 | Agouridas et al. | |
| 5,561,118 A | 10/1996 | Agouridas et al. | |
| 5,770,579 A | 6/1998 | Agouridas et al. | |
| 5,866,549 A | 2/1999 | Or et al. | |
| 6,169,168 B1 | 1/2001 | Asaka et al. | |
| 6,420,535 B1 * | 7/2002 | Phan et al. | 536/7.2 |
| 6,472,372 B1 * | 10/2002 | Henninger et al. | 514/29 |
| 6,498,146 B1 * | 12/2002 | Wu | 514/29 |

FOREIGN PATENT DOCUMENTS

| | | |
|---|---|---|
| EP | 0216169 A2 | 4/1987 |
| EP | 1146051 A2 | 10/2001 |
| WO | WO 98/09978 A1 | 3/1998 |
| WO | WO 98/23628 | 6/1998 |
| WO | WO 99/11651 A2 | 3/1999 |
| WO | WO 99/21869 A1 | 5/1999 |
| WO | WO 99/21870 A1 | 5/1999 |
| WO | WO 99/35157 A1 | 7/1999 |
| WO | WO 00/12522 A1 | 3/2000 |
| WO | WO 00/62783 A2 | 10/2000 |
| WO | WO 00/63224 A2 | 10/2000 |
| WO | WO 00/63225 A2 | 10/2000 |
| WO | WO 00/66566 A1 | 11/2000 |
| WO | WO 00/75156 A1 | 12/2000 |
| WO | WO 01/10878 | 2/2001 |
| WO | WO 01/10880 | 2/2001 |
| WO | WO 02/12260 A1 | 2/2002 |
| WO | WO 02/26753 | 4/2002 |

OTHER PUBLICATIONS

Daubresse, N. et al.: Phase Transfer Wittig Reaction with 1,3–Dioxolan–2yl–methyltriphenyl phosphonium Salts: an Efficient Method for Vinylogation of Aromatic Aldehydes; Tewtrahedron 54 (1998), pp. 10761–10770.

Hauske, J.R. et al.: Synthesis of 10,11–Anhydroerythromycia; J. Org. Chem. 1982, 47, pp. 1595–1596.

Tanaka, A. et al.: Inhibitors of Acyl–CoA: Cholesterol O–Acyltransferase. 2. Identification and Structure—Activity Relationships of a Novel Series of N–Alkyl–N–(heteroaryl–substituted benzyl)–N'–arylureas1; J. Med. Chem. 1998, 41, pp. 2390–2410.

Asaka, K. et al.: Structure Activity Studies Leading Potent Acylides. 39ᵗʰ Intersicience Confernce on Antimicrobial Agent and Chemotherapy, Sep. 26–29, 1999.

* cited by examiner

*Primary Examiner*—Elli Peselev
(74) *Attorney, Agent, or Firm*—James Harrington

(57) ABSTRACT

3-Descladinosyl-6-O-carbamoyl and 6-O-carbonoyl macrolide antibacterial agents of the formula:

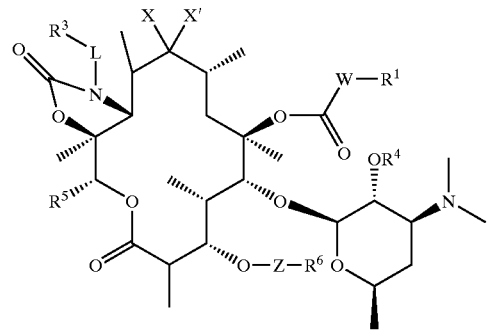

wherein $R^1$, W, $R^3$, $R^4$, $R^5$, $R^6$, X, X', and Z are as described herein and in which the substituents have the meaning indicated in the description. These compounds are useful as antibacterial agents.

22 Claims, No Drawings

3-DESCLADINOSYL-6-O-CARBAMOYL AND 6-O-CARBONOYL MACROLIDE ANTIBACTERIAL AGENTS

RELATED APPLICATIONS

This application claims the benefit under 35 U.S.C. § 119(e) of provisional application Ser. No. 60/384,483, filed on May 31, 2002 which is incorporated herein by reference in its entirety.

FIELD OF THE INVENTION

The present invention relates to the field of macrolide compounds having antibacterial activity, pharmaceutical compositions containing the compounds, and methods of treating bacterial infections with the compounds.

BACKGROUND OF THE INVENTION

Erythromycins are well-known antibacterial agents widely used to treat and prevent bacterial infection caused by Gram-positive and Gram-negative bacteria. However, due to their low stability in acidic environment, they often carry side effects such as poor and erratic oral absorption. As with other antibacterial agents, bacterial strains having resistance or insufficient susceptibility to erythromycin have developed over time and are identified in patients suffering from such ailments as community-acquired pneumonia, upper and lower respiratory tract infections, skin and soft tissue infections, meningitis, hospital-acquired lung infections, and bone and joint infections. Particularly problematic pathogens include methicillin-resistant *Staphylococcus aureus* (MRSA), vancomycin-resistant enterococci (VRE) and penicillin- and macrolide-resistant *Streptococcus pneumoniae*. Therefore, continuing efforts are called for to identify new erythromycin derivative compounds with improved antibacterial activity, and/or unanticipated selectivity against various target microorganisms, particularly erythromycin-resistant strains.

The following references relate to various erythromycin derivatives disclosed as having antibacterial activity:

EP 216,169 and U.S. Pat. No. 4,826,820 to Brain et al. disclose antibacterially active 6-carbamate erythromycin derivatives stated to "have antibacterial properties, in particular against Gram-positive bacteria but also against some Gram-negative bacteria."

U.S. Pat. No. 5,444,051, U.S. Pat. No. 5,561,118, and U.S. Pat. No. 5,770,579, all to Agouridas et al., disclose erythromycin compounds such as those of the formulae

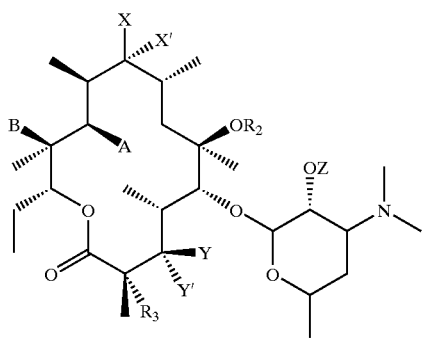

wherein substituents are as described in the respective references, which are all stated to be useful as antibiotics.

U.S. Pat. No. 5,866,549 to Or et al. and WO 98/09978 (Or et al.) disclose 6-O-substituted ketolides stated to have increased acid stability relative to erythromycin A and 6-O-methyl erythromycin A and enhanced activity toward gram negative bacteria and macrolide resistant gram positive bacteria.

U.S. Pat. No. 6,169,168 to Asaka et al. discloses erythromycin A derivatives stated to "have a strong antibacterial activity not only against sensitive bacteria but also resistant bacteria."

WO 98/23628 (Asaka et al.) discloses erythromycin A derivatives stated to have "a potent antibacterial activity against not only conventional erythromycin-sensitive bacteria but also erythromycin-resistant bacteria."

WO 99/11651 (Or et al.) discloses 3-descladinose 6-O-substituded erythromycin derivatives for treating bacterial infections.

WO 99/21869 and WO 99/21870 (both to Asaka et al.) discloses erythromycin A derivatives stated to have "a strong antibacterial activity against not only erythromycin-sensitive bacteria but also erythromycin-resistant bacteria."

WO 00/12522 (Randolph et al.) discloses 3'-N-desmethyl-3'-N-substituted-6-O-methyl-11,12-cyclic carbamate erythrolide A derivatives as antagonists of luteinizing hormone-releasing hormone.

WO 00/75156 (Phan et al.) discloses 6-O-carbamate ketolide compounds stated to be useful for treatment and prevention of infections in a mammal.

EP 1146051 (Kaneko et al.) discloses erythromycin A and ketolide derivatives useful for the treatment of a bacterial or protozoal infection in a mammal.

WO 02/12260 (Chen et al.) discloses 3-O-acyl macrolide antibioitic derivatives useful for the treatment of a bacterial or protozoal infection in a mammal.

WO 01/10878 (Asaka et al.) discloses erythromycin derivatives stated to be "characterized by an acyl group introduced at the 3-position, a cyclic carbamate structure fused at the 11- and 12-positions, and a five-membered heterocycle on the 11-position substituent, one of the nitrogen atoms of which is bonded to the 11-position nitrogen atom through an alkyl group."

WO 01/10880 (Asaka et al.) discloses erythromycin derivatives stated to be "characterized by an acyl group introduced at the 3-position, a cyclic carbamate structure fused at the 11- and 12-positions, and a fused ring composed of a five-membered nitrogenous heterocycle and a five- or six-membered ring, one of the nitrogen atoms of which is bonded to the carbamate nitrogen atom through a C2–C6 alkyl group."

WO 02/26753 (Kato et al.) discloses erythromycin A derivatives as antimicrobial agents.

Asaka et al. discloses 3-O-acyl-5-O-desosaminylerythronolide-11,12-carbamates stated to show antibacterial activities (Structure-Activity Studies Leading to Potent Acylides: 3-O-Acyl-5-O-desosaminylerythronolide-11,12-carbamates. In: 39th Interscience Conference on Antimicrobial Agents and Chemotherapy. San Francisco, Calif. (1999):2159).

SUMMARY OF THE INVENTION

The invention provides compounds of Formula 1:

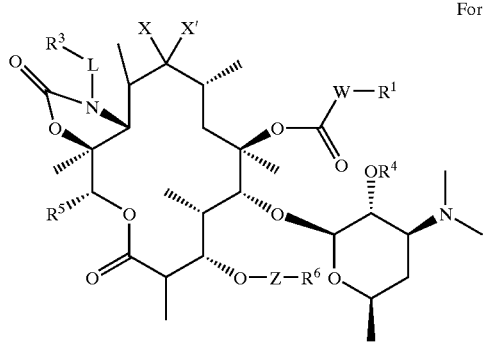

Formula 1 wherein
- $R^1$ is selected from hydrogen, optionally substituted $C_1$–$C_8$-alkyl, optionally substituted $C_2$–$C_8$-alkenyl, and optionally substituted $C_2$–$C_8$-alkynyl, wherein the substituents are independently selected from halogen, alkyl, alkenyl, alkynyl, cycloalkyl, oxo, aryl, heteroaryl, heterocyclo, CN, nitro, —$COOR_a$, —$OCOR_a$, —$OR_a$, —$SR_a$, —$SOR_a$, —$SO_2R_a$, —$NR_aR_b$, —$CONR_aR_b$, —$OCONR_aR_b$, —$NHCOR_a$, —$NHCOOR_a$, and —$NHCONR_aR_b$, wherein $R_a$ and $R_b$ are independently selected from hydrogen, alkyl, alkenyl, alkynyl, cycloalkyl, aryl, heteroaryl, heterocyclo, aralkyl, heteroaralkyl, and heterocycloalkyl;
- $R^2$ is selected from hydrogen, alkoxy, optionally substituted $C_1$–$C_8$-alkyl, optionally substituted $C_2$–$C_8$-alkenyl, and optionally substituted $C_2$–$C_8$-alkynyl, wherein the substituents are independently selected from halogen, alkyl, alkenyl, alkynyl, cycloalkyl, oxo, aryl, heteroaryl, heterocyclo, CN, nitro, —$COOR_a$, —$OCOR_a$, —$OR_a$, —$SR_a$, —$SOR_a$, —$SO_2R_a$, —$NR_aR_b$, —$CONR_aR_b$, —$OCONR_aR_b$, —$NHCOR_a$, —$NHCOOR_a$, and —$NHCONR_aR_b$, wherein $R_a$ and $R_b$ are independently selected from hydrogen, alkyl, alkenyl, alkynyl, cycloalkyl, aryl, heteroaryl, heterocyclo, aralkyl, heteroaralkyl, and heterocycloalkyl;
- $R^3$ is selected from hydrogen, optionally substituted alkyl, optionally substituted alkenyl, optionally substituted alkynyl, cycloalkyl, optionally substituted aryl, and optionally substituted heteroaryl;
- $R^4$ is hydrogen or a hydroxy protecting group;
- $R^5$ is selected from hydrogen, $C_1$–$C_8$-alkyl, $C_2$–$C_{10}$-alkenyl, $C_2$–$C_{10}$-alkynyl, aryl, heteroaryl, heterocyclo, aryl($C_1$–$C_{10}$)alkyl, aryl($C_2$–$C_{10}$)alkenyl, aryl($C_2$–$C_{10}$) alkynyl, heterocyclo($C_1$–$C_{10}$)alkyl, heterocyclo($C_2$–$C_{10}$)alkenyl, and heterocyclo($C_2$–$C_{10}$)alkynyl, $C_3$–$C_6$-cycloalkyl, $C_5$–$C_8$-cycloalkenyl, alkoxyalkyl containing 1–6 carbon atoms in each alkyl or alkoxy group, and alkylthioalkyl containing 1–6 carbon atoms in each alkyl or thioalkyl group;
- L is absent or C(O);
- W is NH or O;
- X and X', together with the carbon atom to which they are attached, form C=O, C=$NR_c$, or C=$NOR_c$, wherein $R_c$ is independently selected from hydrogen, alkyl, alkenyl and alkynyl; and
- Z is selected from C(O), C(O)—O, C(O)—$NR^2$, and $SO_2$; and
- $R^6$ is selected from optionally substituted aryl, optionally substituted heteroaryl, optionally substituted heterocyclyl, optionally substituted cycloalkyl, optionally substituted $C_1$–$C_8$-alkyl, optionally substituted $C_2$–$C_8$-alkenyl, and optionally substituted $C_2$–$C_8$-alkynyl, wherein the substituents are selected from halogen, alkyl, alkenyl, alkynyl, cycloalkyl, oxo, alkoxyimino, aryl, heteroaryl, heterocyclo, CN, nitro, —$COOR_a$, —$OCOR_a$, —$OR_a$, —$SR_a$, —$SOR_a$, —$SO_2R_a$, —$NR_aR_b$, —$CONR_aR_b$, —$OCONR_aR_b$, —$NHCOR_a$, —$NHCOOR_a$, and —$NHCONR_aR_b$, wherein $R_a$ and $R_b$ are independently selected from hydrogen, alkyl, alkenyl, alkynyl, cycloalkyl, aryl, heteroaryl, heterocyclo, aralkyl, heteroaralkyl, and heterocycloalkyl, or $NR^2R^6$ taken together form heterocyclyl having at least one N atom;

or an optical isomer, enantiomer, diastereomer, racemate or racemic mixture thereof, or a pharmaceutically acceptable salt, esters or pro-drugs thereof.

Compounds of the above formula are useful as antibacterial agents for the treatment of bacterial infections in a subject such as human and animal.

The present invention is also directed to a method of treating a subject having a condition caused by or contributed to by bacterial infection, which comprises administering to the subject a therapeutically effective amount of the compound of Formula 1.

The present invention is further directed to a method of preventing a subject from suffering from a condition caused by or contributed to by bacterial infection, which comprises administering to the subject a prophylactically effective amount of the compound of Formula 1.

Other objects and advantages will become apparent to those skilled in the art from a review of the ensuing specification.

DETAILED DESCRIPTION OF INVENTION

Relative to the above description, certain definitions apply as follows.

Unless otherwise noted, under standard nomenclature used throughout this disclosure the terminal portion of the designated side chain is described first, followed by the adjacent functionality toward the point of attachment.

Unless specified otherwise, the terms "alkyl", "alkenyl", and "alkynyl," whether used alone or as part of a substituent group, include straight and branched chains having 1 to 8 carbon atoms, or any number within this range. The term "alkyl" refers to straight or branched chain hydrocarbons. "Alkenyl" refers to a straight or branched chain hydrocarbon with at least one carbon—carbon double bond. "Alkynyl" refers to a straight or branched chain hydrocarbon with at least one carbon—carbon triple bound. For example, alkyl radicals include methyl, ethyl, n-propyl, isopropyl, n-butyl, isobutyl, sec-butyl, t-butyl, n-pentyl, 3-(2-methyl)butyl, 2-pentyl, 2-methylbutyl, neopentyl, n-hexyl, 2-hexyl and 2-methylpentyl. "Alkoxy" radicals are oxygen ethers formed from the previously described straight or branched chain alkyl groups. "Cycloalkyl" groups contain 3 to 8 ring carbons and preferably 5 to 7 ring carbons. The alkyl, alkenyl, alkynyl, cycloalkyl group and alkoxy group may be independently substituted with one or more members of the group including, but not limited to, halogen, alkyl, alkenyl, alkynyl, cycloalkyl, alkoxy, oxo, aryl, heteroaryl, heterocyclo, CN, nitro, —$OCOR_a$, —$OR_a$, —$SR_a$, —$SOR_a$, —$SO_2R_a$, —$COOR_a$, —$NR_aR_b$, —$CONR_aR_b$, —$OCONR_aR_b$, —$NHCOR_a$, —$NHCOOR_a$, and —$NHCONR_aR_b$, wherein $R_a$ and $R_b$ are independently selected from H, alkyl, alkenyl, alkynyl, cycloalkyl, aryl, heteroaryl, heterocyclo, aralkyl, heteroaralkyl, and heterocycloalkyl.

The term "acyl" as used herein, whether used alone or as part of a substituent group, means an organic radical having 2 to 6 carbon atoms (branched or straight chain) derived from an organic acid by removal of the hydroxyl group. The term "Ac" as used herein, whether used alone or as part of a substituent group, means acetyl.

The term "halo" or "halogen" means fluoro, chloro, bromo and iodo. (Mono-, di-, tri-, and per-)halo-alkyl is an alkyl radical substituted by independent replacement of the hydrogen atoms thereon with halogen.

"Aryl" or "Ar," whether used alone or as part of a substituent group, is a carbocyclic aromatic radical including, but not limited to, phenyl, 1- or 2-naphthyl and the like. The carbocyclic aromatic radical may be substituted by independent replacement of 1 to 3 of the hydrogen atoms thereon with halogen, OH, CN, mercapto, nitro, amino, $C_1$–$C_8$-alkyl, $C_1$–$C_8$-alkoxyl, $C_1$–$C_8$-alkylthio, $C_1$–$C_8$-alkyl-amino, di($C_1$–$C_8$-alkyl)amino, (mono-, di-, tri-, and per-)halo-alkyl, formyl, carboxy, alkoxycarbonyl, $C_1$–$C_8$-alkyl-CO—O—, $C_1$–$C_8$-alkyl-CO—NH—, or carboxamide. Illustrative aryl radicals include, for example, phenyl, naphthyl, biphenyl, fluorophenyl, difluorophenyl, benzyl, benzoyloxyphenyl, carboethoxyphenyl, acetylphenyl, ethoxyphenyl, phenoxyphenyl, hydroxyphenyl, carboxyphenyl, trifluoromethylphenyl, methoxyethylphenyl, acetamidophenyl, tolyl, xylyl, dimethylcarbamylphenyl and the like. "Ph" or "PH" denotes phenyl.

Whether used alone or as part of a substituent group, "heteroaryl" refers to a cyclic, fully unsaturated radical having from five to ten ring atoms of which one ring atom is selected from S, O, and N; 0–2 ring atoms are additional heteroatoms independently selected from S, O, and N; and the remaining ring atoms are carbon. The radical may be joined to the rest of the molecule via any of the ring atoms. Exemplary heteroaryl groups include, for example, pyridinyl, pyrazinyl, pyrimidinyl, pyridazinyl, pyrroyl, pyrazolyl, imidazolyl, thiazolyl, oxazolyl, isoxazolyl, thiadiazolyl, triazolyl, triazinyl, oxadiazolyl, thienyl, furanyl, quinolinyl, isoquinolinyl, indolyl, isothiazolyl, N-oxo-pyridyl, 1,1-dioxothienyl, benzothiazolyl, benzoxazolyl, benzothienyl, quinolinyl-N-oxide, benzimidazolyl, benzopyranyl, benzisothiazolyl, benzisoxazolyl, benzodiazinyl, benzofurazanyl, indazolyl, indolizinyl, benzofuryl, cinnolinyl, quinoxalinyl, indazolyl, pyrrolopyridinyl, furopyridinyl (such as furo[2,3-c] pyridinyl, furo[3,2-b]pyridinyl, or furo[2,3-b]pyridinyl), imidazopyridinyl (such as imidazo[4,5-b]pyridinyl or imidazo[4,5-c]pyridinyl), naphthyridinyl, phthalazinyl, purinyl, pyridopyridyl, quinazolinyl, thienofuryl, thienopyridyl, and thienothienyl. The heteroaryl group may be substituted by independent replacement of 1 to 3 of the hydrogen atoms thereon with halogen, OH, CN, mercapto, nitro, amino, $C_1$–$C_8$-alkyl, $C_1$–$C_8$-alkoxyl, $C_1$–$C_8$-alkylthio, $C_1$–$C_8$-alkyl-amino, di($C_1$–$C_8$-alkyl)amino, (mono-, di-, tri-, and per-)halo-alkyl, formyl, carboxy, alkoxycarbonyl, $C_1$–$C_8$-alkyl-CO—O—, $C_1$–$C_8$-alkyl-CO—NH—, or carboxamide. Heteroaryl may be substituted with a mono-oxo to give for example a 4-oxo-1H-quinoline.

The terms "heterocycle," "heterocyclic," and "heterocyclo" refer to an optionally substituted, fully saturated, partially saturated, or non-aromatic cyclic group which is, for example, a 4- to 7-membered monocyclic, 7- to 11-membered bicyclic, or 10- to 15-membered tricyclic ring system, which has at least one heteroatom in at least one carbon atom containing ring. Each ring of the heterocyclic group containing a heteroatom may have 1, 2, or 3 heteroatoms selected from nitrogen atoms, oxygen atoms, and sulfur atoms, where the nitrogen and sulfur heteroatoms may also optionally be oxidized. The nitrogen atoms may optionally be quaternized. The heterocyclic group may be attached at any heteroatom or carbon atom.

Exemplary monocyclic heterocyclic groups include pyrrolidinyl; oxetanyl; pyrazolinyl; imidazolinyl; imidazolidinyl; oxazolinyl; oxazolidinyl; isoxazolinyl; thiazolidinyl; isothiazolidinyl; tetrahydrofuryl; piperidinyl; piperazinyl; 2-oxopiperazinyl; 2-oxopiperidinyl; 2-oxopyrrolidinyl; 4-piperidonyl; tetrahydropyranyl; tetrahydrothiopyranyl; tetrahydrothiopyranyl sulfone; morpholinyl; thiomorpholinyl; thiomorpholinyl sulfoxide; thiomorpholinyl sulfone; 1,3-dioxolane; dioxanyl; thietanyl: thiiranyl; 2-oxazepinyl; azepinyl; and the like. Exemplary bicyclic heterocyclic groups include quinuclidinyl; tetrahydroisoquinolinyl; dihydroisoindolyl; dihydroquinazolinyl (such as 3,4-dihydro-4-oxo-quinazolinyl); dihydrobenzofuryl; dihydrobenzothienyl; benzothiopyranyl; dihydrobenzothiopyranyl; dihydrobenzothiopyranyl sulfone; benzopyranyl; dihydrobenzopyranyl; indolinyl; chromonyl; coumarinyl; isochromanyl; isoindolinyl; piperonyl; tetrahydroquinolinyl; and the like.

Substituted aryl, substituted heteroaryl, and substituted heterocycle may also be substituted with a second substituted-aryl, a second substituted-heteroaryl, or a second substituted-heterocycle to give, for example, a 4-pyrazol-1-yl-phenyl or 4-pyridin-2-yl-phenyl.

Designated numbers of carbon atoms (e.g., $C_{1-8}$) shall refer independently to the number of carbon atoms in an alkyl or cycloalkyl moiety or to the alkyl portion of a larger substituent in which alkyl appears as its prefix root.

Unless specified otherwise, it is intended that the definition of any substituent or variable at a particular location in a molecule be independent of its definitions elsewhere in that molecule. It is understood that substituents and substitution patterns on the compounds of this invention can be selected by one of ordinary skill in the art to provide compounds that are chemically stable and that can be readily synthesized by techniques known in the art as well as those methods set forth herein.

The term "hydroxy protecting group" refers to groups known in the art for such purpose. Commonly used hydroxy protecting groups are disclosed, for example, in T. H. Greene and P. G. M. Wuts, Protective Groups in Organic Synthesis, 2nd edition, John Wiley & Sons, New York (1991), which is incorporated herein by reference. Illustrative hydroxyl protecting groups include but are not limited to tetrahydropyranyl; benzyl; methylthiomethyl; ethythiomethyl; pivaloyl; phenylsulfonyl; triphenylmethyl; trisubstituted silyl such as trimethyl silyl, triethylsilyl, tributylsilyl, tri-isopropylsilyl, t-butyldimethylsilyl, tri-t-butylsilyl, methyldiphenylsilyl, ethyldiphenylsilyl, t-butyldiphenylsilyl; acyl and aroyl such as acetyl, pivaloylbenzoyl, 4-methoxybenzoyl, 4-nitrobenzoyl and aliphatic acylaryl.

Where the compounds according to this invention have at least one stereogenic center, they may accordingly exist as enantiomers. Where the compounds possess two or more stereogenic centers, they may additionally exist as diastereomers. Furthermore, some of the crystalline forms for the compounds may exist as polymorphs and as such are intended to be included in the present invention. In addition, some of the compounds may form solvates with water (i.e., hydrates) or common organic solvents, and such solvates are also intended to be encompassed within the scope of this invention.

Some of the compounds of the present invention may have trans and cis isomers. In addition, where the processes for the preparation of the compounds according to the invention give rise to mixture of stereoisomers, these isomers may be separated by conventional techniques such as preparative chromatography. The compounds may be prepared as a single stereoisomer or in racemic form as a mixture of some possible stereoisomers. The non-racemic forms may be obtained by either synthesis or resolution. The compounds may, for example, be resolved into their components enantiomers by standard techniques, such as the formation of diastereomeric pairs by salt formation. The compounds may also be resolved by covalent linkage to a chiral auxiliary, followed by chromatographic separation and/or crystallographic separation, and removal of the chiral auxiliary. Alternatively, the compounds may be resolved using chiral chromatography.

The phrase "a pharmaceutically acceptable salt" denotes one or more salts of the free base which possess the desired pharmacological activity of the free base and which are neither biologically nor otherwise undesirable. These salts may be derived from inorganic or organic acids. Examples of inorganic acids are hydrochloric acid, nitric acid, hydrobromic acid, sulfuric acid, or phosphoric acid. Examples of organic acids are acetic acid, propionic acid, glycolic acid, lactic acid, pyruvic acid, malonic acid, succinic acid, malic acid, maleic acid, fumaric acid, tartaric acid, citric acid, benzoic acid, cinnamic acid, mandelic acid, methanesulfonic acid, ethanesulfonic acid, p-toluenesulfonic acid, methyl sulfonic acid, salicyclic acid and the like. Suitable salts are furthermore those of inorganic or organic bases, such as KOH, NaOH, Ca(OH)$_2$, Al(OH)$_3$, piperidine, morpholine, ethylamine, triethylamine and the like.

Included within the scope of the invention are the hydrated forms of the compounds which contain various amounts of water, for instance, the hydrate, hemihydrate, and sesquihydrate forms. The present invention also includes within its scope prodrugs of the compounds of this invention. In general, such prodrugs will be functional derivatives of the compounds which are readily convertible in vivo into the required compound. Thus, in the methods of treatment of the present invention, the term "administering" shall encompass the treatment of the various disorders described with the compound specifically disclosed or with a compound which may not be specifically disclosed, but which converts to the specified compound in vivo after administration to the patient. Conventional procedures for the selection and preparation of suitable prodrug derivatives are described, for example, in "Design of Prodrugs", ed. H. Bundgaard, Elsevier, 1985.

The term "subject" includes, without limitation, any animal or artificially modified animal. As a particular embodiment, the subject is a human.

The term "drug-resistant" or "drug-resistance" refers to the characteristics of a microbe to survive in presence of a currently available antimicrobial agent such as an antibiotic at its routine, effective concentration.

The compounds described in the present invention possess antibacterial activity due to their novel structure, and are useful as antibacterial agents for the treatment of bacterial infections in humans and animals. In particular, compounds of the present invention have activity against Gram-positive and Gram-negative respiratory pathogens. The following are representative compounds of the present invention:

3-Pyridineacetic acid, (3aS,4R,7R,8S,9S,10R,11R,13R,15R,15aR)-4-ethyltetradecahydro-3a,7,9,11,13,15-hexamethyl-2,6,14-trioxo-11-[[[[(2E)-3-[4-(2-pyrimidinyl)phenyl]-2-propenyl]amino]carbonyl]oxy]-10-[[3,4,6-trideoxy-3-(dimethylamino)-β-D-xylo-hexopyranosyl]oxy]-2H-oxacyclotetradecino[4,3-d]oxazol-8-yl ester;

Propanoic acid, 2-methyl-, (3aS,4R,7R,8S,9S,10R, 11R,13R,15R,15aR)-4-ethyltetradecahydro-3a,7,9,11,13,15-hexamethyl-2,6,14-trioxo-11-[[[[(2E)-3-[4-(2-pyrimidinyl)phenyl]-2-propenyl]amino]carbonyl]oxy]-10-[[3,4,6-trideoxy-3-(dimethylamino)-β-D-xylo-hexopyranosyl]oxy]-2H-oxacyclotetradecino[4,3-d]oxazol-8-yl ester;

2-Pyridineacetic acid, (3aS,4R,7R,8S,9S,10R, 11R,13R,15R,15aR)-4-ethyltetradecahydro-3a,7,9,11,13,15-hexamethyl-2,6,14-trioxo-11-[[[[(2E,4E)-5-(3-pyridinyl)-2,4-pentadienyl]amino]carbonyl]oxy]-10-[[3,4,6-trideoxy-3-(dimethylamino)-β-D-xylo-hexopyranosyl]oxy]-2H-oxacyclotetradecino[4,3-d]oxazol-8-yl ester;

Propanoic acid, 2-methyl-, (3aS,4R,7R,8S,9S,10R,11R,13R,15R,15aR)-4-ethyltetradecahydro-3a,7,9,11,13,15-hexamethyl-2,6,14-trioxo-11-[[[[(2E)-3-(3-quinolinyl)-2-propenyl]amino]carbonyl]oxy]-10-[[3,4,6-trideoxy-3-(dimethylamino)-β-D-xylo-hexopyranosyl]oxy]-2H-oxacyclotetradecino[4,3-d]oxazol-8-yl ester;

Carbonic acid, (3aS,4R,7R,8S,9S,10R,11R,13R,15R,15aR)-8-[[(diethylamino)carbonyl]oxy]-4-ethyltetradecahydro-3a,7,9,11,13,15-hexamethyl-2,6,14-trioxo-10-[[3,4,6-trideoxy-3-(dimethylamino)-β-D-xylo-hexopyranosyl]oxy]-2H-oxacyclotetradecino[4,3-d]oxazol-11-yl(2E)-3-[4-(3-pyridazinyl)phenyl]-2-propenyl ester;

Propanoic acid, 2-methyl-, (3aS,4R,7R,8S,9S,10R,11R,13R,15R,15aR-4-ethyltetradecahydro-3a,7,9,11,13,15-hexamethyl-2,6,14-trioxo-11-[[[[(2E)-3-[4-(3-pyridazinyl)phenyl]-2-propenyl]oxy]carbonyl]oxy]-10-[[3,4,6-trideoxy-3-(dimethylamino)-β-D-xylo-hexopyranosyl]oxy]-2H-oxacyclotetradecino[4,3-d]oxazol-8-yl ester;

2-Pyridineacetic acid, (3aS,4R,7R,8S,9S,10R,11R,13R,15R, 15aR)-4-ethyltetradecahydro-3a,7,9,11,13,15-hexamethyl-2,6,14-trioxo-11-[[[[(2E)-3-[4-(2-pyrimidinyl)phenyl]-2-propenyl]oxy]carbonyl]oxy]-10-[[3,4,6-trideoxy-3-(dimethylamino)-β-D-xylo-hexopyranosyl]oxy]-2H-oxacyclotetradecino[4,3-d]oxazol-8-yl ester;

3-Pyridineacetic acid, (3aS,4R,7R,8S,9S,10R,11R,13R,15R,15aR)-4-ethyltetradecahydro-3a,7,9,11,13,15-hexamethyl-2,6,14-trioxo-11-[[[[(2E)-3-[4-(3-pyridazinyl)phenyl]-2-propenyl]oxy]carbonyl]oxy]-10-[[3,4,6-trideoxy-3-(dimethylamino)-β-D-xylo-hexopyranosyl]oxy]-2H-oxacyclotetradecino[4,3-d]oxazol-8-yl ester.

This invention also provides processes for preparing the instant compounds. The compounds of Formula 1 may be prepared from readily available starting materials such as erythromycin and erythromycin derivatives well known in the art. Outlined in Schemes 1 through 11 are representative procedures to prepare the compounds of the instant invention:

Scheme 1 illustrates the method of synthesizing the 2'4"-diacetyl-6-carbamoyl-11,12-dideoxy-11,12-iminocarbonyloxyerythromycin A (VI) and the 2'-acetyl-6-carbamoyl-11,12-dideoxy-3-O-descladinosyl-11,12- iminocarbonyloxyerythromycin A (VII) precursors to the compounds of the invention.
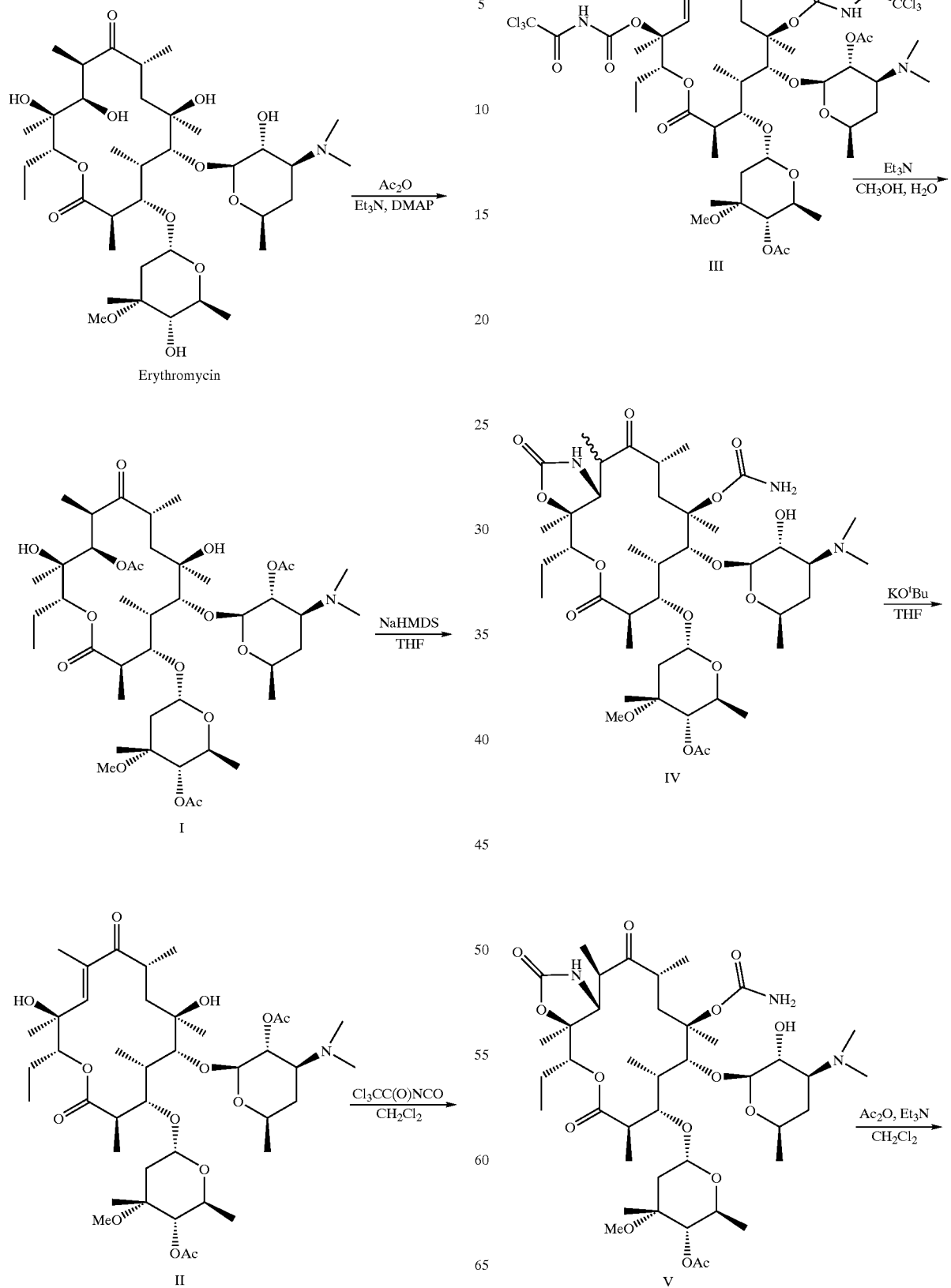
Scheme 1

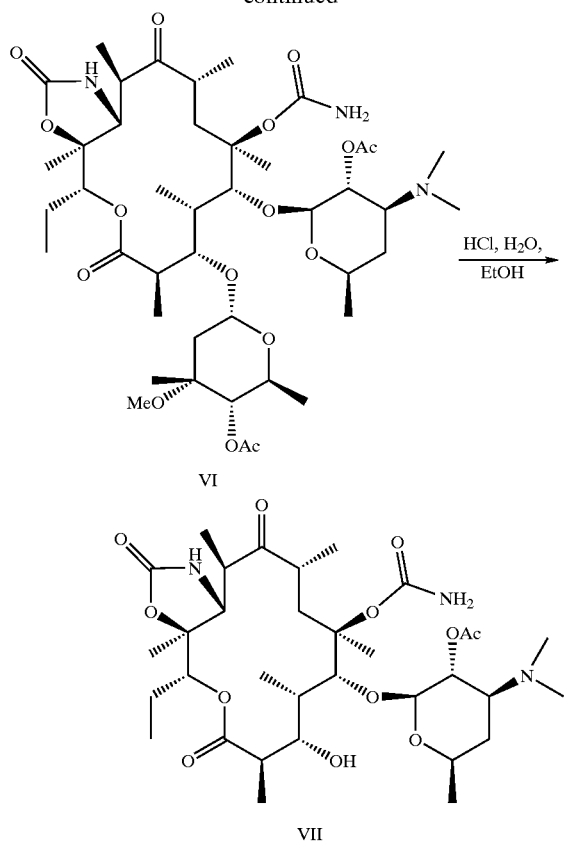

Erythromycin A is treated with acetic anhydride in the presence of a tertiary amine base, such as triethylamine, diisopropylethylamine, or pyridine, and an acylation catalyst, such as DMAP, in a suitable solvent such as methylene chloride, chloroform or THF at a temperature ranging from −20° C. to 37° C. for 2 to 48 hours to afford 2',4'',11-triacetylerythromycin A (I). The 10,11-anhydro derivative (II) can be readily obtained by treatment of 1 with a base in an inert solvent such as THF, dioxane, DME, or DMF at a temperature ranging from −78° C. to 80° C. for 1–24 hours. Suitable bases to effect the elimination reaction include, but are not limited to, sodium hexamethyldisilazide, potassium hexamethyldisilazide, LDA, lithium tetramethylpiperidide, DBU, and tetramethylguanidine. It will be apparent to one skilled in the art that alternative methods for synthesis of 2',4''-diacetyl-10,11-anhydroerythromycin A are available, including conversion of erythromycin A to the 11,12-cyclic carbonate derivative with ethylene carbonate, followed by elimination with tetramethylguanidine, as described in Hauske, J. R. and Kostek, G., *J. Org. Chem.* 1982, 47, 1595. Selective protection of the 2' and 4''-hydroxyl groups can then be readily accomplished with acetic anhydride in the presence of a tertiary amine base. Likewise, alternative protecting group strategies may be employed. For example, erythromycin A may be treated with benzoic anhydride, propionic anhydride, or formic acetic anhydride under similar conditions as described above to obtain the 2',4'',11-triacylated erythromycin A derivative followed by elimination to afford the corresponding 10,11-anhydro compound.

Once the suitably protected 10,11-anhydro derivative is obtained, derivatization of both tertiary hydroxyl groups can be carried out by treatment with trichloroacetylisocyanate in an inert solvent, such as methylene chloride, chloroform, or THF at a temperature ranging from −20° C. to 37° C. for 1–24 hours to yield the di-(N-trichloroacetyl)carbamate derivative (III). The N-trichloroacetylcarbamate functionalities can be hydrolyzed to the corresponding primary carbamates by treatment with a suitable base, such as triethylamine, in an aqueous solvent mixture, such as methanol/water for 1–24 hours at a temperature ranging from 20° C. to 80° C. Alternative bases may likewise be used to effect this conversion, such as sodium hydroxide, potassium hydroxide, sodium carbonate and potassium carbonate. Under the reaction conditions, the primary carbamate formed at the 12-position undergoes spontaneous Michael addition to the electrophilic 11-position of the α,β-unsaturated ketone and the 2'-acetoxy group is hydrolyzed to the corresponding hydroxyl to afford the cyclic carbamate derivative (IV). Compound IV is generally isolated as a mixture of methyl epimers at the C10-position, which can be readily converted to the desired C10-□-methyl epimer (V) by treatment with an equilibrating base, such as potassium t-butoxide, tetramethylguanidine, or DBU in a suitable solvent, such as THF, dioxane, DME, DMF or t-butanol at a temperature ranging from −78° C. to 80° C. for 1 to 24 hours. Reprotection of the 2'-hydroxyl group to give VI can be carried out by treatment with acetic anhydride in the presence of a tertiary amine base, such as triethylamine, diisopropylethylamine, or pyridine, and optionally an acylation catalyst, such as DMAP, in a suitable solvent such as methylene chloride, chloroform or THF at a temperature ranging from −20° C. to 37° C. for 2 to 48 hours. It is understood that an orthogonal protection strategy of the sugar hydroxyls may also be employed by treatment of V with alternate reagents such as benzoic anhydride, benzyl chloroformate, hexamethyldisilazane, or a trialkylsilyl chloride. Finally, selective removal of the cladinose sugar can be accomplished by reaction of VI with an acid, such as hydrochloric, sulfuric, chloroacetic, and trifluoroacetic, in the presence of alcohol and water to afford VII. Reaction time is typically 0.5–24 hours at a temperature ranging from −10° C. to 37° C.

Scheme 2 describes the synthesis of compounds of formulae VIII, 1c and 1d, wherein RCHO is an aldehyde (R may be a member of the group including, but not limited to, hydrogen, alkyl, alkenyl, alkynyl, cycloalkyl, aryl, heteroaryl, heterocycle, arylalkenyl, arylalkynyl, aralkyl, heteroarylalkenyl, heteroarylalkynyl, heteroarylalkyl, heterocycloalkenyl, heterocycloalkynyl, and heterocycloalkyl). Compounds of formula VIII can be obtained by selective alkylation of the primary carbamate of VII with a suitably substituted aldehyde in the presence of a reducing agent and acid. Alternatively, the corresponding acetal may be used in place of the suitably substituted aldehyde. Preferred reagents for effecting this transformation are triethylsilane and trifluoroacetic acid in a suitable solvent, like acetonitrile, methylene chloride, or toluene at −20° C. to 100° C. Typically, the reaction is conducted for from 2–96 hours depending on the reactivity of the aldehyde or acetal. Esterification of the 3-hydroxy group of VIII can be conducted with a carboxylic acid and a carbodiimide, such as DCC or EDCI, in the presence of catalytic amount dimethylaminopyridine (DMAP), in an inert solvent such as methylene chloride or THF to give compound 1c. Typically, this reaction is conducted for from 2 hours to 10 days at temperatures ranging from 0° C. to room temperature. Alternative methods of esterification include using a carboxylic acid anhydride or carboxylic acid chloride with triethylamine and a catalytic amount of DMAP in an inert solvent such as methylene chloride or THF. Typically reaction times are from 2 hours to 10 days at temperatures ranging from 0° C. to room temperature. Removal of the 2'-acetyl group of compound 1c is readily accomplished by transesterification with methanol for 16–72 hours at room temperature to give compound 1d.

synthetic sequence. Esterificaton of the 3-hydroxy group of compound VII is conducted as above to yield compound 1e. The primary carbamate of compound 1e is then selectively alkylated to give compound 1c, which is sequentially converted to compound 1d, using methods described above.

Scheme 2

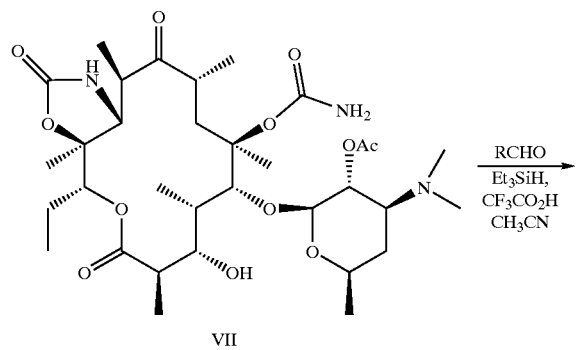

VII

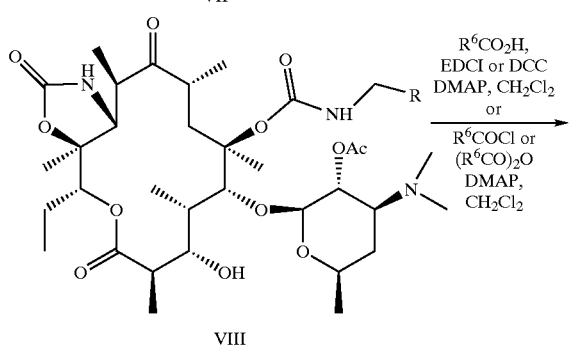

VIII

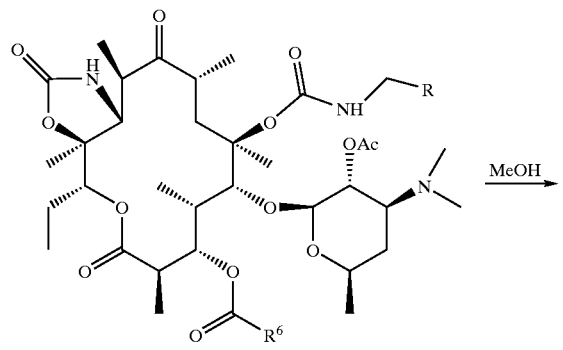

1c

Scheme 3

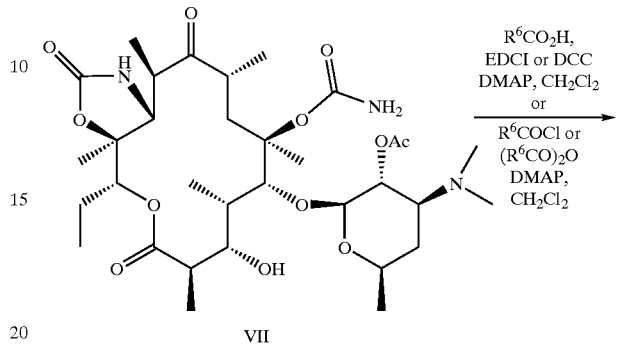

VII

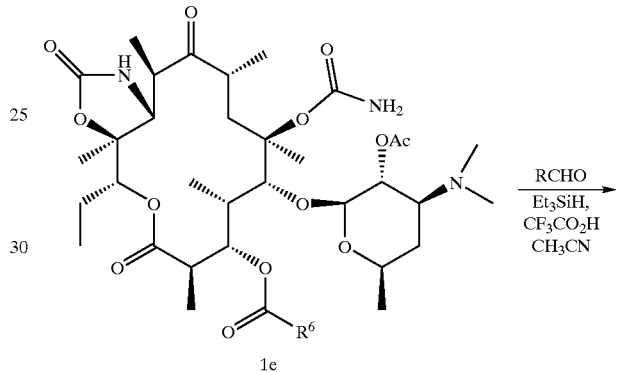

1e

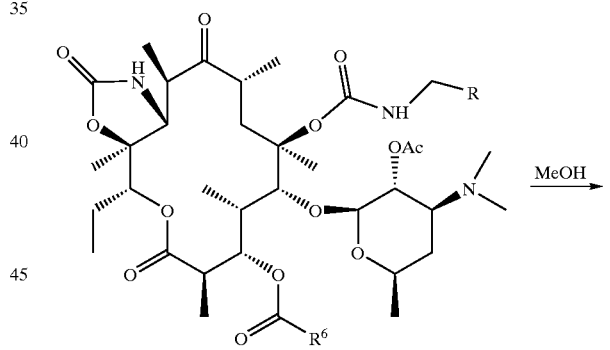

1c 1d                                          1d

Scheme 3 illustrates an alternate route for the preparation of compound 1 d, by changing the order of the steps in the Scheme 4 describes the preparation of 3,6-dicarbamoyl compounds of formulae 1f and 1g. Reaction of compound VIII with an isocyanate in the presence of dimethylaminopyridine (DMAP) in a suitable solvent such as methylene chloride or toluene converts the hydroxyl group of VIII to the corresponding secondary carbamate 1f. Typically this reaction is conducted for from 2 to 72 hours at temperatures ranging from 0° C. to 110° C. Removal of the 2'-acetyl group of compound 1f with methanol as described above, yields compound 1g.

Scheme 4

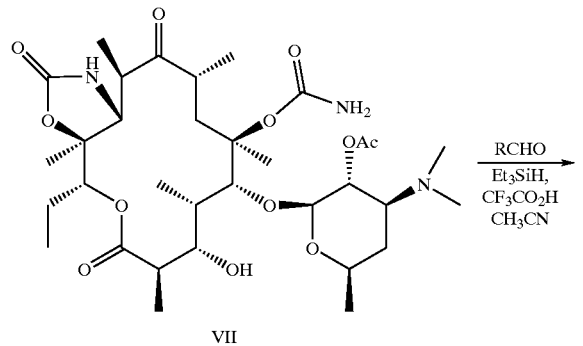

VII

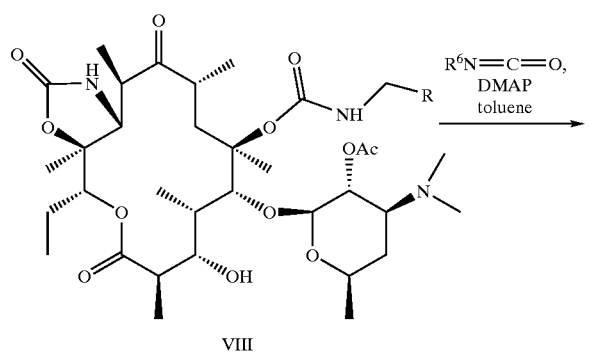

VIII

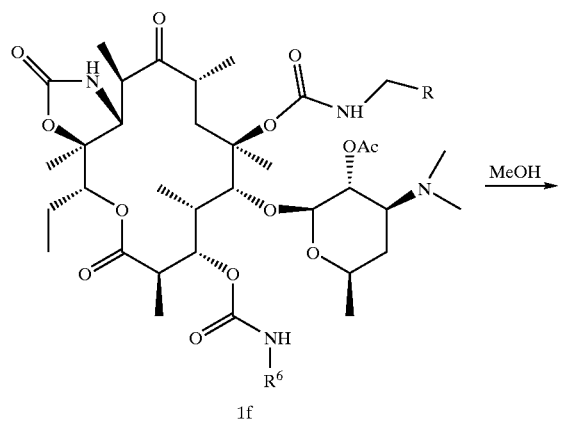

1f

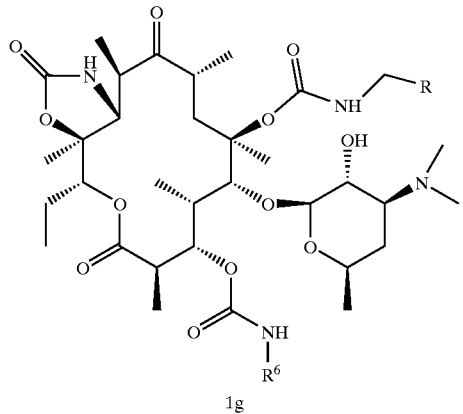

1g

Scheme 5 illustrates another route to the 3,6-dicarbamoyl compounds of the invention, including analogs with a tertiary carbamate in the 3-position, as in compounds of formulae 1i and 1j. Compound VIII is treated with diphosgene (ClC(O)OCCl₃) in the presence of a base, such as triethylamine or pyridine, and dimethylaminopyridine (DMAP) in an inert solvent such as methylene chloride for from 2 to 72 hours at temperatures ranging from 0° C. to room temperature to give the 3-carbonate compound 1h. Reaction of compound 1h with a primary or secondary amine in the presence of a base, such as triethylamine or pyridine, and dimethylaminopyridine (DMAP) in a suitable solvent, such as methylene chloride or THF, for from 2 to 48 hours at temperatures ranging from 0° C. to 60° C. leads to 3-carbamate compound 1i. Removal of the 2'-acetyl group is accomplished by transesterification with methanol to give compound 1j.

Scheme 5

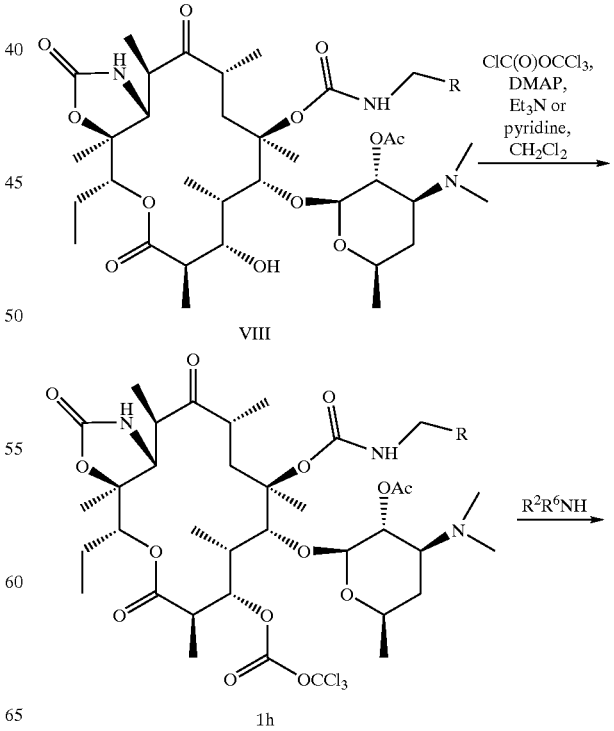

VIII

1h

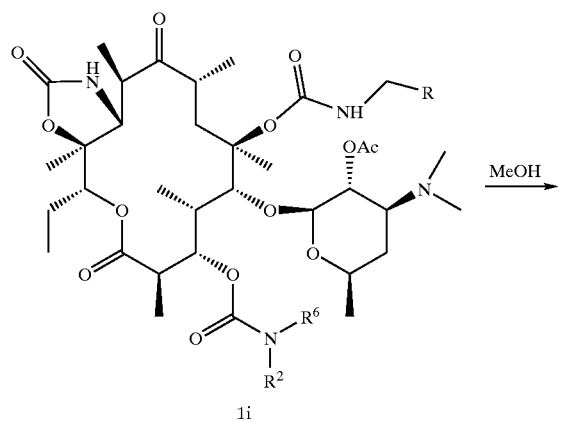

1i

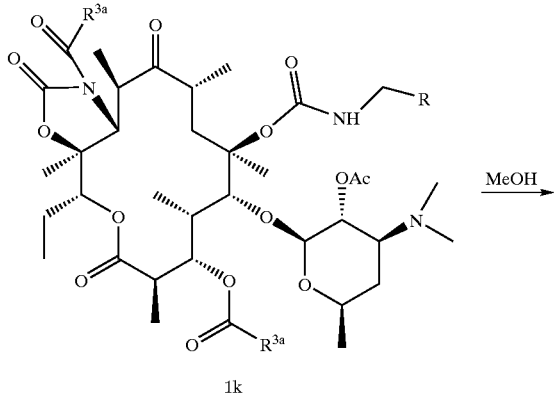

1k

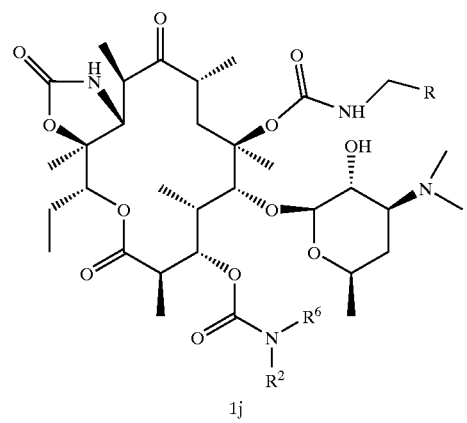

1j

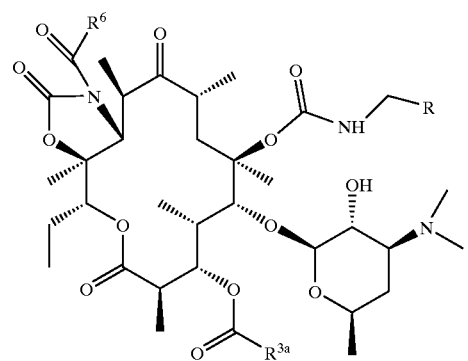

1l

Scheme 6 describes the synthesis of 11-N-acyl-6-carbamoyl compounds of formulae 1k and 1l. In cases where a particularly reactive acylating agent is employed, the 11-carbamate of VIII can be acylated in the presence of excess reagents to give 11-N, 3-diacyl product 1k, which after removal of the 2'-acetyl group under conditions described above gives compound 1l.

Functional groups other than an ester or carbamate can be introduced in the 3-position. Scheme 7 illustrates the synthesis of 3-sulfonate compounds of formulae 1m and 1n, by reaction of compound VIII with a suitably substituted sulfonyl chloride in the presence of an amine base, such as triethylamine, and an acylation catalyst, such as DMAP, in a inert solvent, such as methylene chloride or THF. Typically this reaction is conducted for from 2 to 48 hours at temperatures ranging from 0° C. to room temperature.

Scheme 6

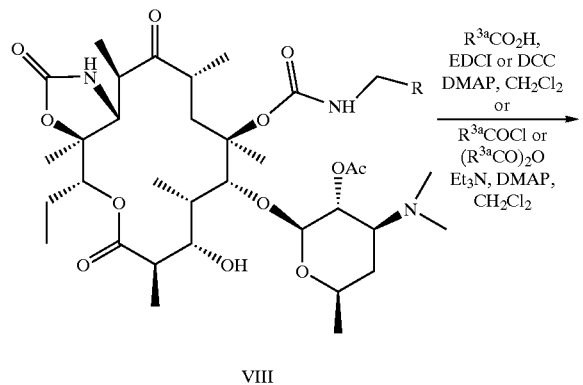

VIII

Scheme 7

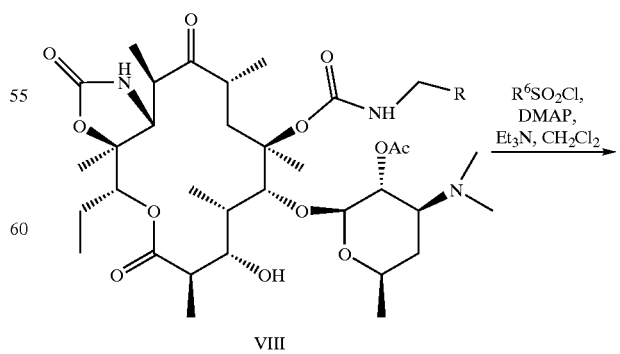

VIII

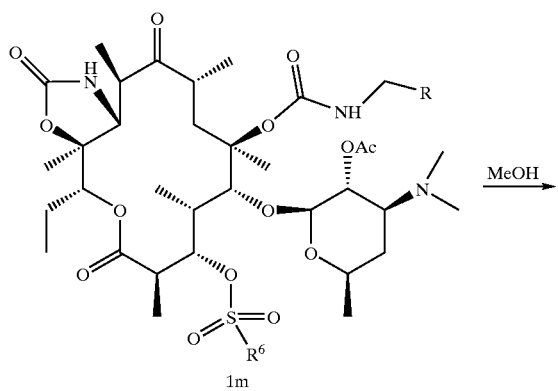

1m

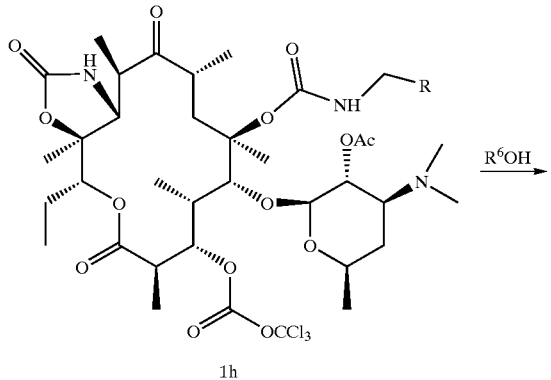

1h

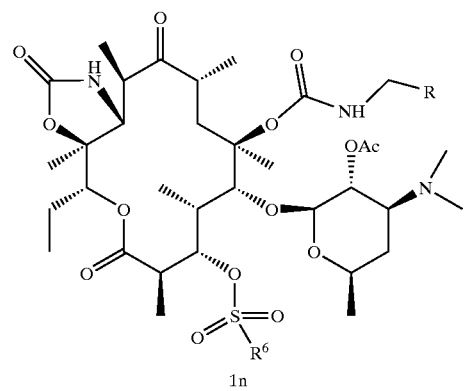

1n

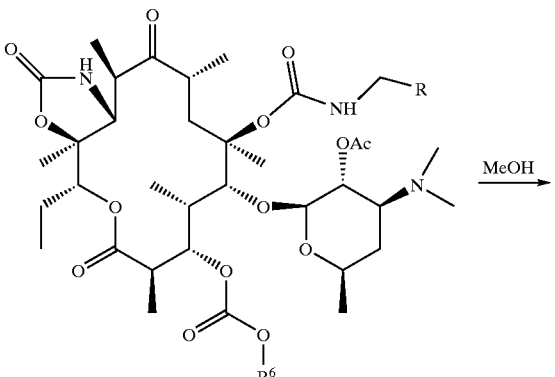

1o

Scheme 8 describes the synthesis of 3-carbonate compounds of formulae 1o and 1p. Compound VIII is treated with diphosgene (ClC(O)OCCl$_3$) in the presence of a base, such as triethylamine or pyridine, and dimethylaminopyridine (DMAP) in an inert solvent such as methylene chloride for from 2 to 72 hours at temperatures ranging from 0° C. to room temperature to give the 3-carbonate compound 1h. Reaction of compound 1 h with a suitably substituted alcohol in the presence of a base, such as triethylamine or pyridine, and dimethylaminopyridine (DMAP) in an inert solvent, such as methylene chloride or THF, for from 2 to 72 hours at temperatures ranging from 0° C. to room temperature affords compound 1o. Removal of the 2'-acetyl group is accomplished by transesterification with methanol (as described above) to give compound 1p.

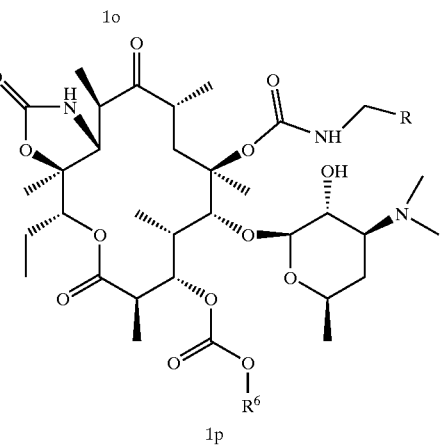

1p

Scheme 8

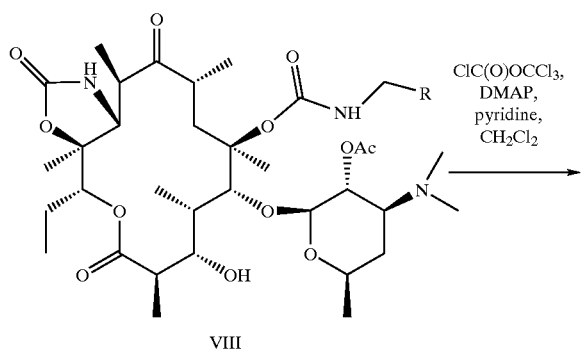

VIII

Scheme 9 describes the synthesis of compounds of formulae IX, X, 1s and 1t. Compound (IX) can be obtained by reaction of VII with 2-formyl, 4,4-dimethoxybutanenitrile in the presence of an acid. A preferred acid for effecting this transformation is trifluoroacetic acid in a suitable solvent, like acetonitrile, methylene chloride, or toluene at −20° C. to 100° C. Typically the reaction is conducted for from 2 to 96 hours. Compounds of formula X can be prepared by reaction of 1x with a suitably substituted alcohol in the presence of a suitable base, such as DBU, DBN, tert-butyltetramethylguanidine, sodium hydride, potassium hydride, or an alkyllithium in a suitable solvent, such as acetonitrile, dimethylformamide, dimethylsulfoxide, or THF, at a temperature ranging from −20° C. to 120° C. for 0.5 to 72 hours. Preformed alkali or alkaline earth metal alkoxides are also suitable reagents for the preparation of compounds of formula X. Compounds of formula 1s are prepared in an analogous fashion as for 1c and 1e by reaction of the 3-hydroxy group of X, with a carboxylic acid and a carbodiimide, such as DCC or EDCl, in the presence of a catalytic amount of DMAP in a suitable solvent such as methylene chloride or THF. Typically this reaction is conducted for from 2 hours to 10 days at temperatures ranging from 0° C. to room temperature. Alternative methods of esterification include using a carboxylic acid anhydride or carboxylic acid chloride with triethylamine and a catalytic amount of DMAP in an inert solvent, such as methylene chloride or THF. Typically, reaction times are from 2 hours to 10 days at temperatures ranging from 0° C. to room temperature. Removal of the 2'-acetyl group of 1s is readily accomplished by transesterification with methanol for 16 to 72 hours at room temperature to give compound 1t.

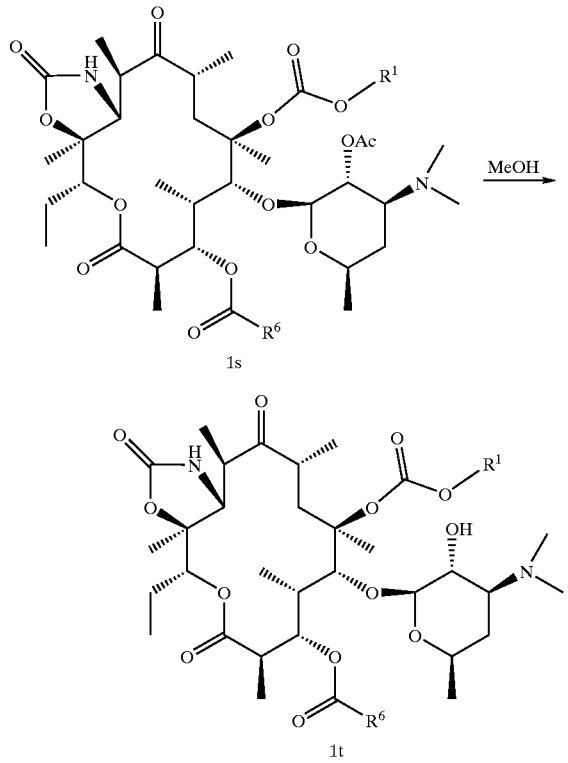

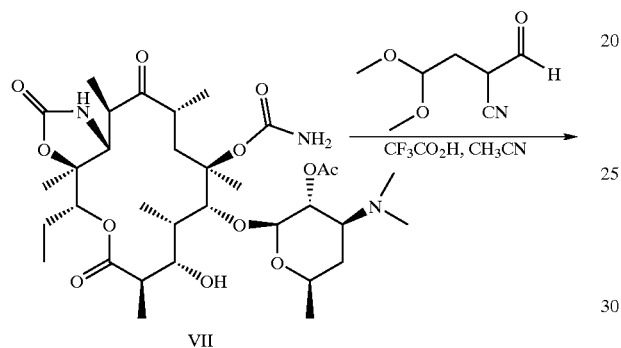

Scheme 10 illustrates an alternative method to prepare 3-acyl-6-carbonate compounds 1s and 1t, by changing the order of the steps in the synthetic sequence.

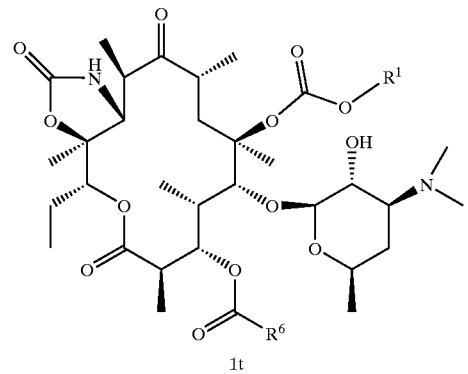

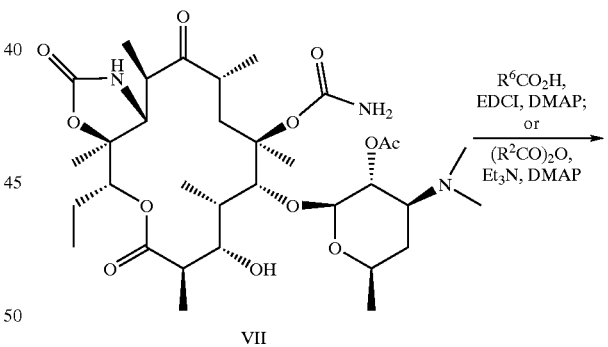

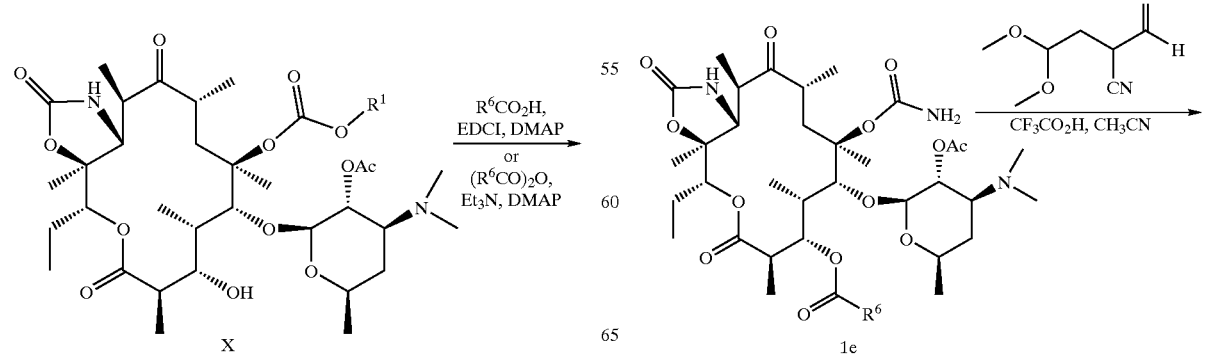

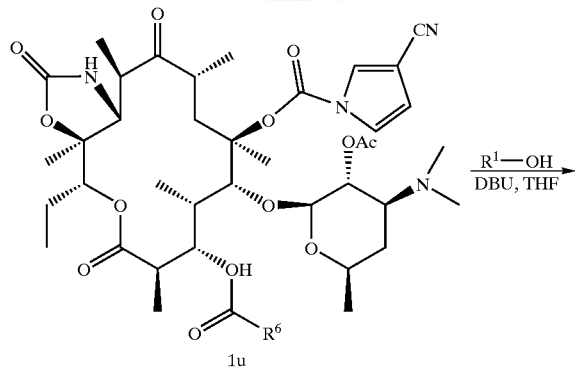

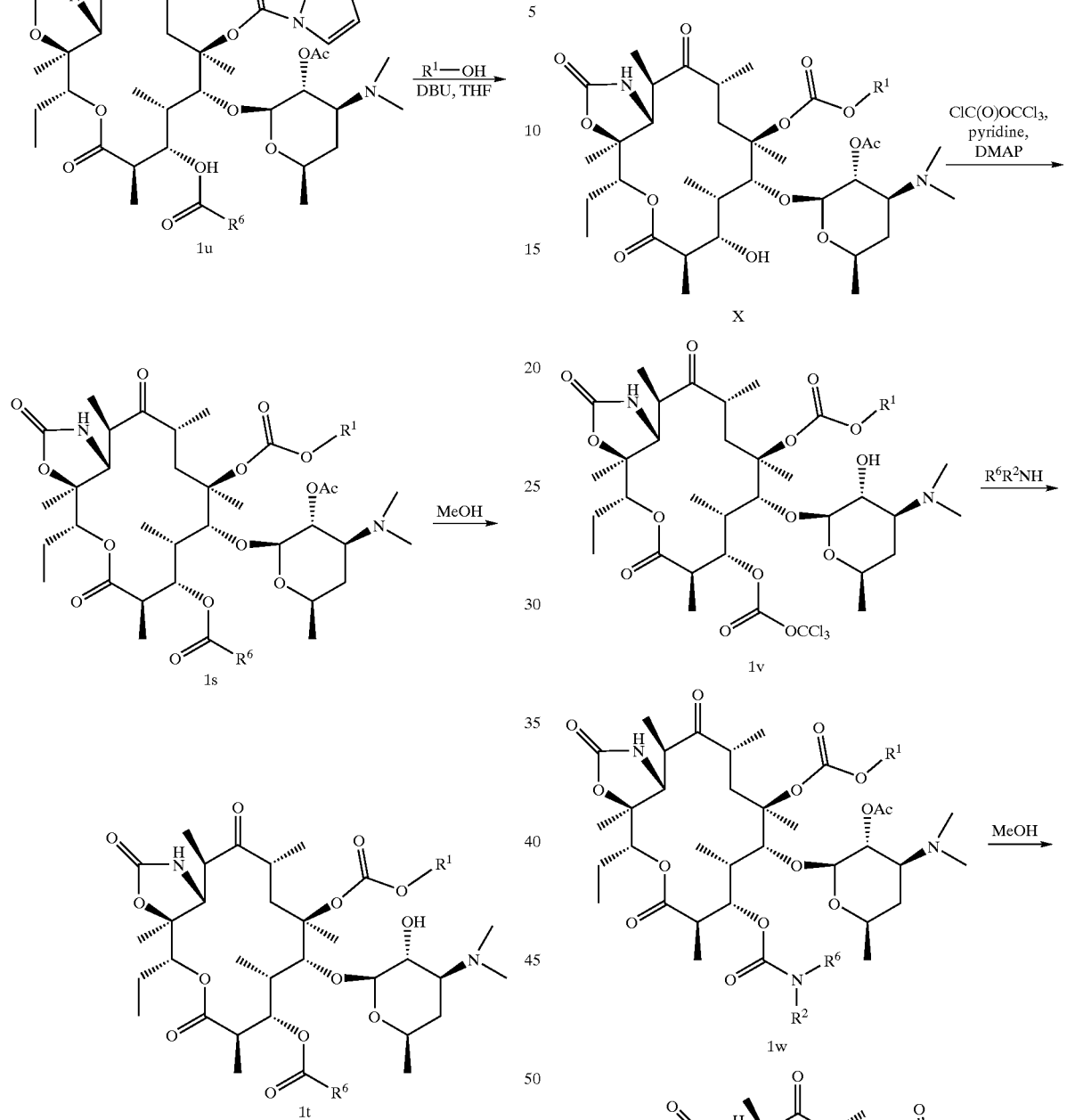

of the 2'-acetyl group is accomplished by transesterification with methanol to give compound 1x.

Scheme 11 describes the synthesis of 3-carbamoyl-6-carbonoyl compounds 1w and 1x through intermediate X. Compound X is treated with diphosgene (ClC(O)OCCl₃) in the presence of a base, such as triethylamine or pyridine, and dimethylaminopyridine (DMAP) in an inert solvent such as methylene chloride for from 2 to 72 hours at temperatures ranging from 0° C. to room temperature to give the 3-carbonate compound 1v. Reaction of compound 1v with a primary or secondary amine in the presence of a base, such as triethylamine or pyridine, and dimethylaminopyridine (DMAP) in a suitable solvent, such as methylene chloride or THF, for from 2 to 48 hours at temperatures ranging from 0° C. to 60° C. leads to 3-carbamate compound 1w. Removal

Scheme 12 -continued

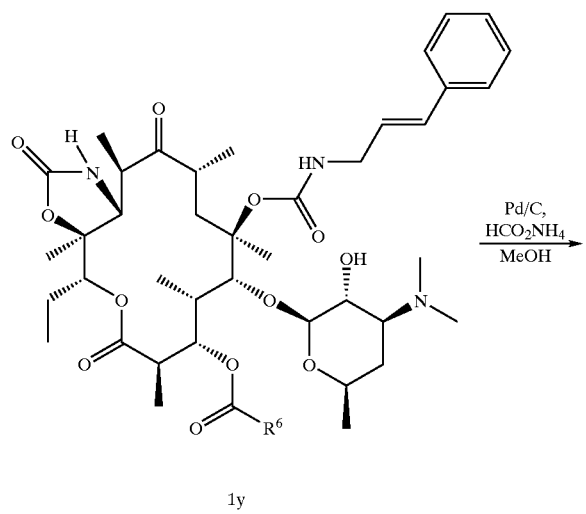

1y

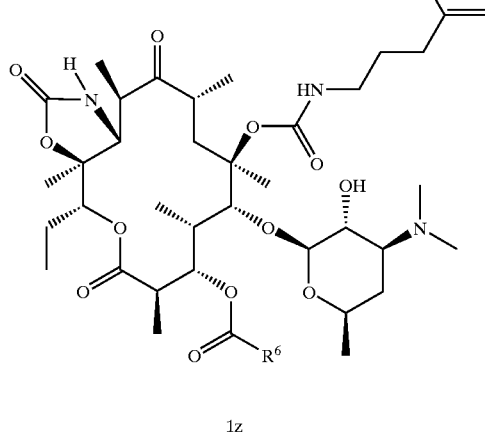

1z

Compounds which contain an alkenyl or alkynyl function may be converted to the corresponding saturated compounds. For example, as illustrated in Scheme 12, a substituted O-propenylcarbamate derivative such as 1y may be converted to the corresponding substituted O-propylcarbamate compound (1z). Typically, this transformation is conducted via catalytic transfer hydrogenation, in which the olefin is reacted with ammonium formate in the presence of a suitable catalyst, such as palladium on carbon, in a suitable solvent, such as methanol or ethanol, at a temperature ranging from 20° C. to 60° C. for 15 minutes to 24 hours. Other methods for reduction of the double bond could also be applicable, for example treatment with hydrogen in the presence of a noble metal catalyst, such as palladium or platinum. It will be obvious to one skilled in the art that the analogous O-propynylcarbamate may likewise be reduced to the corresponding O-propenylcarbamate or O-propylcarbamate under similar conditions.

Scheme 13

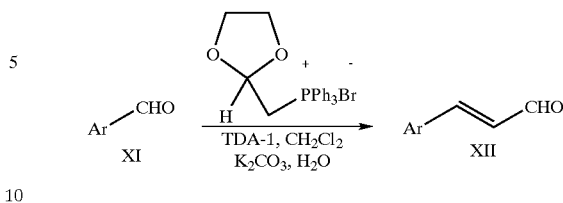

Scheme 13 illustrates a method of synthesis of certain of the aldehydes (XII) used in the preparation of compounds of the invention. Wittig-type reaction of an aromatic aldehyde (XI) with 1,3-dioxolan-2-yl-methyltriphenylphosphonium bromide under phase transfer conditions in a biphasic solvent system in the presence of an inorganic base, such as potassium carbonate, affords the corresponding vinylogous aldehyde (XII). Th reaction is typically run from 2 to 48 hours at temperatures ranging from 0° C. to 37° C. The method is more fully described in Daubresse, N., Francesch, C. and Rolando, C., *Tetrahedron*, 1998, 54, 10761.

Scheme 14

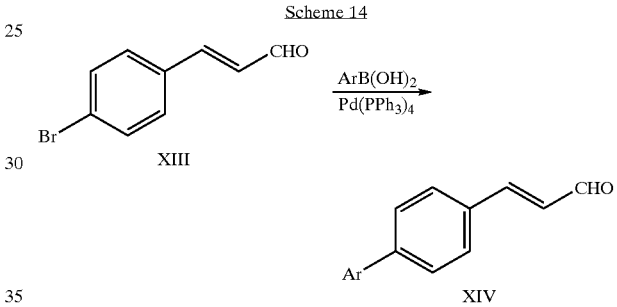

Scheme 14 also illustrates the synthesis of certain of the aldehydes (XIV) used in the preparation of compounds of the invention. Reaction of a bromocinnamaldehyde derivative (XIII) with an aryl boronic acid to give the biaryl derivative (XIV) is conducted under typical Suzuki coupling conditions, i.e., in the presence of a Pd⁰ catalyst, typically palladium tetrakistriphenylphosphine, and a base, typically sodium carbonate, potassium carbonate, sodium bicarbonate, potassium bicarbonate, potassium phosphate, or triethylamine in a suitable solvent, such as toluene, ethanol, methanol, DME, or THF. Reaction time is typically 2 to 48 hours at a temperature ranging from 20° C. to 110° C. Aryl iodides and aryl triflates are also suitable substrates for this conversion.

Scheme 15

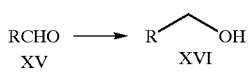

Scheme 15 illustrates a method for the preparation of certain alcohols (XVI) used in the preparation of some of the compounds of the invention. In this method, an aldehyde XV is reduced to the alcohol XVI. A preferred reducing agent is sodium borohydride in an alcoholic solvent such as methanol or ethanol. Another preferred reducing agent is diisobutylaluminum hydride in an inert solvent such as dichloromethane, toluene, or tetrahydrofuran. It will be obvious to one skilled in the art that numerous methods for reducing an aldehyde to an alcohol are known, and any of these may be suitable provided that the method is compatible with other functional groups that may be present in the molecule.

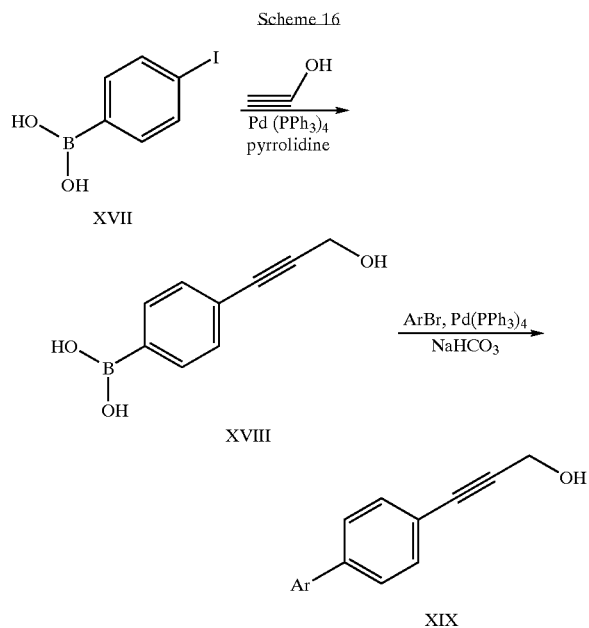

Scheme 16

Scheme 16 illustrates the synthesis of certain of the propargyl alcohols (XIX) used in the preparation of compounds of the invention. Reaction of halophenylboronic acid derivative (XVII) with propargyl alcohol to give the hydroxypropynylphenylboronic acid derivative (XVIII) is conducted in the presence of a Pd⁰ catalyst, typically palladium tetrakistriphenylphosphine, and pyrrolidine as solvent. Reaction time is typically from 2 to 48 hours at a temperature ranging from 0° C. to 85° C. Conversion of XVIII to the biarylpropargyl alcohol derivative (XIX) is then conducted under Suzuki coupling conditions, i.e., by reaction with an aryl or heteroaryl bromide in the presence of a Pd⁰ catalyst, typically palladium tetrakistriphenylphosphine, and a base, typically sodium carbonate, potassium carbonate, sodium bicarbonate, potassium bicarbonate, potassium phosphate, or triethylamine in a suitable solvent, such as toluene, ethanol, methanol, DME, THF, water, or aqueous solvent mixtures. Reaction time is typically 2 to 48 hours at a temperature ranging from 20° C. to 110° C. Aryl iodides and aryl triflates are also suitable substrates for this conversion.

Compounds of the invention wherein R is a hydroxy protecting group other than acyl may be prepared by methods analogous to those shown in the above schemes with appropriate reagents that are either commercially available or may be made by known methods.

Compounds of the invention wherein $R^5$ is a group other than ethyl may be prepared beginning with modified erythromycin derivatives as starting materials as described in various publications including, but not limited to, WO99/35157, WO00/62783. WO00/63224, and WO00/63225, which are all incorporated by reference herein.

These compounds have antimicrobial activity against susceptible and drug resistant Gram positive and Gram negative bacteria. In particular, they are useful as broad spectrum antibacterial agents for the treatment of bacterial infections in humans and animals. These compounds are particularly activity against S. aureus, S. epidermidis, S. pneumoniae, S. pyogenes, Enterococci, Moraxella catarrhalis and H. influenzae. These compounds are particularly useful in the treatment of community-acquired pneumonia, upper and lower respiratory tract infections, skin and soft tissue infections, meningitis, hospital-acquired lung infections, and bone and joint infections.

Minimal inhibitory concentration (MIC) has been an indicator of in vitro antibacterial activity widely used in the art. The in vitro antimicrobial activity of the compounds was determined by the microdilution broth method following the test method from the National Committee for Clinical Laboratory Standards (NCCLS). This method is described in the NCCLS Document M7-A4, Vol.17, No.2, "Methods for Dilution Antimicrobial Susceptibility Test for Bacteria that Grow Aerobically—Fourth Edition", which is incorporated herein by reference.

In this method two-fold serial dilutions of drug in cation adjusted Mueller-Hinton broth are added to wells in microdilution trays. The test organisms are prepared by adjusting the turbidity of actively growing broth cultures so that the final concentration of test organism after it is added to the wells is approximately $5 \times 10^4$ CFU/well.

Following inoculation of the microdilution trays, the trays are incubated at 35 □C for 16–20 hours and then read. The MIC is the lowest concentration of test compound that completely inhibits growth of the test organism. The amount of growth in the wells containing the test compound is compared with the amount of growth in the growth-control wells (no test compound) used in each tray. As set forth in Table 1, compounds of the present invention were tested against a variety of Gram positive and Gram negative pathogenic bacteria resulting in a range of activities depending on the organism tested.

Tables 1–3 below set forth the biological activity (MIC, □g/mL) of some compounds of the present invention.

TABLE 1

MIC Values (µg/mL) of Some 6-Carbamoyl-3-Acyl Macrolide Derivatives
(A: E. coli OC2605; B: S. aureus ATCC29213; C: E. faecalis ATCC29212; D: S. pneumoniae ATCC49619; E: H. influenzae ATCC49247)

| Compound No. | A | B | C | D | E |
|---|---|---|---|---|---|
| 1 | 16 | 0.5 | 0.25 | 0.06 | 1 |
| 2 | 16 | 0.5 | 0.25 | | 1 |
| 3 | >16 | 0.5 | 0.25 | 0.06 | 2 |
| 4 | 8 | 0.25 | 0.25 | 0.06 | 2 |
| 5 | >16 | 0.5 | 0.5 | 0.06 | 8 |
| 6 | >16 | 2 | 1 | 0.12 | >16 |
| 7 | >16 | 1 | 0.5 | 0.06 | 8 |
| 8 | 16 | 0.5 | 0.25 | 0.06 | 2 |
| 9 | >16 | 2 | 1 | 0.12 | 4 |
| 10 | >16 | 2 | 1 | 0.12 | 8 |
| 11 | >16 | 2 | 2 | 0.25 | 8 |
| 12 | >16 | 1 | 0.25 | 0.06 | 8 |
| 13 | >16 | 0.5 | 0.5 | 0.06 | 8 |
| 14 | 16 | 0.25 | 0.25 | 0.06 | 4 |
| 15 | >16 | 0.5 | 0.5 | 0.06 | 4 |
| 16 | >16 | 1 | 0.5 | 0.06 | 8 |
| 17 | 16 | 0.5 | 0.25 | 0.06 | 1 |
| 18 | >16 | 4 | 0.5 | 0.12 | 8 |
| 19 | 16 | 1 | 0.25 | 0.06 | 1 |
| 20 | 8 | 0.5 | 0.25 | 0.03 | 1 |
| 21 | 8 | 0.5 | 0.25 | 0.06 | 2 |
| 22 | 16 | 0.5 | 0.25 | 0.03 | 2 |
| 23 | 16 | 1 | 0.25 | 0.03 | 4 |
| 24 | >16 | 0.5 | 0.25 | <0.015 | 2 |
| 25 | 8 | 0.5 | 0.25 | 0.03 | 2 |
| 26 | 16 | 1 | 0.25 | 0.06 | 2 |
| 27 | 8 | 0.5 | 0.25 | 0.03 | 1 |

TABLE 1-continued

MIC Values (μg/mL) of Some 6-Carbamoyl-3-Acyl Macrolide Derivatives (A: *E. coli* OC2605; B: *S. aureus* ATCC29213; C: *E. faecalis* ATCC29212; D: *S. pneumoniae* ATCC49619; E: *H. influenzae* ATCC49247)

| Compound No. | A   | B    | C    | D      | E |
|---|---|---|---|---|---|
| 28 | 8   | 0.5  | 0.25 | <0.015 | 1 |
| 29 | 16  | 0.5  | 0.25 | 0.03   | 2 |
| 30 | 16  | 1    | 0.5  | 0.03   | 4 |
| 31 | 8   | 0.5  | 0.25 | 0.03   | 4 |
| 32 | 8   | 0.5  | 0.25 | 0.03   | 2 |
| 33 | 16  | 0.5  | 0.25 | 0.03   | 2 |
| 34 | 8   | 0.5  | 0.25 | 0.03   | 2 |
| 35 | 16  | 1    | 1    | 0.06   | 2 |
| 36 | 16  | 1    | 0.25 | 0.06   | 4 |
| 37 | 16  | 0.5  | 0.25 | 0.03   | 1 |
| 38 | >16 | 2    | 0.5  | 0.12   | 4 |
| 39 | 16  | 1    | 0.5  | 0.06   | 2 |
| 40 | >16 | 1    | 0.5  | 0.12   | 2 |
| 41 | >16 | 1    | 0.5  | 0.12   | 4 |
| 42 |     | 1    | 0.5  | 0.06   |   |
| 43 | 16  | 1    | 1    | 0.12   | 8 |
| 44 |     | 2    | 2    | 0.25   |   |
| 45 |     | 0.5  | 0.5  | 0.06   |   |
| 46 |     | 0.5  | 0.12 | 0.06   |   |
| 47 |     | 0.5  | 0.25 | 0.06   |   |
| 48 |     | 1    | 0.5  | 0.06   |   |
| 49 |     | 1    | 1    | 0.06   |   |

TABLE 2

MIC Values (μg/mL) of Some 3,6-Dicarbamoyl Macrolide Derivatives (A: *E. coil* OC2605; B: *S. aureus* ATCC29213; C: *E. faecalis* ATCC29212; D: *S. pneumoniae* ATCC49619; E: *H. influenzae* ATCC49247)

| Compound No. | A   | B    | C    | D    | E   |
|---|---|---|---|---|---|
| 50 | >16 | 1    | 0.5  | 0.12 | 4   |
| 51 | >16 | 1    | 0.5  | 0.12 | 2   |
| 52 | >16 | 1    | 1    | 0.12 | 4   |
| 53 | >16 | 2    | 1    | 0.25 | >16 |
| 54 | >16 | 2    | 2    | 0.5  | 16  |
| 55 | 16  | 0.5  | 0.25 | 0.03 | 4   |
| 56 | 16  | 0.5  | 0.5  | 0.06 | 4   |
| 57 | 16  | 0.5  | 0.5  | 0.06 | 4   |
| 58 | >16 | 0.25 | 0.25 | 0.03 | 2   |
| 59 | 16  | 0.5  | 0.25 | 0.06 | 4   |
| 60 | >16 | 1    | 0.5  | 0.06 | 4   |
| 61 | >16 | 1    | 0.5  | 0.06 | 8   |
| 62 | >16 | 0.5  | 0.5  | 0.06 | 4   |
| 63 | >16 | 0.5  | 0.5  | 0.06 | 4   |
| 64 | >16 | 1    | 0.5  | 0.06 | 8   |
| 65 | >16 | 1    | 1    | 0.25 | 8   |
| 66 | >16 | 4    | 2    | 0.25 | 16  |
| 67 | >16 | 0.5  | 0.5  | 0.06 | 8   |
| 68 |     | 1    | 0.5  | 0.06 |     |
| 69 |     | 0.5  | 0.5  | 0.06 |     |
| 70 |     | 1    | 0.5  | 0.06 |     |
| 71 |     | 1    | 1    | 0.06 |     |
| 72 |     | 0.5  | 0.5  | 0.06 |     |
| 73 |     | 1    | 0.5  | 0.12 |     |

TABLE 3

MIC Values (μg/mL) of Some 6-Carbonate Macrolide Derivatives (A: *E. coli* OC2605; B: *S. aureus* ATCC29213; C: *E. faecalis* ATCC29212; D: *S. pneumoniae* ATCC49619; E: *H. influenzae* ATCC49247)

| Compound No. | B    | C    | D    |
|---|---|---|---|
| 74 | 1    | 1    | 0.12 |
| 75 | 1    | 0.5  | 0.25 |
| 76 | 0.5  | 0.5  | 0.03 |
| 77 | 1    | 0.5  | 0.06 |
| 78 | 0.25 | 0.25 | 0.03 |
| 79 | 1    | 0.5  | 0.06 |
| 80 | 1    | 0.5  | 0.06 |
| 81 | 0.5  | 0.25 | 0.06 |
| 82 | 0.5  | 0.5  | 0.06 |
| 83 | 1    | 0.5  | 0.06 |
| 84 | 1    | 0.5  | 0.12 |
| 85 | 0.5  | 0.5  | 0.03 |
| 86 | 1    | 0.5  | 0.06 |

This invention further provides a method of treating bacterial infections, or enhancing or potentiating the activity of other antibacterial agents, in warm-blooded animals, which comprises administering to the animals a compound of the invention alone or in admixture with another antibacterial agent in the form of a medicament according to the invention.

When the compounds are employed for the above utility, they may be combined with one or more pharmaceutically acceptable carriers, e.g., solvents, diluents, and the like, and may be administered orally in such forms as tables, capsules, dispersible powders, granules, or suspensions containing for example, from about 0.5% to 5% of suspending agent, syrups containing, for example, from about 10% to 50% of sugar, and elixirs containing, for example, from about 20% to 50% ethanol, and the like, or parenterally in the form of sterile injectable solutions or suspensions containing from about 0.5% to 5% suspending agent in an isotonic medium. These pharmaceutical preparations may contain, for example, from about 0.5% up to about 90% of the active ingredient in combination with the carrier, more usually between 5% and 60% by weight.

Compositions for topical application may take the form of liquids, creams or gels, containing a therapeutically effective concentration of a compound of the invention admixed with a dermatologically acceptable carrier.

In preparing the compositions in oral dosage form, any of the usual pharmaceutical media may be employed. Solid carriers include starch, lactose, dicalcium phosphate, microcrystalline cellulose, sucrose and kaolin, while liquid carriers include sterile water, polyethylene glycols, non-ionic surfactants and edible oils such as corn, peanut and sesame oils, as are appropriate to the nature of the active ingredient and the particular form of administration desired. Adjuvants customarily employed in the preparation of pharmaceutical compositions may be advantageously included, such as flavoring agents, coloring agents, preserving agents, and antioxidants, for example, vitamin E, ascorbic acid, BHT and BHA.

The preferred pharmaceutical compositions from the standpoint of ease of preparation and administration are solid compositions, particularly tablets and hard-filled or liquid-filled capsules. Oral administration of the compounds is preferred. These active compounds may also be administered parenterally or intraperitoneally. Solutions or suspensions of these active compounds as a free base or pharmacological acceptable salt can be prepared in water suitably mixed with a surfactant such as hydroxypropylcellulose. Dispersions can also be prepared in glycerol, liquid polyethylene glycols and mixtures thereof in oils. Under ordinary conditions of storage and use, these preparations may contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), suitable mixtures thereof, and vegetable oils.

The effective dosage of active ingredient employed may vary depending on the particular compound employed, the mode of administration and the severity of the condition being treated. However, in general, satisfactory results are obtained when the compounds of the invention are administered at a daily dosage of from about 0.1 mg/kg to about 400 mg/kg of animal body weight, which may be given in divided doses two to four times a day, or in sustained release form. For most large mammals the total daily dosage is from about 0.07 g to 7.0 g, preferably from about 100 mg to 2000 mg. Dosage forms suitable for internal use comprise from about 100 mg to 1200 mg of the active compound in intimate admixture with a solid or liquid pharmaceutically acceptable carrier. This dosage regimen may be adjusted to provide the optimal therapeutic response. For example, several divided doses may be administered daily or the dose may be proportionally reduced as indicated by the exigencies of the therapeutic situation.

The production of the above-mentioned pharmaceutical compositions and medicaments is carried out by any method known in the art, for example, by mixing the active ingredients(s) with the diluent(s) to form a pharmaceutical composition (e.g. a granulate) and then forming the composition into the medicament (e.g. tablets).

The following examples describe in detail the chemical synthesis of representative compounds of the present invention. The procedures are illustrations, and the invention should not be construed as being limited by chemical reactions and conditions they express. No attempt has been made to optimize the yields obtained in these reactions, and it would be obvious to one skilled in the art that variations in reaction times, temperatures, solvents, and/or reagents could increase the yields.

EXAMPLE 1

Carbamic acid, [(2E)-3-[4-(2-pyrimidinyl)phenyl]-2-propenyl]-, (3aS,4R,7R,8S,9S,10R,11R,13R,15R,15aR)-10-[[2-O-acetyl-3,4,6-trideoxy-3-(dimethylamino)-β-D-xylo-hexopyranosyl]oxy]4-ethyltetradecahydro-8-hydroxy-3a,7,9,11,13,15-hexamethyl-2,6,14-trioxo-2H-oxacyclotetradecino[4,3-d]oxazol-11-yl ester

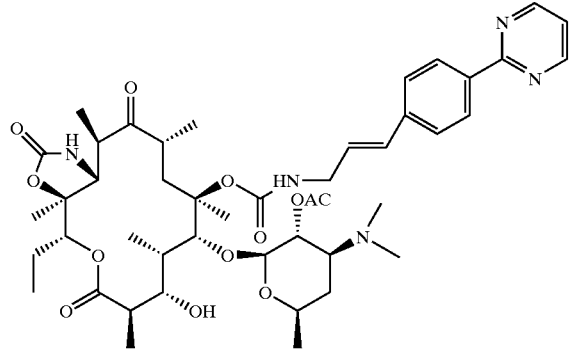

To the mixture of 2H-oxacyclotetradecino[4,3-d]oxazole-2,6,14(1H,7H)-trione, 10-[[2-O-acetyl-3,4,6-trideoxy-3-(dimethylamino)-β-D-xylo-hexopyranosyl]oxy]-11-[(aminocarbonyl)oxy]-4-ethyldecahydro-8-hydroxy-3a,7,9,11,13,15-hexamethyl-, (3aS,4R,7R,8S,9S,10R,11R,13R,15R,15aR-(1.0 g, 1.46 mmol) (Reference Example 1),

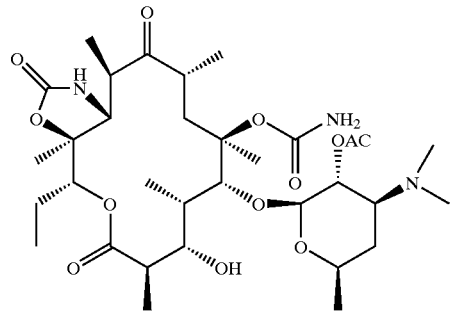

and (2E)-3-[4-(2-pyrimidinyl)phenyl]-propenylaldehyde (1.3 g, 6.2 mmol) (Reference Example 2) in CH$_3$CN (8 mL) was added triethylsilane (1.2 mL, 7.5 mmol) and trifluoroacetic acid (0.58 mL, 7.5 mmol). The reaction was heated at 65° C. for 29 h before being cooled to room temperature and quenched with sat. aq. NaHCO$_3$ (15 mL). The mixture was extracted with ethyl acetate (50 mL×2). The organic layers were combined, washed with brine (15 mL) and dried over MgSO$_4$. Concentration and purification by chromatography (silica gel, 95:5:0.3 dichloromethane/methanol/conc. NH$_4$OH) gave 0.85 g (66%) of the title compound. MS 880 (M+H)$^+$.

EXAMPLE 2

Carbamic acid, [(2E)-3-[4-(2-pyrimidinyl)phenyl]-2-propenyl]-, (3aS,4R,7R,8S,9S,10R,11R,13R,15R,15aR)-4-ethyltetradecahydro-8-hydroxy-3a,7,9,11,13,15-hexamethyl-2,6,14-trioxo-10-[[3,4,6-trideoxy-3-(dimethylamino)-β-D-xylo-hexopyranosyl]oxy]-2H-oxacyclotetradecino[4,3-d]oxazol-11-yl ester

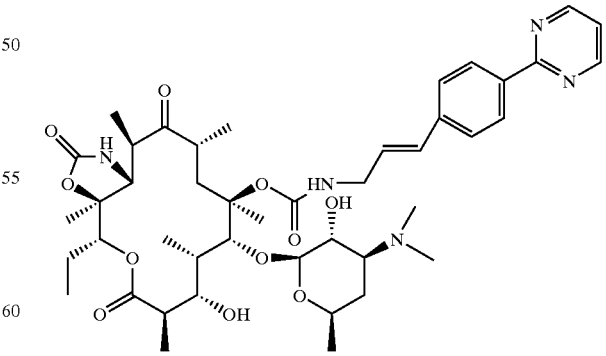

A solution of compound of Example 1 (23 mg, 0.026 mmol) in methanol (5 mL) was stirred at room temperature for 21 h. Concentration and purification by chromatography (silica gel, 92:8:0.3 dichloromethane/methanol/conc. NH4OH) yielded 20 mg (91%) of the title compound. MS 838 (M+H)+

EXAMPLE 3

Compound 1

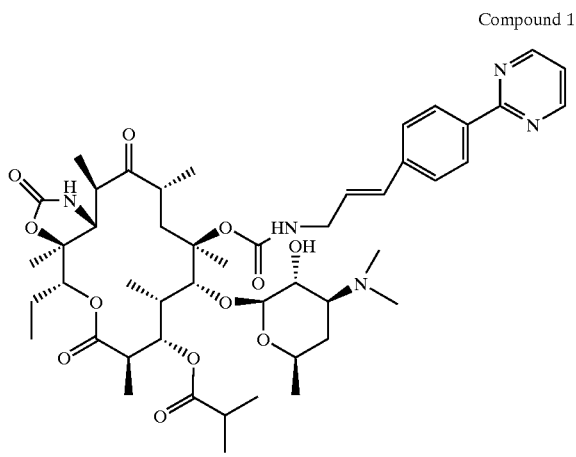

To the solution of compound of Example 1 (100 mg, 0.114 mmol) and catalytic amount of dimethylaminopyridine (DMAP) in CH$_2$Cl$_2$ (2 mL) was added triethylamine (0.15 mL, 1.08 mmol) and isobutyric anhydride (0.1 mL, 0.60 mmol). After the reaction was stirred at room temperature for 24 h, another portion of triethylamine (0.15 mL, 1.08 mmol) and isobutyric anhydride (0.1 mL, 0.60 mmol) was added. The reaction was kept at room temperature for additional 72 h before being diluted with ethyl acetate (50 mL). The organic solution was washed sequentially with sat. aq. NH$_4$Cl, sat. aq. NaHCO$_3$ and brine, dried over MgSO$_4$ and concentrated. The resulting crude product was stirred in methanol (5 mL) at room temperature for 16 h. Potassium carbonate powder (0.1 g) was added to the solution and the reaction was stirred for another 1 h. The mixture was then diluted with ethyl acetate (50 mL). The organic solution was washed with H$_2$O (5 mL) and brine (5 mL), dried over MgSO$_4$ and concentrated. Purification by chromatography (silica gel, 95:5:0.3 dichloromethane/methanol/conc. NH$_4$OH) gave 60 mg (58%) of the title compound. MS 908 (M+H)+

EXAMPLE 4

Compound 2

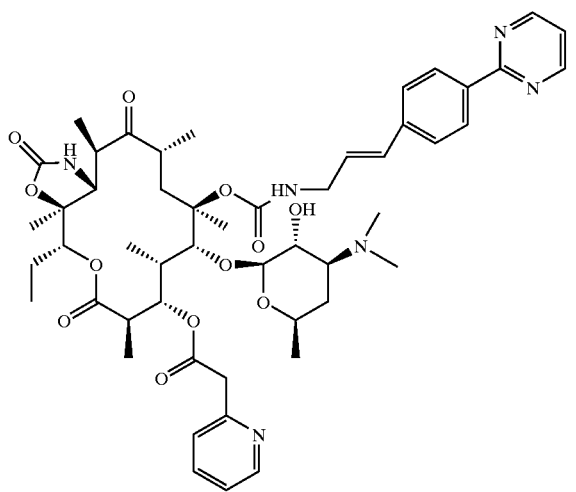

To the solution of compound of Example 1 (45 mg, 0.051 mmol), catalytic amount of dimethylaminopyridine and 2-pyridylacetic acid hydrochloride (44 mg, 0.25 mmol) in CH$_2$Cl$_2$ (2 mL) was added triethylamine (0.05 mL, 0.36 mmol) and 1,3-dicyclohexylcarbodiimide (DCC, 85 mg, 0.41 mmol). The reaction was stirred at room temperature for 16 h before being diluted with sat. aq. NaHCO$_3$ (10 mL). The mixture was extracted with ethyl acetate (30 mL×2). The organic solution was washed with sat. aq. NaCl, dried over MgSO$_4$, and concentrated. The resulting crude product was stirred in methanol (5 mL) at room temperature for 16 h. Concentration and purification by chromatography (silica gel, 92:8:0.3 dichloromethane/methanol/conc. NH$_4$OH) yielded 20 mg (41%) of the title compound. MS 957 (M+H)+.

EXAMPLE 5

Compound 3

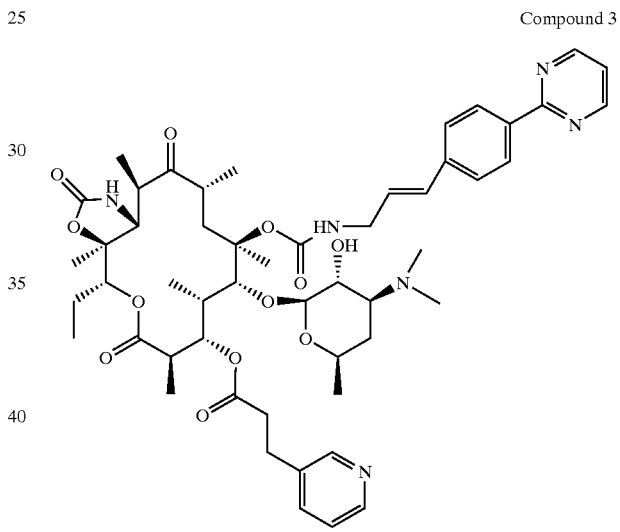

To the solution of compound of Example 1 (90 mg, 0.1 mmol), catalytic amount of dimethylaminopyridine and 3-pyridinepropionic acid (45 mg, 0.3 mmol) in CH$_2$Cl$_2$ (2 mL) was added 1-[3-(dimethylamino)propyl]-3-ethylcarbodiimide hydrochloride (60 mg, 0.3 mmol). The reaction was stirred at room temperature for 16 h before being diluted with ethyl acetate (50 mL). The organic solution was washed with sat. aq. NaHCO$_3$ (5 mL), sat. aq. NaCl, dried over MgSO$_4$, and concentrated. The resulting crude product was stirred in methanol (5 mL) for 48 h. Concentration and purification by chromatography (silica gel, 94:6:0.3 dichloromethane/methanol/conc. NH$_4$OH) yielded 25 mg (25%) of the title compound. MS 971 (M+H)+.

EXAMPLE 6

Compound 4

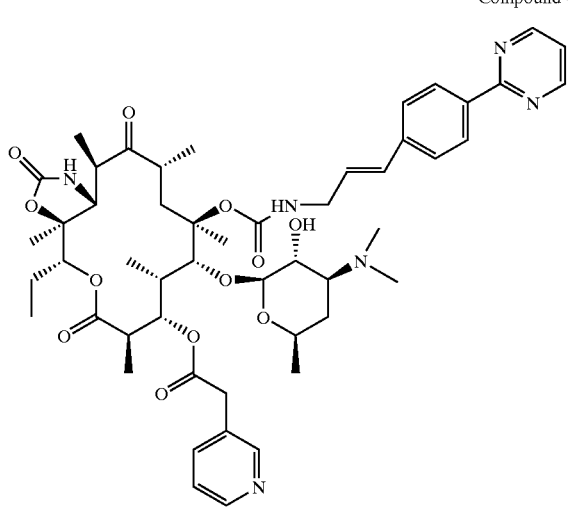

To the solution of compound of Example 1 (90 mg, 0.1 mmol), catalytic amount of dimethyaminopyridine and 3-pyridylacetic acid hydrochloride (35 mg, 0.2 mmol) in $CH_2Cl_2$ (2 mL) was added 1-[3-(dimethylamino)propyl]-3-ethylcarbodiimide hydrochloride (80 mg, 0.42 mmol). The reaction was stirred at room temperature for 24 h before being diluted with ethyl acetate (50 mL). The organic solution was washed with sat. aq. $NaHCO_3$ (5 mL), brine (5 mL), dried over $MgSO_4$, and concentrated. The resulting crude product was stirred in methanol (5 mL) for 24 h. Concentration and purification by chromatography (silica gel, 94:6:0.3 dichloromethane/methanol/conc. $NH_4OH$) yielded 35 mg (36%) of the title compound. MS 957 $(M+H)^+$.

EXAMPLE 7

Compound 5

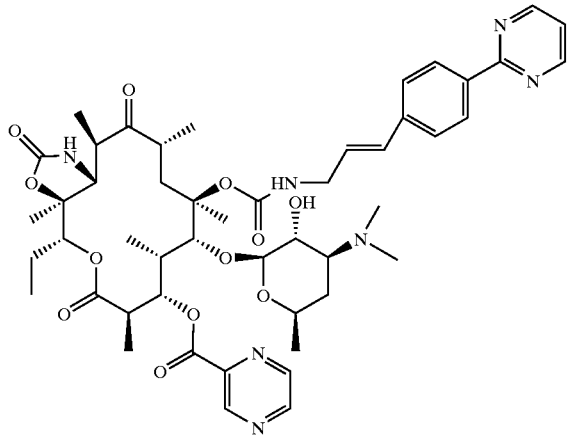

To the solution of compound of Example 1 (90 mg, 0.10 mmol), catalytic amount of dimethylaminopyridine and 2-pyrazinecarboxylic acid (25 mg, 0.20 mmol) in $CH_2Cl_2$ (2 mL) was added 1,3-dicyclohexylcarbodiimide (62 mg, 0.30 mmol). The reaction was stirred at room temperature for 16 h before being diluted with methanol (5 mL) and stirred for another 60 h. The solvent was removed and the resulting residue was dissolved in ethyl acetate (50 mL). The resulting organic solution was washed with sat. aq. $NaHCO_3$ (10 mL) and brine (10 mL), dried over $MgSO_4$, and concentrated. Purification by chromatography (silica gel, 94:6:0.3 dichloromethane/methanol/conc. $NH_4OH$) yielded 60 mg (62%) of the title compound. MS 945 $(M+H)^+$.

EXAMPLE 8

Compound 6

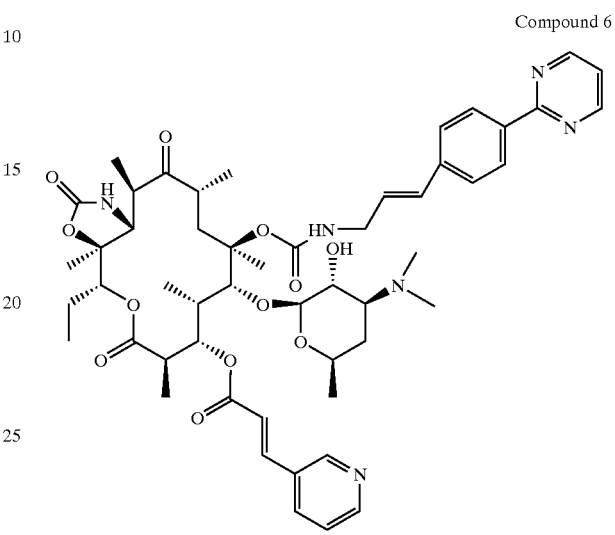

To the solution of compound of Example 1 (90 mg, 0.1 mmol), catalytic amount of dimethylaminopyridine and trans-3-(3-pyridyl)acrylic acid (30 mg, 0.2 mmol) in $CH_2Cl_2$ (2 mL) was added 1,3-dicyclohexylcarbodiimide (82 mg, 0.4 mmol). The reaction was stirred at room temperature for 24 h before being diluted with methanol (5 mL) and stirred for another 60 h. The solvent was then removed and the residue was dissolved in ethyl acetate (50 mL). The resulting organic solution was washed with sat. aq. $NaHCO_3$ and brine, dried over $MgSO_4$, and concentrated. Purification by chromatography (silica gel, 94:6:0.3 dichloromethane/methanol/conc. $NH_4OH$) yielded 40 mg (40%) of the title compound. MS 969 $(M+H)^+$.

EXAMPLE 9

Compound 7

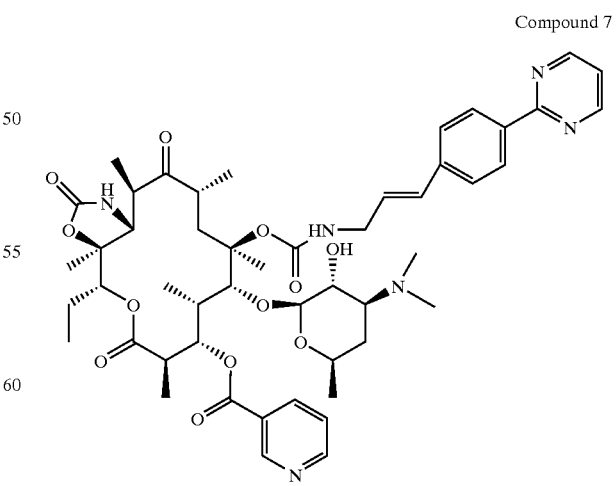

To the solution of compound of Example 1 (95 mg, 0.11 mmol), catalytic amount of dimethylaminopyridine and nicotinic acid (27 mg, 0.22 mmol) in CH₂Cl₂ (2 mL) was added 1,3-dicyclohexylcarbodiimide (90 mg, 0.44 mmol). The reaction was stirred at room temperature for 24 h before being diluted with methanol (5 mL) and stirred for another 24 h. The solvent was then removed and the residue was dissolved in ethyl acetate (50 mL). The resulting organic solution was washed with sat. aq. NaHCO₃ and brine, dried over MgSO₄, and concentrated. Purification by chromatography (silica gel, 94:6:0.3 dichloromethane/methanol/conc. NH₄OH) yielded 27 mg (27%) of the title compound. MS 944 (M+H)⁺.

EXAMPLE 10

Compound 8

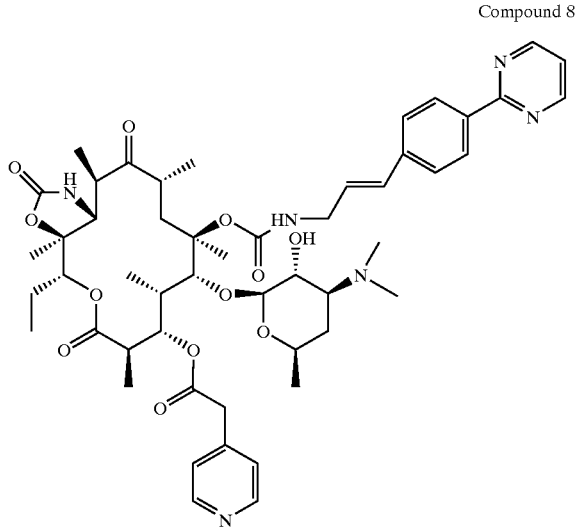

To the solution of compound of Example 1 (110 mg, 0.125 mmol), catalytic amount of dimethylaminopyridine and 4-pyridylacetic acid hydrochloride (44 mg, 0.25 mmol) in CH₂Cl₂ (2 mL) was added triethyl amine (0.05 mL, 0.36 mmol) and 1,3-dicyclohexylcarbodiimide (103 mg, 0.50 mmol). The reaction was stirred at room temperature for 24 h before being diluted with methanol (5 mL) and stirred for another 24 h. The solvent was then removed and the residue was dissolved in ethyl acetate (50 mL). The resulting organic solution was washed with sat. aq. NaHCO₃ and brine, dried over MgSO₄, and concentrated. Purification by chromatography (silica gel, 94:6:0.3 dichloromethane/methanol/conc. NH₄OH) yielded 20 mg (17%) of the title compound. MS 957 (M)⁺.

EXAMPLE 11

Compound 9

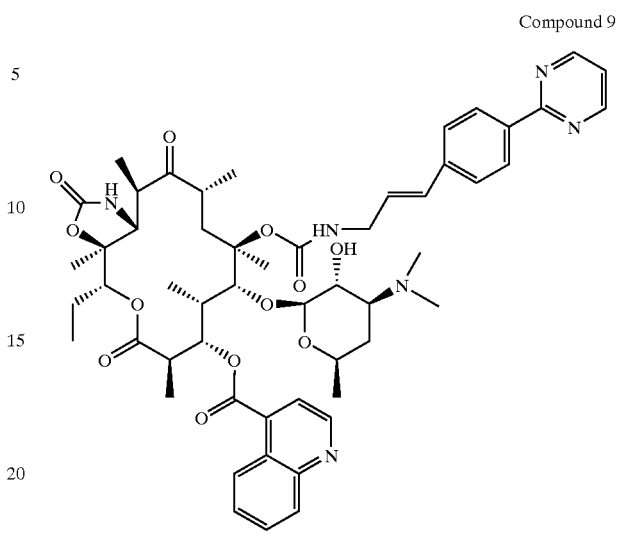

To the solution of compound of Example 1 (120 mg, 0.136 mmol), catalytic amount of dimethylaminopyridine and 4-quinolinecarboxylic acid (50 mg, 0.29 mmol) in CH₂Cl₂ (2 mL) was added 1,3-dicyclohexylcarbodiimide (120 mg, 0.58 mmol). The reaction was stirred at room temperature for 24 h before being diluted with methanol (5 mL) and stirred for another 24 h. The solvent was then removed and the residue was dissolved in ethyl acetate (50 mL). The resulting organic solution was washed with sat. aq. NaHCO₃ and brine, and dried over MgSO₄, and concentrated. Purification by chromatography (silica gel, 94:6:0.3 dichloromethane/methanol/conc. NH₄OH) yielded 43 mg (32%) of the title compound. MS 993 (M+H)⁺.

EXAMPLE 12

Compound 10

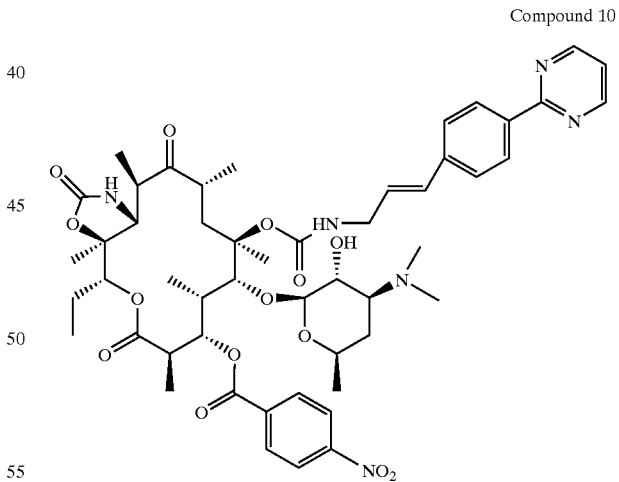

To the solution of compound of Example 1 (95 mg, 0.11 mmol) and catalytic amount of dimethylaminopyridine in CH₂Cl₂ (2 mL) was added triethyl amine (0.09 mL, 0.65 mmol) and 4-nitrobenzoyl chloride (60 mg, 0.33 mmol). The reaction was stirred at room temperature for 16 h before being diluted with methanol (5 mL) and stirred for another 24 h. The solvent was then removed and the residue was dissolved in ethyl acetate (50 mL). The resulting organic solution was washed with sat. aq. NaHCO₃ and brine, dried over MgSO₄, and concentrated. Purification by chromatography (silica gel, 97:3:0.3 dichloromethane/methanol/conc. NH₄OH) yielded 45 mg (42%) of the title compound. MS 987 (M+H)⁺.

EXAMPLE 13

Compound 11

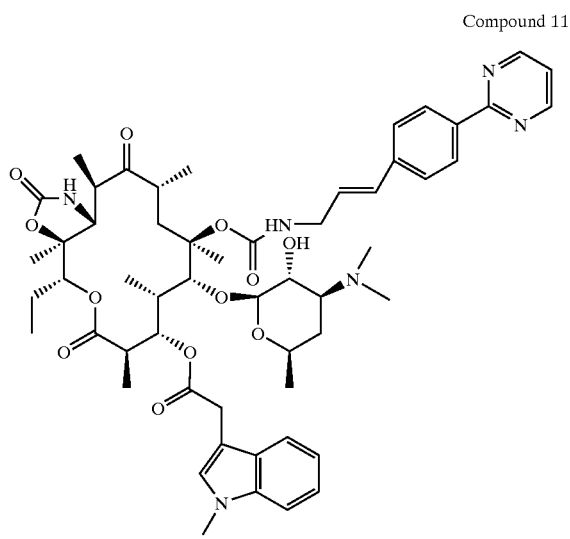

To the solution of compound of Example 1 (90 mg, 0.10 mmol), catalytic amount of dimethylaminopyridine and 1-methyl-3-indoleacetic acid (60 mg, 0.32 mmol) in $CH_2Cl_2$ (2 mL) was added 1,3-dicyclohexylcarbodiimide (135 mg, 0.66 mmol). The reaction was stirred at room temperature for 36 h before being diluted with methanol (5 mL) and stirred for another 16 h. The solvent was then removed and the residue was dissolved in ethyl acetate (50 mL). The resulting organic solution was washed with sat. aq. $NaHCO_3$ and brine, dried over $MgSO_4$, and concentrated. Purification by chromatography (silica gel, 96:4:0.3 dichloromethane/methanol/conc. $NH_4OH$) yielded 46 mg (45%) of the title compound. MS 1009 $(M+H)^+$.

EXAMPLE 14

Compound 12

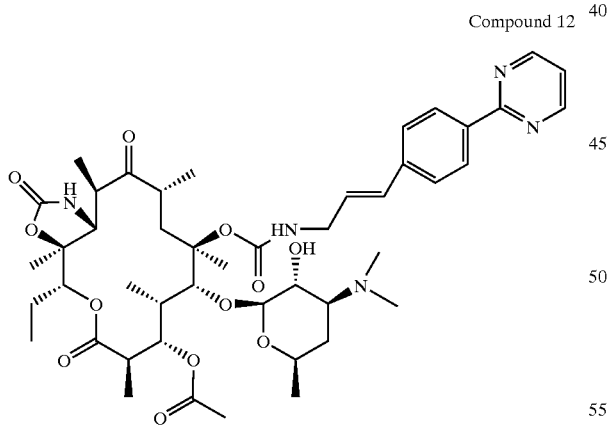

To the solution of compound of Example 1 (90 mg, 0.10 mmol) and catalytic amount of dimethylaminopyridine in $CH_2Cl_2$ (2 mL) was added triethyl amine (0.1 mL, 0.72 mmol) and acetic anhydride (0.05 mL, 0.53 mmol). The reaction was stirred at room temperature for 6 h before being diluted with methanol (5 mL) and stirred for another 16 h. The solvent was then removed and the residue was dissolved in ethyl acetate (50 mL). The resulting organic solution was washed with sat. aq. $NaHCO_3$ and brine, dried over $MgSO_4$, and concentrated. Purification by chromatography (silica gel, 95:5:0.3 dichloromethane/methanol/conc. $NH_4OH$) yielded 38 mg (42%) of the title compound. MS 880 (M+H).

EXAMPLE 15

Compound 13

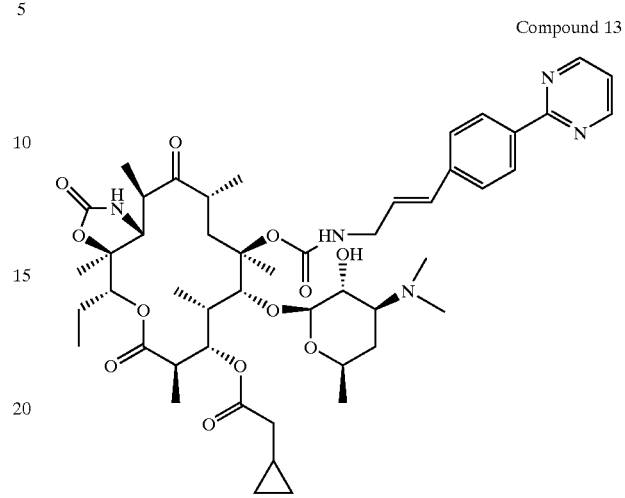

To the solution of compound of Example 1 (95 mg, 0.11 mmol) and catalytic amount of dimethylaminopyridine in $CH_2Cl_2$ (2 mL) was added cyclopropylacetic acid (0.03 mL, 0.30 mmol) and 1,3-dicyclohexylcarbodiimide (110 mg, 0.53 mmol). The reaction was stirred at room temperature for 16 h before being diluted with methanol (5 mL) and stirred for another 72 h. The solvent was then removed and the residue was dissolved in ethyl acetate (50 mL). The resulting organic solution was washed with sat. aq. $NaHCO_3$ and brine, dried over $MgSO_4$, and concentrated. Purification by chromatography (silica gel, 96:4:0.3 dichloromethane/methanol/conc. $NH_4OH$) yielded 50 mg (50%) of the title compound. MS 920 $(M+H)^+$.

EXAMPLE 16

Compound 14

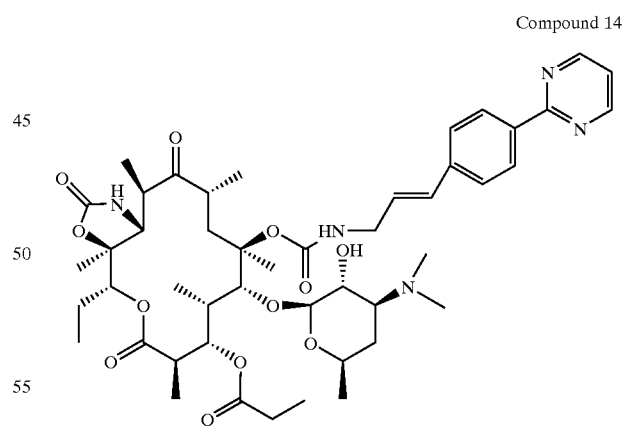

To the solution of compound of Example 1 (88 mg, 0.10 mmol) and catalytic amount of dimethylaminopyridine in $CH_2Cl_2$ (2 mL) was added triethyl amine (0.07 mL, 0.50 mmol) and propionic anhydride (0.04 mL, 0.31 mmol). The reaction was stirred at room temperature for 16 h before being diluted with methanol (5 mL) and stirred for another 16 h. The solvent was then removed and the residue was dissolved in ethyl acetate (50 mL). The resulting organic solution was washed with sat. aq. $NaHCO_3$ and brine, dried over MgSO₄, and concentrated. Purification by chromatography (silica gel, 95:5:0.3 dichloromethane/methanol/conc. NH₄OH) yielded 34 mg (38%) of the title 15 compound. MS 894 (M+H)⁺.

EXAMPLE 17

Compound 15

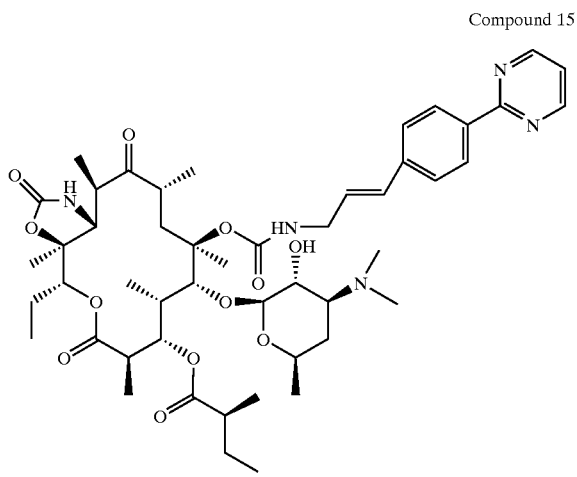

To the solution of compound of Example 1 (70 mg, 0.08 mmol) and catalytic amount of dimethylaminopyridine in CH₂Cl₂ (2 mL) was added triethyl amine (0.11 mL, 0.79 mmol) and (S)-(+)-2-methylbutyric anhydride (0.095 mL, 0.48 mmol). The reaction was stirred at room temperature for 36 h before another portion of triethyl amine (0.11 mL, 0.79 mmol) and (S)-(+)-2-methylbutyric anhydride (0.095 mL, 0.48 mmol) was added. After the reaction was stirred for additional 72 h, it was diluted with methanol (5 mL) and stirred for 20 h. Potassium carbonate (100 mg) was then added to the solution and the reaction was stirred at room temperature for 3 h before being diluted with ethyl acetate (50 mL). The resulting organic solution was washed with H₂O and brine, dried over MgSO₄, and concentrated. Purification by chromatography (silica gel, 96:4:0.3 dichloromethane/methanol/conc. NH₄OH) yielded 32 mg (44%) of the title compound. MS 923 (M+H)⁺.

EXAMPLE 18

Compound 16

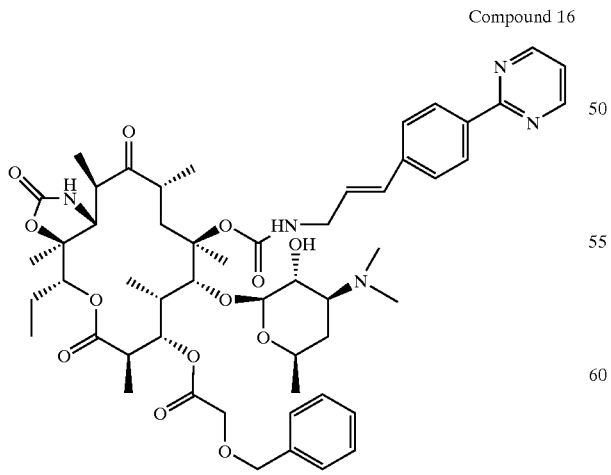

To the solution of compound of Example 1 (50 mg, 0.057 mmol) and catalytic amount of dimethylaminopyridine in CH₂Cl₂ (2 mL) was added benzyloxyacetic acid (0.03 mL, 0.21 mmol) and 1-[3-(dimethylamino)propyl]-3-ethylcarbodiimide hydrochloride (60 mg, 0.31 mmol). The reaction was stirred at room temperature for 24 h before being diluted with ethyl acetate (50 mL). The organic solution was washed with sat. aq. NaHCO₃ (10 mL), sat. aq. NH₄Cl (5 mL), sat. aq. NaHCO₃ (5 mL) and brine (5 mL), and dried over MgSO₄. The solvent was then removed and the residue was dissolved in methanol (5 mL) and stirred for 72 h. Concentration and purification by chromatography (silica gel, 96:4:0.3 dichloromethane/methanol/conc. NH₄OH) yielded 30 mg (54%) of the title compound. MS 987 (M+H)⁺.

EXAMPLE 19

Carbamic acid, [(2E)-3-(3-pyridinyl)-2-propenyl]-, (3aS, 4R,7R,8S,9S,10R,11R,13R,15R,15aR)-10-[[2-O-acetyl-3,4, 6-trideoxy-3-(dimethylamino)-β-D-xylo-hexopyranosyl] oxy]4-ethyltetradecahydro-8-hydroxy-3a,7,9,11,13,15-hexamethyl-2,6,14-trioxo-2H-oxacyclotetradecino[4,3-d] oxazol-11-yl ester

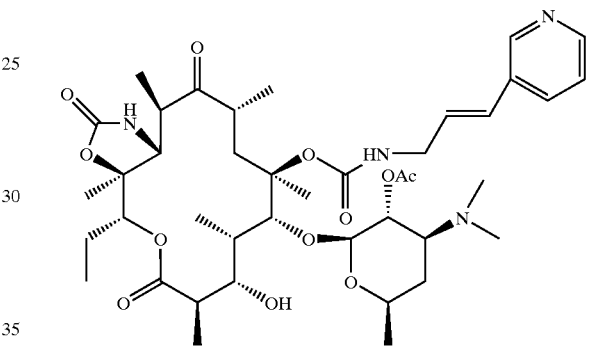

A solution of compound 2H-oxacyclotetradecino[4,3-d] oxazole-2,6,14(1H,7H)-trione, 10-[[2-O-acetyl-3,4,6-trideoxy-3-(dimethylamino)-β-D-xylo-hexopyranosyl]oxy]-11-[(aminocarbonyl)oxy]4-ethyldecahydro-8-hydroxy-3a,7, 9,11,13,15-hexamethyl-, (3aS,4R,7R,8S,9S,10R, 11R,13R, 15R,15aR)-(0.8 g, 1.17 mmol),

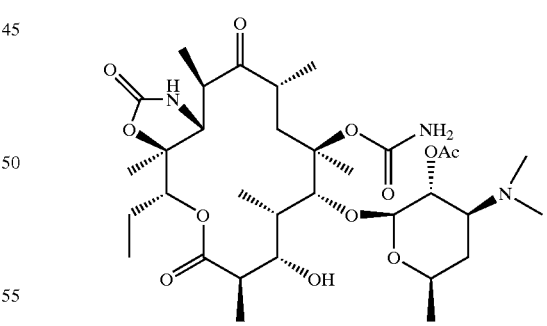

triethylsilane (0.9 mL, 5.63 mmol), trifluoroacetic acid (0.45 mL, 5.84 mmol) and trans-3-(3-pyridyl)propenyl aldehyde (0.37 g, 2.78 mmol) (Reference Example 3) in CH₃CN (6 mL) was heated at 65° C. for 48 h. The reaction was cooled to room temperature and diluted with ethyl acetate (100 mL). The organic solution was washed with sat. aq. NaHCO₃ (15 mL) and brine (15 mL), dried over MgSO₄, and concentrated. Purification by chromatography (silica gel, 94:6:0.3 dichloromethane/methanol/conc. NH₄OH) yielded 0.49 g (52%) of the title compound.

EXAMPLE 20

Compound 17

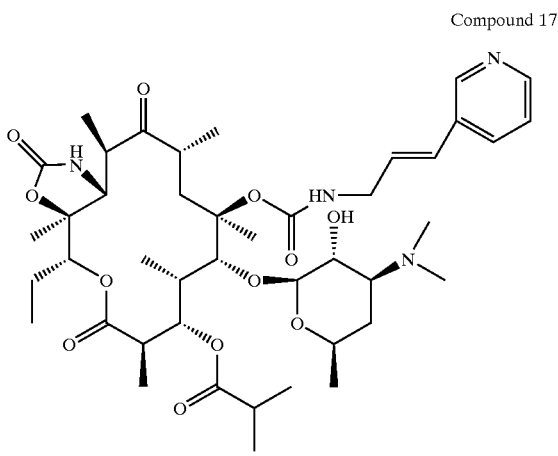

To the solution of compound of Example 19 (92 mg, 0.115 mmol) and catalytic amount of dimethylaminopyridine in CH$_2$Cl$_2$ (2 mL) was added triethyl amine (0.08 mL, 0.58 mmol) and isobutyric anhydride (0.06 mL, 0.36 mmol). The reaction was stirred at room temperature for 72 h before being diluted with methanol (5 mL) and stirred for another 16 h. The solvent was then removed and the residue was dissolved in ethyl acetate (50 mL). The resulting organic solution was washed with sat. aq. NaHCO$_3$ and brine, dried over MgSO$_4$, and concentrated. Purification by chromatography (silica gel, 94:6:0.3 dichloromethane/methanol/conc. NH$_4$OH) yielded 15 mg (16%) of the title compound. MS 831 (M+H)$^+$.

EXAMPLE 21

Compound 18

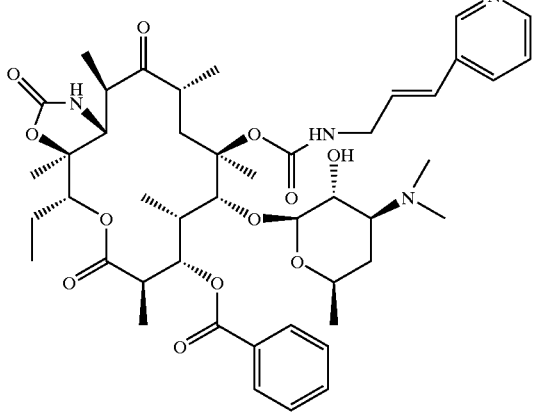

To the solution of compound of Example 19 (89 mg, 0.11 mmol), catalytic amount of dimethylaminopyridine and benzoic acid (30 mg, 0.24 mmol) in CH$_2$Cl$_2$ (2 mL) was added 1,3-dicyclohexylcarbodiimide (90 mg, 0.44 mmol). The reaction was stirred at room temperature for 72 h before being diluted with methanol (5 mL) and stirred for another 16 h. The mixture was diluted with ethyl acetate (50 mL). The resulting organic solution was washed with sat. aq. NH$_4$Cl (5 mL), sat. aq. NaHCO$_3$ (5 mL) and brine (5 mL), dried over MgSO$_4$, and concentrated. Purification by chromatography (silica gel, 94:6:0.3 dichloromethane/methanol/ conc. NH$_4$OH) yielded 15 mg (16%) of the title compound. MS 865 (M+H)$^+$.

EXAMPLE 22

Compound 19

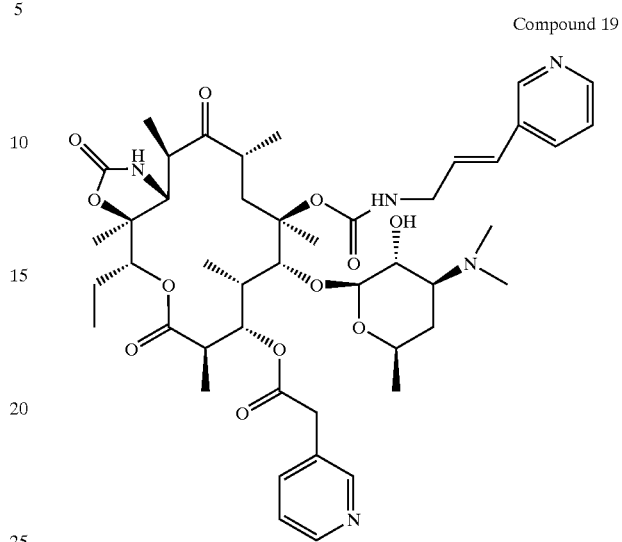

To the solution of compound of Example 19 (90 mg, 0.11 mmol), catalytic amount of dimethylaminopyridine and 3-pyridylacetic acid hydrochloride (80 mg, 0.46 mmol) in CH$_2$Cl$_2$ (2 mL) was added triethyl amine (0.12 mL, 0.86 mmol) and 1,3-dicyclohexylcarbodiimide (180 mg, 0.88 mmol). The reaction was stirred at room temperature for 36 h before being diluted with methanol (5 mL) and stirred for another 16 h. The mixture was diluted with ethyl acetate (50 mL). The resulting organic solution was washed with sat. aq. NH$_4$Cl (5 mL), sat. aq. NaHCO$_3$ (5 mL) and brine (5 mL), dried over MgSO$_4$, and concentrated. Purification by chromatography (silica gel, 94:6:0.3 dichloromethane/methanol/ conc. NH$_4$OH) yielded 20 mg (20%) of the title compound. MS 881 (M+H)$^+$.

EXAMPLE 23

Compound 20

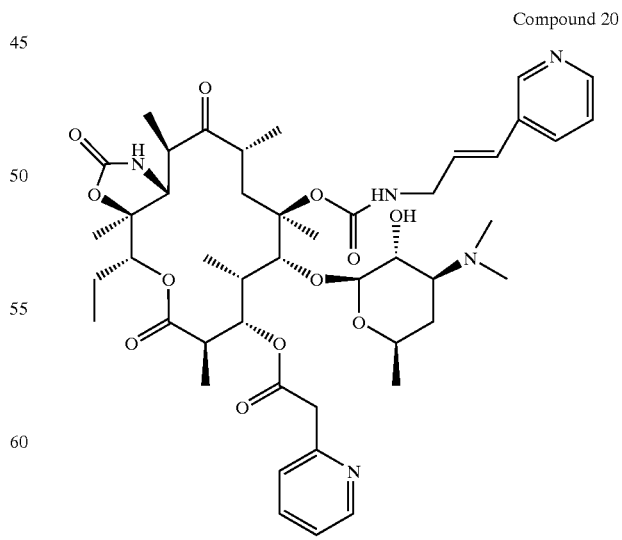

To the solution of compound of Example 19 (90 mg, 0.11 mmol), catalytic amount of dimethylaminopyridine and 2-pyridylacetic acid hydrochloride (40 mg, 0.23 mmol) in CH$_2$Cl$_2$ (2 mL) was added triethyl amine (0.05 mL, 0.36 mmol) and 1,3-dicyclohexylcarbodiimide (90 mg, 0.44 mmol). The reaction was stirred at room temperature for 18 h before being diluted with ethyl acetate (50 mL). The resulting organic solution was washed with sat. aq. NH$_4$Cl (5 mL), sat. aq. NaHCO$_3$ (5 mL) and brine (5 mL), dried over MgSO$_4$, and concentrated. The crude product was dissolved in methanol (5 mL) and stirred for 16 h. Concentration and purification by chromatography (silica gel, 94:6:0.3 dichloromethane/methanol/conc. NH$_4$OH) yielded 50 mg (51%) of the title compound. MS 881 (M+H)$^+$.

EXAMPLE 24

Carbamic acid, [(2E)-3-phenyl-2-propenyl]-, (3aS, 4R,7R,8S,9S,10R,11R,13R,15R,15aR)-10-[[2-O-acetyl-3,4,6-trideoxy-3-(dimethylamino)-β-D-xylo-hexopyranosyl]oxy]4-ethyltetradecahydro-8-hydroxy-3a,7,9,11,13,15-hexamethyl-2,6,14-trioxo-2H-oxacyclotetradecino[4,3-d]oxazol-11-yl ester

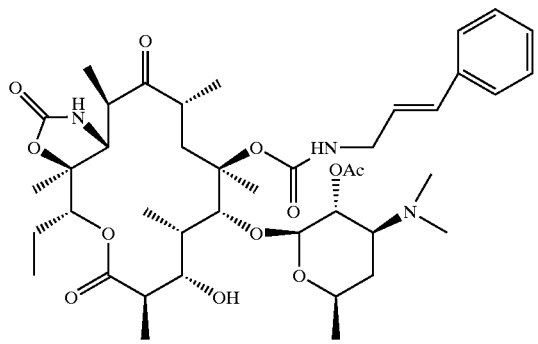

A solution of compound 2H-oxacyclotetradecino[4,3-d]oxazole-2,6,14(1H,7H)-trione, 10-[[2-O-acetyl-3,4,6-trideoxy-3-(dimethylamino)-β-D-xylo-hexopyranosyl]oxy]-11-[(aminocarbonyl)oxy]-4-ethyldecahydro-8-hydroxy-3a,7,9,11,13,15-hexamethyl-, (3aS,4R,7R,8S,9S,10R,11R,13R,15R,15aR)-(0.9 g, 1.31 mmol),

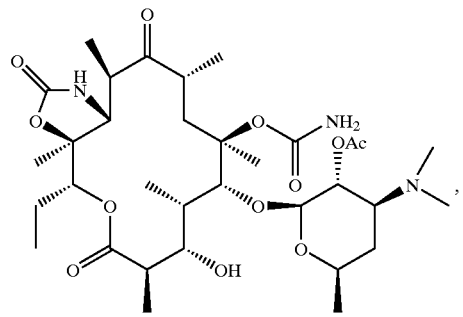

triethylsilane (1.05 mL, 6.6 mmol), trifluoroacetic acid (0.5 mL, 6.5 mmol) and trans-cinnamaldehyde (0.5 mL, 4.0 mmol) in CH$_3$CN (7 mL) was heated at 65° C. for 8 h. The reaction was cooled to room temperature and diluted with ethyl acetate (100 mL). The organic solution was washed with sat. aq. NaHCO$_3$ (15 mL) and brine (15 mL), dried over MgSO$_4$, and concentrated. Purification by chromatography (silica gel, 95:5:0.3 dichloromethane/methanol/conc. NH$_4$OH) yielded 0.47 g (45%) of the title compound.

EXAMPLE 25

Compound 21

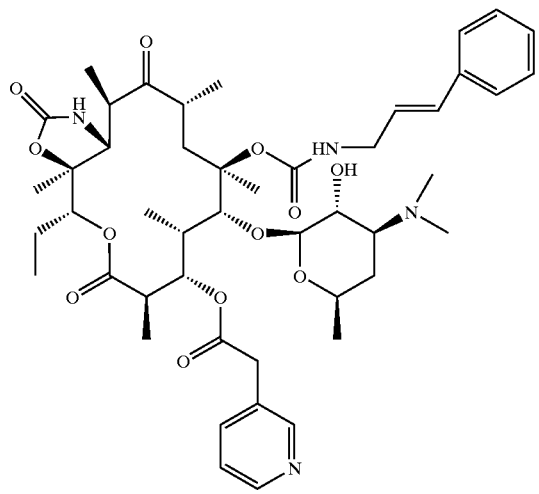

To the solution of compound of Example 24 (88 mg, 0.11 mmol), catalytic amount of dimethylaminopyridine and 3-pyridylacetic acid hydrochloride (80 mg, 0.46 mmol) in CH$_2$Cl$_2$ (2 mL) was added triethyl amine (0.12 mL, 0.86 mmol) and 1,3-dicyclohexylcarbodiimide (180 mg, 0.88 mmol). The reaction was stirred at room temperature for 36 h before being diluted with methanol (5 mL) and stirred for another 16 h. The mixture was diluted with ethyl acetate (50 mL). The resulting organic solution was washed with sat. aq. NH$_4$Cl (5 mL), sat. aq. NaHCO$_3$ (5 mL) and brine (5 mL), dried over MgSO$_4$, and concentrated. Purification by chromatography (silica gel, 94:6:0.3 dichloromethane/methanol/conc. NH$_4$OH) yielded 20 mg (21%) of the title compound. MS 879 (M+H)$^+$.

EXAMPLE 26

Carbamic acid, (3-quinolinylmethyl)-, (3aS,4R,7R, 8S,9S,10R,11R,13R,15R,15aR)-10-[[2-O-acetyl-3,4, 6-trideoxy-3-(dimethylamino)-β-D-xylo-hexopyranosyl]oxy]4-ethyltetradecahydro-8-hydroxy-3a,7,9,11,13,15-hexamethyl-2,6,14-trioxo-2H-oxacyclotetradecino[4,3-d]oxazol-11-yl ester

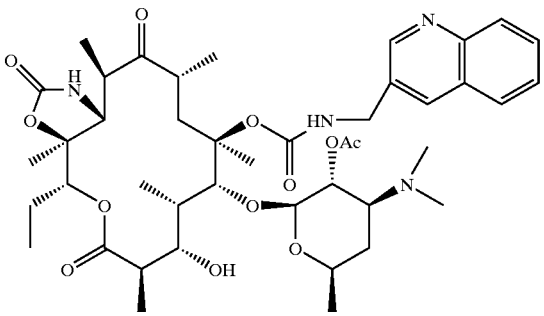

A solution of compound 2H-oxacyclotetradecino[4,3-d]oxazole-2,6,14(1H,7H)-trione, 10-[[2-O-acetyl-3,4,6-trideoxy-3-(dimethylamino)-β-D-xylo-hexopyranosyl]oxy]-11-[(aminocarbonyl)oxy]-4-ethyldecahydro-8-hydroxy-3a,7,9,11,13,15-hexamethyl-, (3aS,4R,7R,8S,9S,10R,11R,13R, 15R,15aR)-(0.9 g, 1.31 mmol),

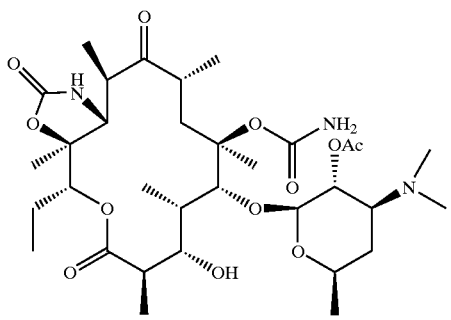

triethylsilane (1.05 mL, 6.6 mmol), trifluoroacetic acid (0.5 mL, 6.5 mmol) and 3-quinolinecarboxaldehyde (0.62 g, 3.94 mmol) in CH$_3$CN (6 mL) was heated at 65° C. for 48 h. The reaction was cooled to room temperature and diluted with ethyl acetate (100 mL). The resulting organic solution was washed with sat. aq. NaHCO$_3$ (15 mL) and brine (15 mL), dried over MgSO$_4$, andc concentrated. Purification by chromatography (silica gel, 95:5:0.3 dichloromethane/methanol/conc. NH$_4$OH) yielded 0.30 g (28%) of the title compound.

EXAMPLE 27

Compound 22

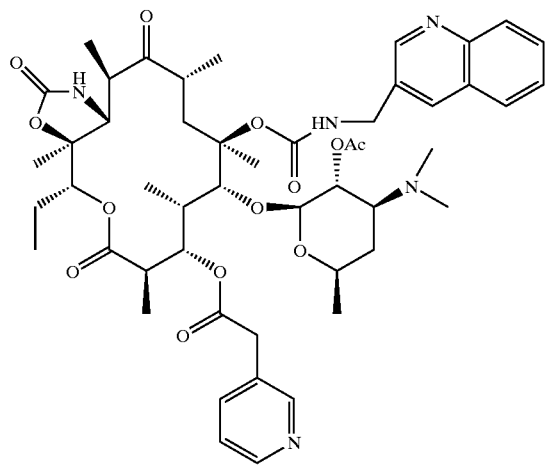

RWJ 424847-300-A
16927-63

To a solution of compound of Example 26 (100 mg, 0.12 mmol), catalytic amount of dimethylaminopyridine and 3-pyridylacetic acid hydrochloride (60 mg, 0.35 mmol) in CH$_2$Cl$_2$ (2 mL) was added 1,3-dicyclohexylcarbodiimide (120 mg, 0.58 mmol). The reaction was stirred at room temperature for 16 h before being diluted with ethyl acetate (50 mL). The organic solution was washed with sat. aq. NH$_4$Cl (5 mL), sat. aq. NaHCO$_3$ (5 mL) and brine (5 mL), dried over MgSO$_4$, and concentrated. The resulting crude product was dissolved in methanol (5 mL) and stirred for 16 h. Concentration and purification by chromatography (silica gel, 94:6:0.3 dichloromethane/methanol/conc. NH$_4$OH) yielded 28 mg (26%) of the title compound. MS 904 (M+H)$^+$.

EXAMPLE 28

Carbamic acid, [(2E,4E)-5-(3-pyridinyl)-2,4-pentadienyl]-, (3aS,4R,7R,8S,9S,10R,11R,13R,15R,15aR)-10-[[2-O-acetyl-3,4,6-trideoxy-3-(dimethylamino)-β-D-xylo-hexopyranosyl]oxy]-4-ethyltetradecahydro-8-hydroxy-3a,7,9,11,13,15-hexamethyl-2,6,14-trioxo-2H-oxacyclotetradecino[4,3-d]oxazol-11-yl ester

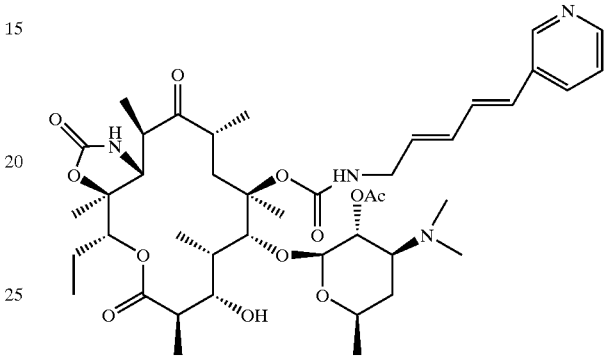

A solution of compound 2H-oxacyclotetradecino[4,3-d]oxazole-2,6,14(1H,7H)-trione, 10-[[2-O-acetyl-3,4,6-trideoxy-3-(dimethylamino)-β-D-xylo-hexopyranosyl]oxy]-11-[(aminocarbonyl)oxy]-4-ethyldecahydro-8-hydroxy-3a,7,9,11,13,15-hexamethyl-, (3aS,4R,7R,8S,9S,10R,11R,13R,15R,15aR)-(0.80 g. 1.17 mmol),

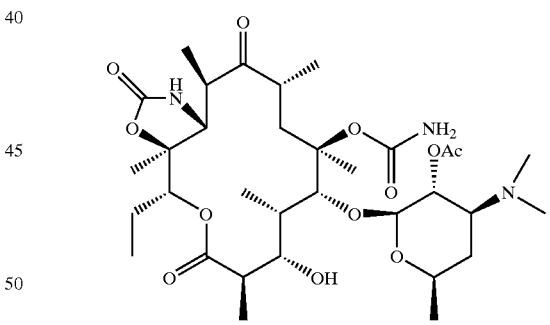

triethylsilane (0.95 mL, 6.0 mmol), trifluoroacetic acid (0.45 mL, 5.9 mmol) and trans, trans-5-(3-pyridyl)-2,4-pentadienyl aldehyde (0.55 g, 3.5 mmol) (Reference Example 4) in CH$_3$CN (6 mL) was heated at 65° C. for 78 h. The reaction was cooled to room temperature and diluted with ethyl acetate (100 mL). The resulting organic solution was washed with sat. aq. NaHCO$_3$ (15 mL) and brine (15 mL), dried over MgSO$_4$, and concentrated. Purification by chromatography (silica gel, 96:4:0.3 dichloromethane/methanol/conc. NH$_4$OH) yielded 0.46 g (48%) of the title compound.

EXAMPLE 29

Compound 23

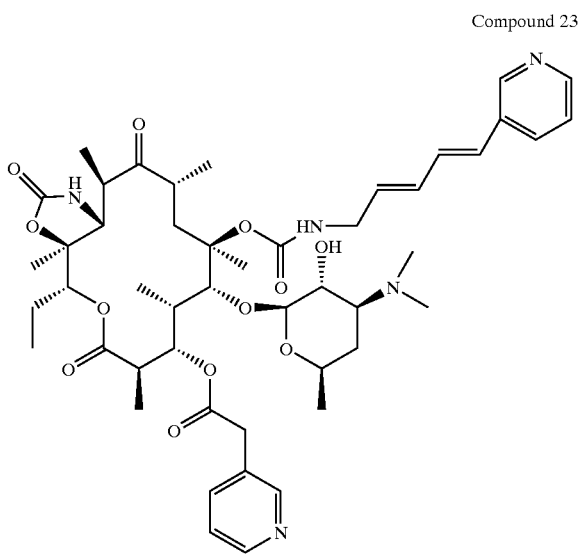

To the solution of compound of Example 28 (54 mg, 0.065 mmol), catalytic amount of dimethylaminopyridine and 3-pyridylacetic acid hydrochloride (20 mg, 0.12 mmol) in $CH_2Cl_2$ (2 mL) was added 1-[3-(dimethylamino)propyl]-3-ethylcarbodiimide hydrochloride (50 mg, 0.26 mmol). The reaction was stirred at room temperature for 5 h before being diluted with ethyl acetate (50 mL). The resulting organic solution was washed with sat. aq. $NH_4Cl$ (5 mL), sat. aq. $NaHCO_3$ (5 mL) and brine (5 mL), dried over $MgSO_4$, and concentrated. The crude product was dissolved in methanol (5 mL) and stirred at room temperature for 24 h. Concentration and purification by chromatography (silica gel, 94:6:0.3 dichloromethane/methanol/conc. $NH_4OH$) yielded 22 mg (37%) of the title compound. MS 906 (M+H)$^+$.

EXAMPLE 30

Compound 24

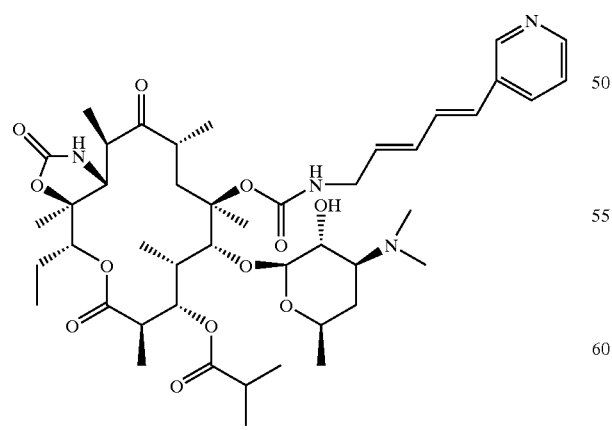

To the solution of compound of Example 28 (85 mg, 0.103 mmol) and catalytic amount of dimethylaminopyridine (DMAP) in $CH_2Cl_2$ (2 mL) was added triehtylamine (0.14 mL, 1.0 mmol) and isobutyric anhydride (0.10 mL, 0.60 mmol). The reaction was stirred at room temperature for 48 h before being diluted with ethyl acetate (50 mL). The resulting organic solution was washed with sat. aq. $NH_4Cl$, sat. aq. $NaHCO_3$ and brine, dried over $MgSO_4$, and concentrated. The crude product was stirred in methanol (5 mL) at room temperature for 16 h. Potassium carbonate powder (0.1 g) was then added to the reaction and the mixture was stirred for another 1 h before being diluted with ethyl acetate (50 mL). The organic solution was washed with $H_2O$ (5 mL) and brine (5 mL), dried over $MgSO_4$, and concentrated. Purification by chromatography (silica gel, 95:5:0.3 dichloromethane/methanol/conc. $NH_4OH$) gave 45 mg (51%) of the title compound. MS 879 (M+Na)$^+$.

EXAMPLE 31

Compound 25

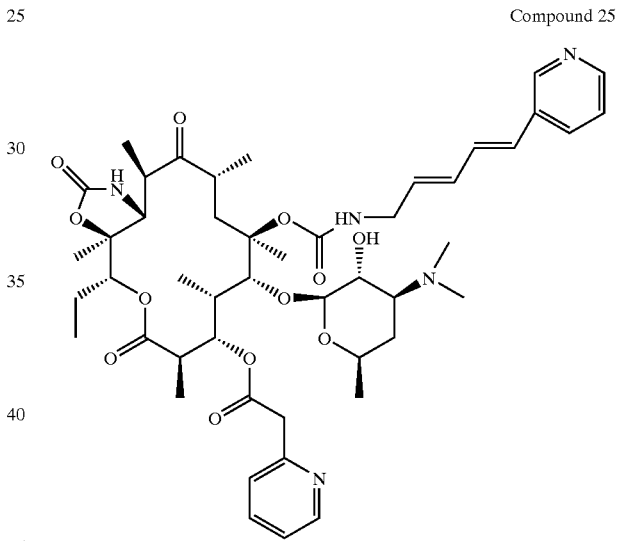

To the solution of compound of Example 28 (85 mg, 0.103 mmol), catalytic amount of dimethylaminopyridine and 2-pyridylacetic acid hydrochloride (40 mg, 0.23 mmol) in $CH_2Cl_2$ (2 mL) was added 1-[3-(dimethylamino)propyl]-3-ethylcarbodiimide hydrochloride (85 mg, 0.44 mmol). The reaction was stirred at room temperature for 16 h before being diluted with ethyl acetate (50 mL). The resulting organic solution was washed was with sat. aq. $NH_4Cl$ (5 mL), sat. aq. $NaHCO_3$ (5 mL) and brine (5 mL), dried over $MgSO_4$, and concentrated. The crude product was dissolved in methanol (5 mL) and stirred at room temperature for 16 h. Concentration and purification by chromatography (silica gel, 94:6:0.3 dichloromethane/methanol/conc. $NH_4OH$) yielded 60 mg (65%) of the title compound. MS 906 (M+H)$^+$.

EXAMPLE 32

Propanoic acid, 2-methyl-, (3aS,4R,7R,8S,9S,10R, 11R,13R,15R,15aR)-11-[(aminocarbonyl)oxy]-4-ethyltetradecahydro-3a,7,9,11,13,15-hexamethyl-2,6,14-trioxo-10-[[3,4,6-trideoxy-3-(dimethylamino)-β-D-xylo-hexopyranosyl]oxy]-2H-oxacyclotetradecino[4,3-d]oxazol-8-yl ester

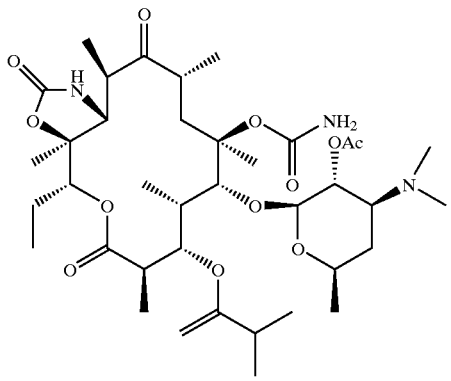

To the solution of compound 2H-oxacyclotetradecino[4,3-d]oxazole-2,6,14(1H,7H)-trione, 10-[[2-O-acetyl-3,4,6-trideoxy-3-(dimethylamino)-β-D-xylo-hexopyranosyl]oxy]-11-[(aminocarbonyl)oxy]4-ethyldecahydro-8-hydroxy-3a,7,9,11,13,15-hexamethyl-, (3aS,4R,7R,8S,9S,10R,11R,13R,15R,15aR)-(500 mg, 0.73 mmol)

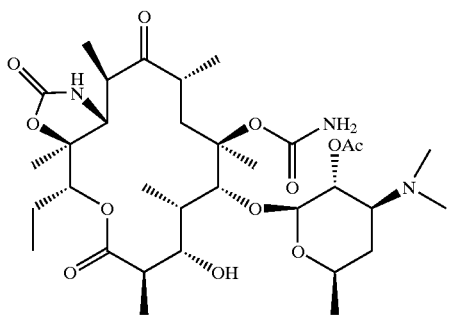

and catalytic amount dimethylaminopyridine (DMAP) in CH₂Cl₂ (2 mL) was added triethylamine (1.0 mL, 7.2 mmol) and isobutyric anhydride (0.73 mL, 4.4 mmol). The reaction was stirred at room temperature for 3 days before another portion of triethylamine (1.0 mL, 7.2 mmol) and isobutyric anhydride (0.73 mL, 4.4 mmol) was added. The reaction was kept at room temperature for another 4 days and was then diluted with ethyl acetate (100 mL). The resulting organic solution was washed with sat. aq. NH₄Cl, sat. aq. NaHCO₃ and brine, dried over MgSO₄ and concentrated. The crude product was stirred with potassium carbonate powder (1.0 g) in methanol (10 mL) at room temperature for 1 h before being diluted with ethyl acetate (100 mL). The organic solution was washed with H₂O (10 mL) and brine (10 mL), dried over MgSO₄ and concentrated. Purification by chromatography (silica gel, 94:6:0.3 dichloromethane/methanol/conc. NH₄OH) gave 0.23 g (42%) of the title compound.

EXAMPLE 33

Compound 26

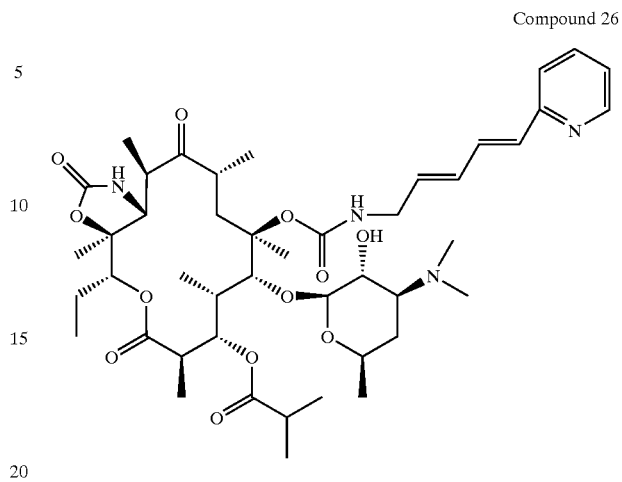

A solution of compound of Example 32 (115 mg, 0.12 mmol), triethylsilane (0.12 mL, 0.75 mmol), trifluoroacetic acid (0.12 mL, 1.56 mmol) and trans, trans-5-(2-pyridyl)-2,4-pentadienyl aldehyde (120 mg, 0.75 mmol) (Reference Example 5) in CH₃CN (2 mL) was heated at 65° C. for 72 h. The reaction was cooled to room temperature and diluted with ethyl acetate (50 mL). The organic solution was washed with sat. aq. NaHCO₃ (5 mL) and brine (5 mL), dried over MgSO₄, and concentrated. The crude product was purified by chromatography (silica gel, 97:3:0.3 dichloromethane/methanol/conc. NH₄OH). The purified compound was then dissolved in MeOH (5 mL) and stirred at room temperature for 72 h. Concentration and purification by chromatography (silica gel, 95:5:0.3 dichloromethane/methanol/conc. NH₄OH) yielded 12 mg (9%) of the title compound. MS 857 (M+H)⁺.

EXAMPLE 34

3-Pyridineacetic acid, (3aS,4R,7R,8S,9S,10R,11R,13R,15R,15aR)-10-[[2-O-acetyl-3,4,6-trideoxy-3-(dimethylamino)-β-D-xylo-hexopyranosyl]oxy]-11-[(aminocarbonyl)oxy]-4-ethyltetradecahydro-3a,7,9,11,13,15-hexamethyl-2,6,14-trioxo-2H-oxacyclotetradecino[4,3-d]oxazol-8-yl ester

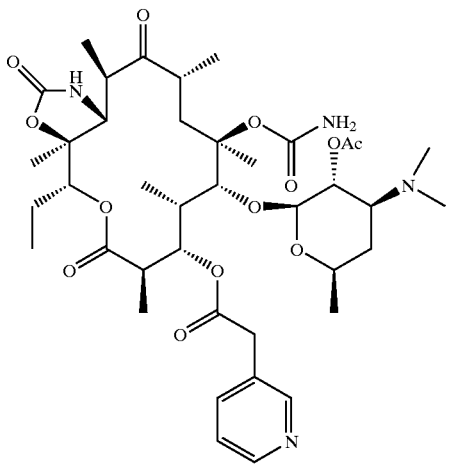

To the solution of compound 2H-oxacyclotetradecino[4,3-d]oxazole-2,6,14(1H,7H)-trione, 10-[[2-O-acetyl-3,4,6- trideoxy-3-(dimethylamino)-β-D-xylo-hexopyranosyl]oxy]-11-[(aminocarbonyl)oxy]4-ethyldecahydro-8-hydroxy-3a,7,9,11,13,15-hexamethyl-, (3aS,4R,7R,8S,9S,10R,11R,13R,15R,15aR)-(500 mg, 0.73 mmol),

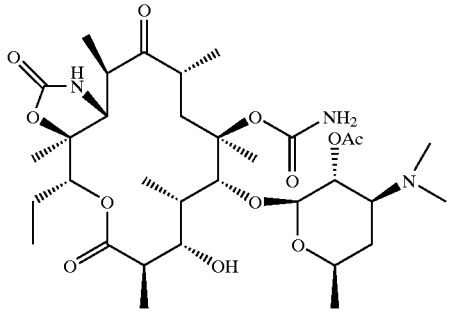

catalytic amount of dimethylaminopyridine and 3-pyridylacetic acid hydrochloride (250 mg, 1.44 mmol) in CH₂Cl₂ (10 mL) was added 1-[3-(dimethylamino)propyl]-3-ethylcarbodiimide hydrochloride (560 mg, 2.92 mmol). The reaction was stirred at room temperature for 16 h before being diluted with ethyl acetate (100 mL). The organic solution was washed with sat. aq. NH₄Cl (10 mL), sat. aq. NaHCO₃ (10 mL) and brine (10 mL), dried over MgSO₄, and concentrated. Purification by chromatography (silica gel, 95:5:0.3 dichloromethane/methanol/conc. NH₄OH) yielded 300 mg (51%) of the title compound.

EXAMPLE 35

Compound 27

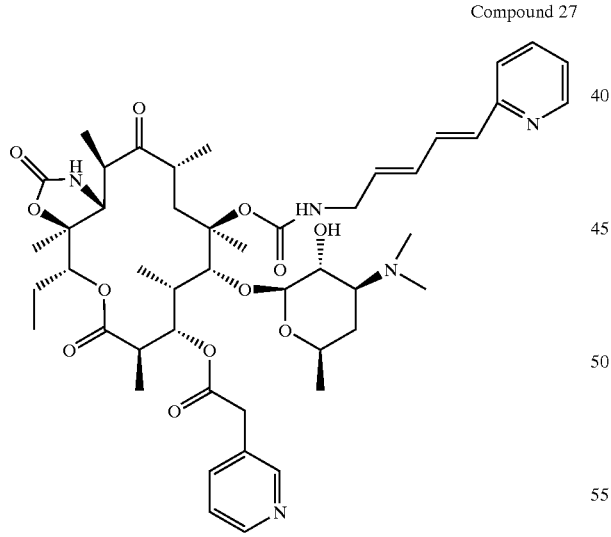

A solution of compound of Example 34 (100 mg, 0.124 mmol), triethylsilane (0.2 mL, 1.26 mmol), trifluoroacetic acid (0.2 mL, 2.60 mmol) and trans, trans-5-(2-pyridyl)-2,4-pentadienyl aldehyde (200 mg, 1.26 mmol) (Reference Example 5) in CH₃CN (2 mL) was heated at 65° C. for 36 h. The reaction was cooled to room temperature and diluted with ethyl acetate (50 mL). The organic solution was washed with sat. aq. NaHCO₃ (5 mL) and brine (5 mL), dried over MgSO₄, and concentrated. The product was purified by chromatography (silica gel, 96:4:0.3 dichloromethane/methanol/conc. NH₄OH). The purified compound was then dissolved in MeOH (5 mL) and stirred at room temperature for 16 h. Concentration and purification by chromatography (silica gel, 93:7:0.3 dichloromethane/methanol/conc. NH₄OH) yielded 45 mg (40%) of the title compound. MS 907 (M+Na)⁺.

EXAMPLE 36

Carbamic acid, [(2E)-3-(6-bromo-3-pyridinyl)-2-propenyl]-, (3aS,4R,7R,8S,9S,10R,11R,13R,15R,15aR)-10-[[2-O-acetyl-3,4,6-trideoxy-3-(dimethylamino)-β-D-xylo-hexopyranosyl]oxy]4-ethyltetradecahydro-8-hydroxy-3a,7,9,11,13,15-hexamethyl-2,6,14-trioxo-2H-oxacyclotetradecino[4,3-d]oxazol-11-yl ester

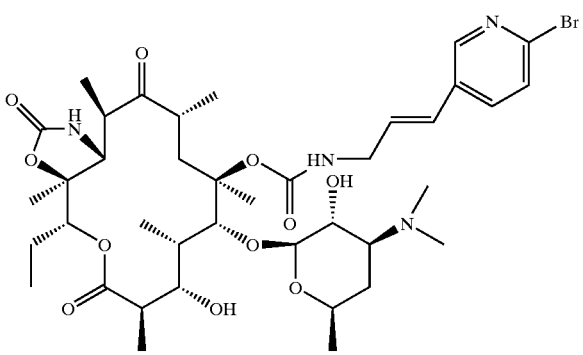

A solution of compound 2H-oxacyclotetradecino[4,3-d]oxazole-2,6,14(1H,7H)-trione, 10-[[2-O-acetyl-3,4,6-trideoxy-3-(dimethylamino)-β-D-xylo-hexopyranosyl]oxy]-11-[(aminocarbonyl)oxy]-4-ethyldecahydro-8-hydroxy-3a,7,9,11,13,15-hexamethyl-, (3aS,4R,7R,8S,9S,10R,11R,13R,15R,15aR)-(0.80 g, 1.17 mmol),

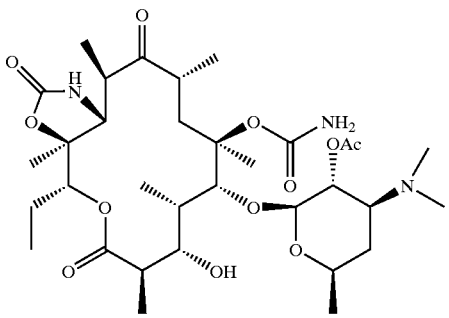

triethylsilane (0.95 mL, 6.0 mmol), trifluoroacetic acid (0.45 mL, 5.9 mmol) and trans-3-[5-(2-bromopyridyl)]propenyl aldehyde (0.75 g, 3.52 mmol) (Reference Example 6) in CH$_3$CN (6 mL) was heated at 65° C. for 16 h. The reaction was cooled to room temperature and diluted with ethylacetate (100 mL). The organic solution was washed with sat. aq. NaHCO$_3$ (15 mL) and brine (15 mL), dried over MgSO$_4$, and concentrated. Purification by chromatography (silica gel, 95:5:0.3 dichloromethane/methanol/conc. NH$_4$OH) yielded 0.55 g (53%) of the title compound.

EXAMPLE 37

Compound 28

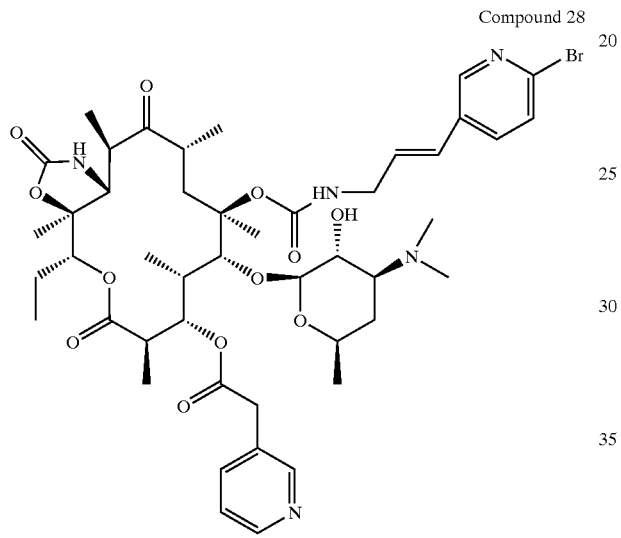

To the solution of compound of Example 36 (95 mg, 0.11 mmol), catalytic amount of dimethylaminopyridine and 3-pyridylacetic acid hydrochloride (37 mg, 0.21 mmol) in CH$_2$Cl$_2$ (2 mL) was added 1-[3-(dimethylamino)propyl]-3-ethylcarbodiimide hydrochloride (85 mg, 0.44 mmol). The reaction was stirred at room temperature for 6 h before being diluted with ethyl acetate (50 mL). The organic solution was washed with sat. aq. NH$_4$Cl (5 mL), sat. aq. NaHCO$_3$ (5 mL) and brine (5 mL), dried over MgSO$_4$, and concentrated. The crude product was dissolved in methanol (5 mL) and stirred at room temperature for 16 h. Concentration and purification by chromatography (silica gel, 95:5:0.3 dichloromethane/methanol/conc. NH$_4$OH) yielded 65 mg (63%) of the title compound. MS 960 (M+H)$^+$.

EXAMPLE 38

Carbamic acid, [(2E)-3-(6-cyano-3-pyridinyl)-2-propenyl]-, (3aS,4R,7R,8S,9S,10R,11R,13R,15R,15aR)-10-[[2-O-acetyl-3,4,6-trideoxy-3-(dimethylamino)-β-D-xylo-hexopyranosyl]oxy]4-ethyltetradecahydro-8-hydroxy-3a,7,9,11,13,15-hexamethyl-2,6,14-trioxo-2H-oxacyclotetradecino[4,3-d]oxazol-11-yl ester

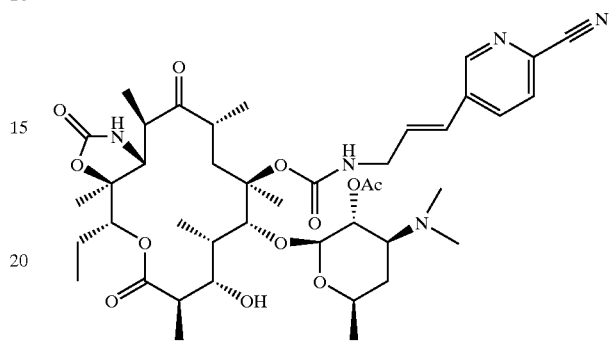

A mixture of compound of Example 36 (300 mg, 0.34 mmol), copper cyanide (185 mg, 2.07 mmol), tetraethylammonium cyanide (105 mg, 0.67 mmol), 1,1'-bis(diphenylphosphino)ferrocene (95 mg, 0.17 mmol) and tris(dibenzylideneacetone)-dipalladium (78 mg, 0.085 mmol) in dioxane (5 mL) was heated to reflux for 4 h. The reaction was cooled to room temperature and diluted with ethyl acetate (50 mL). The mixture was filtered through celite and the solution was washed with sat. aq. NaHCO$_3$ (10 mL×2), dried over MgSO$_4$ and concentrated. Purification by chromatography (silica gel, 95:5:0.3 dichloromethane/methanol/conc. NH$_4$OH) yielded 120 mg (43%) of the title compound.

EXAMPLE 39

Compound 29

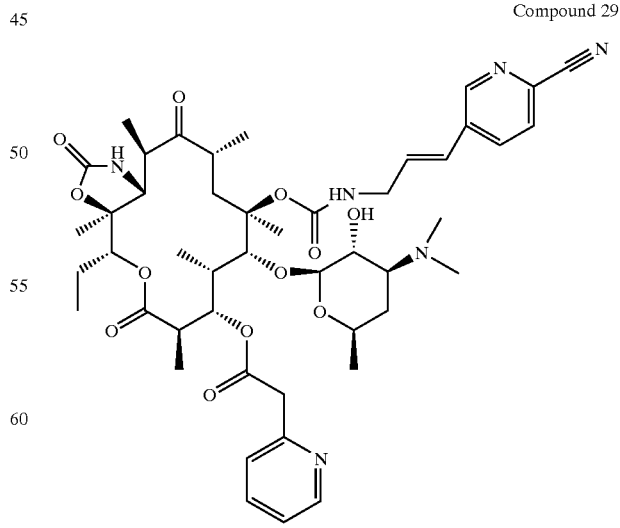

To the solution of compound of Example 38 (40 mg, 0.05 mmol), catalytic amount of dimethylaminopyridine and 2-pyridylacetic acid hydrochloride (18 mg, 0.10 mmol) in CH$_2$Cl$_2$ (2 mL) was added 1-[3-(dimethylamino)propyl]-3-ethylcarbodiimide hydrochloride (50 mg, 0.26 mmol). The reaction was stirred at room temperature for 16 h before being diluted with ethyl acetate (50 mL). The organic solution was washed with sat. aq. NH$_4$Cl (5 mL), sat. aq. NaHCO$_3$ (5 mL) and brine (5 mL), dried over MgSO$_4$, and concentrated. The crude product was dissolved in methanol (5 mL) and stirred at room temperature for 72 h. Concentration and purification by chromatography (silica gel, 95:5:0.3 dichloromethane/methanol/conc. NH$_4$OH) yielded 30 mg (68%) of the title compound. MS 906 (M+H)$^+$.

EXAMPLE 40

Carbamic acid, [(2E)-3-(3-quinolinyl)-2-propenyl]-, (3aS,4R,7R,8S,9S,10R,11R,13R,15R,15aR)-10-[[2-O-acetyl-3,4,6-trideoxy-3-(dimethylamino)-β-D-xylo-hexopyranosyl]oxy]-4-ethyltetradecahydro-8-hydroxy-3a,7,9,11,13,15-hexamethyl-2,6,14-trioxo-2H-oxacyclotetradecino[4,3-d]oxazol-11-yl ester

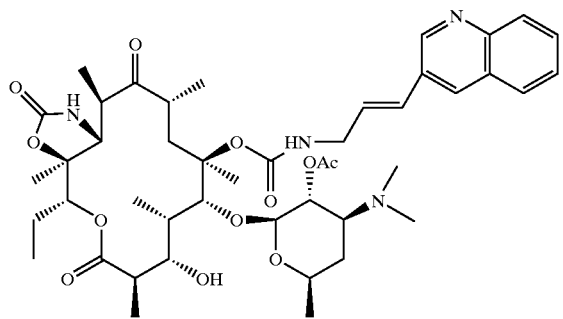

A solution of compound 2H-oxacyclotetradecino[4,3-d]oxazole-2,6,14(1H,7H)-trione, 10-[[2-O-acetyl-3,4,6-trideoxy-3-(dimethylamino)-β-D-xylo-hexopyranosyl]oxy]-11-[(aminocarbonyl)oxy]4-ethyldecahydro-8-hydroxy-3a,7,9,11,13,15-hexamethyl-, (3aS,4R,7R,8S,9S,10R,11R,13R,15R,15aR)-(0.60 g, 0.87 mmol),

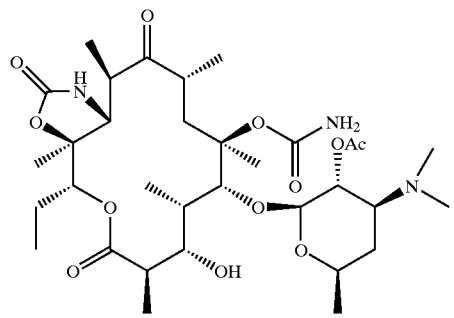

triethylsilane (1.4 mL, 8.8 mmol), trifluoroacetic acid (1.4 mL, 18.2 mmol) and trans-3-(3-quinoline)propenyl aldehyde (0.8 g, 4.4 mmol) (Reference Example 7) in CH$_3$CN (6 mL) was heated at 65° C. for 6 h. The reaction was cooled to room temperature and diluted with ethyl acetate (100 mL). The organic solution was washed with sat. aq. NaHCO$_3$ (15 mL) and brine (15 mL), and dried over MgSO$_4$, and concentrated. Purification by chromatography (silica gel, 94:6:0.3 dichloromethane/methanol/conc. NH$_4$OH) yielded 0.37 g (50%) of the title compound.

EXAMPLE 41

Compound 30

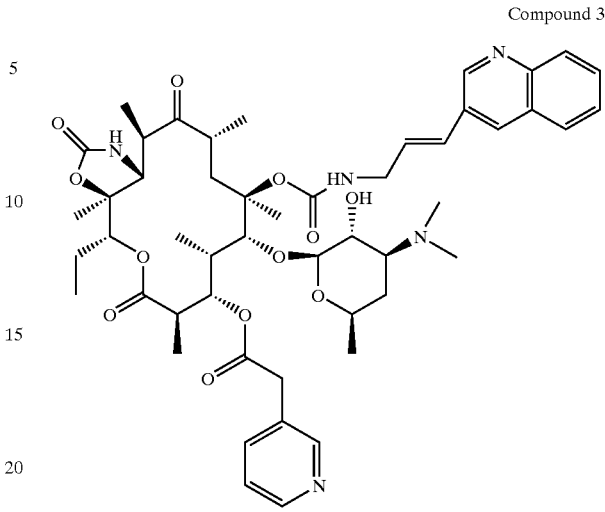

To the solution of compound of Example 40 (35 mg, 0.04 mmol), catalytic amount of dimethylaminopyridine and 3-pyridylacetic acid hydrochloride (15 mg, 0.09 mmol) in CH$_2$Cl$_2$ (2 mL) was added 1,3-dicyclohexylcarbodiimide (50 mg, 0.24 mmol). The reaction was stirred at room temperature for 16 h before being diluted with ethyl acetate (50 mL). The organic solution was washed with sat. aq. NH$_4$Cl (5 mL), sat. aq. NaHCO$_3$ (5 mL) and brine (5 mL), dried over MgSO$_4$, and concentrated. The crude product was dissolved in methanol (5 mL) and stirred at room temperature for 24 h. Concentration and purification by chromatography (silica gel, 95:5:0.3 dichloromethane/methanol/conc. NH$_4$OH) yielded 14 mg (37%) of the title compound. MS 930 (M+H)$^+$.

EXAMPLE 42

Compound 31

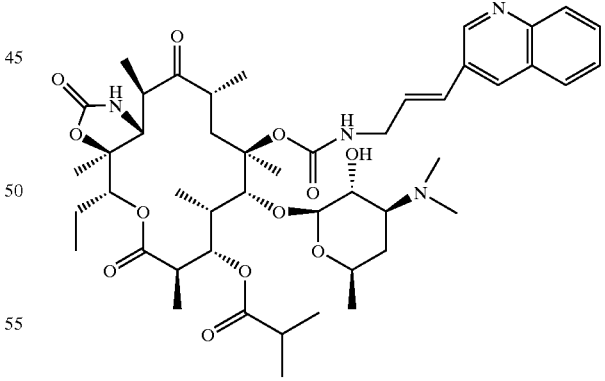

To the solution of compound of Example 40 (90 mg, 0.106 mmol) and catalytic amount of dimethylaminopyridine (DMAP) in CH$_2$Cl$_2$ (2 mL) was added triethylamine (0.24 mL, 1.73 mmol) and isobutyric anhydride (0.18 mL, 1.08 mmol). The reaction was stirred at room temperature for 4 days before being diluted with ethyl acetate (50 mL). The organic solution was washed with sat. aq. NH$_4$Cl, sat. aq. NaHCO$_3$ and brine, dried over MgSO$_4$ and concentrated.

The crude product was dissolved in methanol (5 mL) and stirred at room temperature for 16 h. Potassium carbonate powder (0.1 g) was then added to the solution and the mixture was stirred for another 1.5 h before being diluted with ethyl acetate (50 mL). The resulting organic solution was washed with H₂O (5 mL) and brine (5 mL), dried over MgSO₄ and concentrated. Purification by chromatography (silica gel, 96:4:0.3 dichloromethane/methanol/conc. NH₄OH) gave 47 mg (51%) of the title compound. MS 881 (M+H)⁺.

EXAMPLE 43

Compound 32

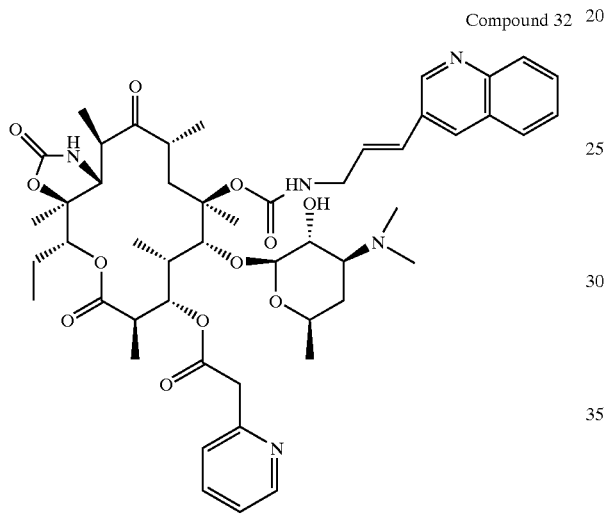

To the solution of compound of Example 40 (75 mg, 0.09 mmol), catalytic amount of dimethylaminopyridine and 2-pyridylacetic acid hydrochloride (30 mg, 0.17 mmol) in CH₂Cl₂ (2 mL) was added 1-[3-(dimethylamino)propyl]-3-ethylcarbodiimide hydrochloride (70 mg, 0.36 mmol). The reaction was stirred at room temperature for 16 h before being diluted with ethyl acetate (50 mL). The organic solution was washed with sat. aq. NH₄Cl (5 mL), sat. aq. NaHCO₃ (5 mL) and brine (5 mL), dried over MgSO₄, and concentrated. The crude product was dissolved in methanol (5 mL) and stirred at room temperature for 20 h. Concentration and purification by chromatography (silica gel, 95:5:0.3 dichloromethane/methanol/conc. NH₄OH) yielded 60 mg (73%) of the title compound. MS 930 (M+H)⁺.

EXAMPLE 44

Carbamic acid, [(2E)-3-(4-quinolinyl)-2-propenyl]-, (3aS,4R,7R,8S,9S,10R,11R,13R,15R,15aR)-10-[[2-O-acetyl-3,4,6-trideoxy-3-(dimethylamino)-β-D-xylo-hexopyranosyl]oxy]-4-ethyltetradecahydro-8-hydroxy-3a,7,9,11,13,15-hexamethyl-2,6,14-trioxo-2H-oxacyclotetradecino[4,3-d]oxazol-11-yl ester

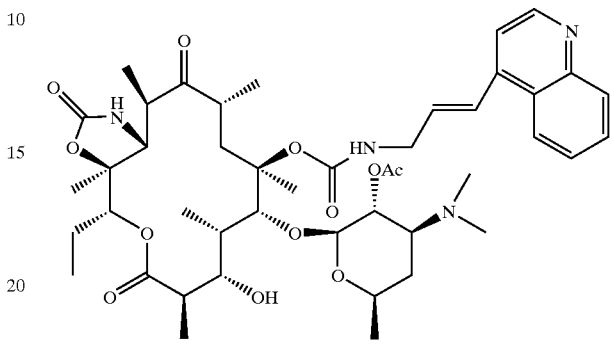

A solution of compound 2H-oxacyclotetradecino[4,3-d]oxazole-2,6,14(1H,7H)-trione, 10-[[2-O-acetyl-3,4,6-trideoxy-3-(dimethylamino)-β-D-xylo-hexopyranosyl]oxy]-11-[(aminocarbonyl)oxy]4-ethyldecahydro-8-hydroxy-3a,7,9,11,13,15-hexamethyl-, (3aS,4R,7R,8S,9S,10R,11R,13R,15R,15aR)-(0.50 g, 0.73 mmol).

Compound 30

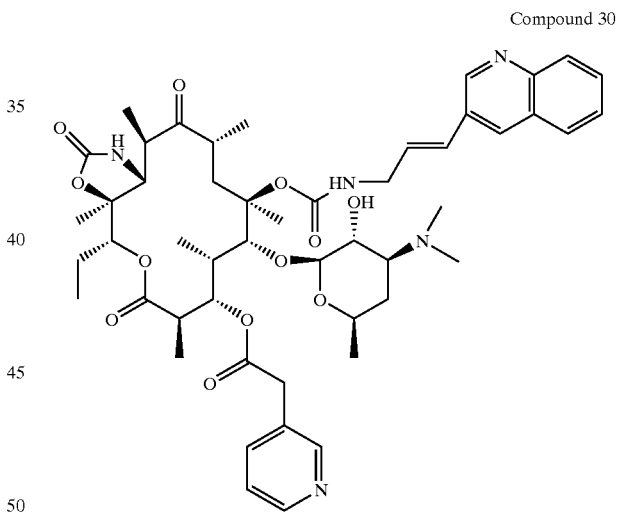

triethylsilane (1.2 mL, 7.5 mmol), trifluoroacetic acid (1.12 mL, 14.5 mmol) and trans-3-(4-quinoline)propenyl aldehyde (0.67 g, 3.66 mmol) (Reference Example 8) in CH₃CN (6 mL) was heated at 65° C. for 7 h. The reaction was cooled to room temperature and diluted with ethyl acetate (100 mL). The organic solution was washed with sat. aq. NaHCO₃ (15 mL) and brine (15 mL), dried over MgSO₄, concentrated. Purification by chromatography (silica gel, 95:5:0.3 dichloromethane/methanol/conc. NH₄OH) yielded 0.30 g (48%) of the title compound.

EXAMPLE 45

Compound 33

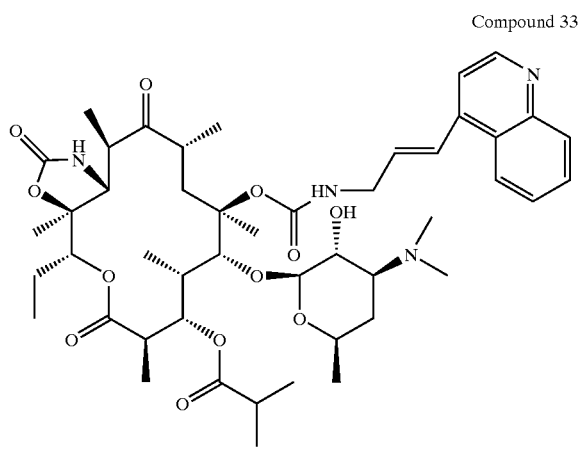

To the solution of compound of Example 44 (75 mg, 0.088 mmol) and catalytic amount of dimethylaminopyridine (DMAP) in $CH_2Cl_2$ (2 mL) was added triethylamine (0.18 mL, 1.30 mmol) and isobutyric anhydride (0.15 mL, 0.90 mmol). The reaction was stirred at room temperature for 72 h before being diluted with ethyl acetate (50 mL). The organic solution was washed with sat. aq. $NH_4Cl$, sat. aq. $NaHCO_3$ and brine, dried over $MgSO_4$ and concentrated. The crude product was dissolved in methanol (5 mL) and stirred at room temperature for 16 h. Potassium carbonate powder (0.1 g) was then added to the solution and the mixture was stirred for another 1.5 h before being diluted with ethyl acetate (50 mL). The organic solution was washed with $H_2O$ (5 mL) and brine (5 mL), dried over $MgSO_4$ and concentrated. Purification by chromatography (silica gel, 95:5:0.3 dichloromethane/methanol/conc. $NH_4OH$) gave 26 mg (34%) of the title compound. MS 881 $(M+H)^+$.

EXAMPLE 46

Compound 34

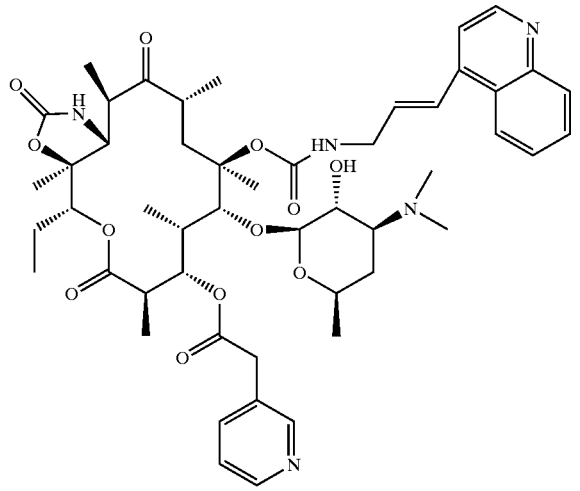

To the solution of compound of Example 44 (75 mg, 0.088 mmol), catalytic amount of dimethylaminopyridine and 3-pyridylacetic acid hydrochloride (31 mg, 0.18 mmol) in $CH_2Cl_2$ (2 mL) was added 1-[3-(dimethylamino)propyl]-3-ethylcarbodiimide hydrochloride (85 mg, 0.44 mmol). The reaction was stirred at room temperature for 16 h before being diluted with ethyl acetate (50 mL). The organic solution was washed with sat. aq. $NaHCO_3$ (5 mL), sat. aq. $NH_4Cl$ (5 mL), sat. aq. $NaHCO_3$ (5 mL) and brine (5 mL), dried over $MgSO_4$, and concentrated. The crude product was dissolved in methanol (5 mL) and stirred for 16 h. Concentration and purification by chromatography (silica gel, 93:7:0.3 dichloromethane/methanol/conc. $NH_4OH$) yielded 40 mg (49%) of the title compound. MS 931 $(M+H)^+$.

EXAMPLE 47

Compound 35

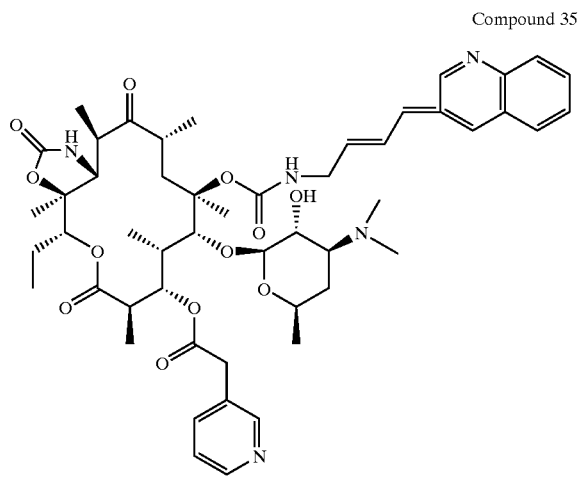

A solution of compound of Example 34 (100 mg, 0.124 mmol), triethylsilane (0.2 mL, 1.25 mmol), trifluoroacetic acid (0.2 mL, 2.60 mmol) and 5-Quinolin-3-yl-penta-2,4-dienal (130 mg, 0.62 mmol) (Reference Example 9) in $CH_3CN$ (2 mL) was heated at 65° C. for 23 h. The reaction was cooled to room temperature and diluted with ethyl acetate (50 mL). The organic solution was washed with sat. aq. $NaHCO_3$ (5 mL) and brine (5 mL), dried over $MgSO_4$ and concentrated. The crude product was dissolved in MeOH (5 mL) and stirred at rt for 24 h. Concentration and purification by chromatography (silica gel, 93:7:0.3 dichloromethane/methanol/conc. $NH_4OH$) yielded 44 mg (37%) of the title compound. MS 979 $(M+Na)^+$.

EXAMPLE 48

Compound 36

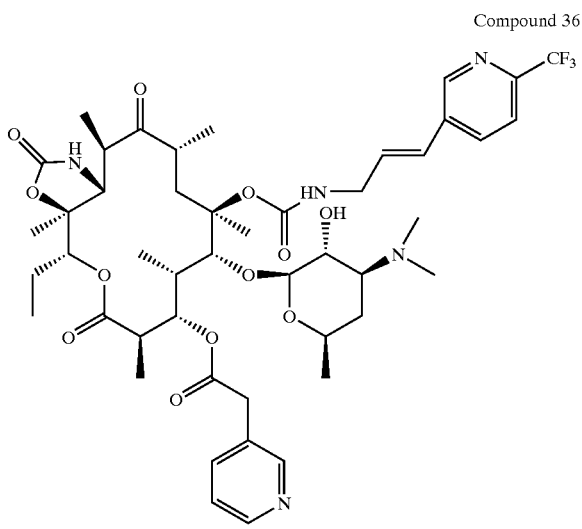

A solution of compound of Example 34 (100 mg, 0.124 mmol), triethylsilane (0.2 mL, 1.25 mmol), trifluoroacetic acid (0.2 mL, 2.60 mmol) and 3-(6-Trifluoromethyl-pyridin-3-yl)-propenal (75 mg, 0.37 mmol) (Reference Example 10) in $CH_3CN$ (2 mL) was heated at 65° C. for 24 h. The reaction was cooled to room temperature and diluted with ethyl acetate (50 mL). The organic solution was washed with sat. aq. $NaHCO_3$ (10 mL) and brine (5 mL), dried over $MgSO_4$ and concentrated. The crude product was dissolved in MeOH (5 mL) and stirred at room temperature for 24 h. Concentration and purification by chromatography (silica gel, 93:7:0.3 dichloromethane/methanol/conc. $NH_4OH$) yielded 51 mg (43%) of the title compound. MS 949 $(M+H)^+$.

EXAMPLE 49

Compound 37

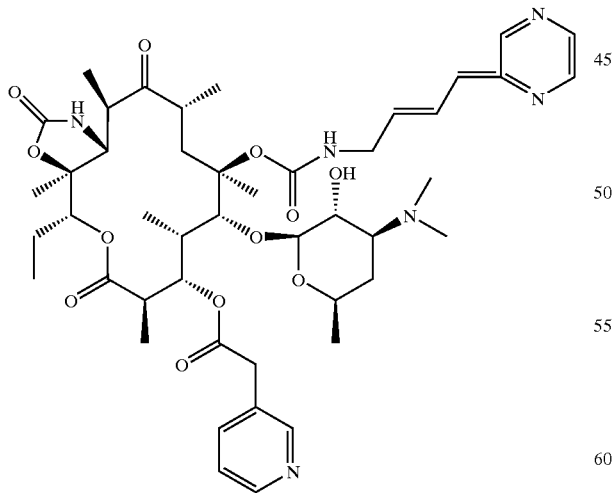

A solution of compound of Example 34 (100 mg, 0.124 mmol), triethylsilane (0.2 mL, 1.25 mmol), trifluoroacetic acid (0.2 mL, 2.60 mmol) and 5-Pyrazin-2-yl-penta-2,4-dienal (80 mg, 0.50 mmol) (Reference Example 11) in $CH_3CN$ (2 mL) was heated at 65° C. for 24 h. The reaction was cooled to room temperature and diluted with ethyl acetate (50 mL). The organic solution was washed with sat. aq. $NaHCO_3$ (10 mL) and brine (5 mL), dried over $MgSO_4$ and concentrated. The crude product was purified by chromatography (silica gel, 95:5:0.3 dichloromethane/methanol/conc. $NH_4OH$). The purified product was dissolved in MeOH (5 mL) and stirred at room temperature for 24 h. Concentration and purification by chromatography (silica gel, 93:7:0.3 dichloromethane/methanol/conc. $NH_4OH$) yielded 45 mg (40%) of the title compound. MS 908 $(M+H)^+$.

EXAMPLE 50

Compound 38

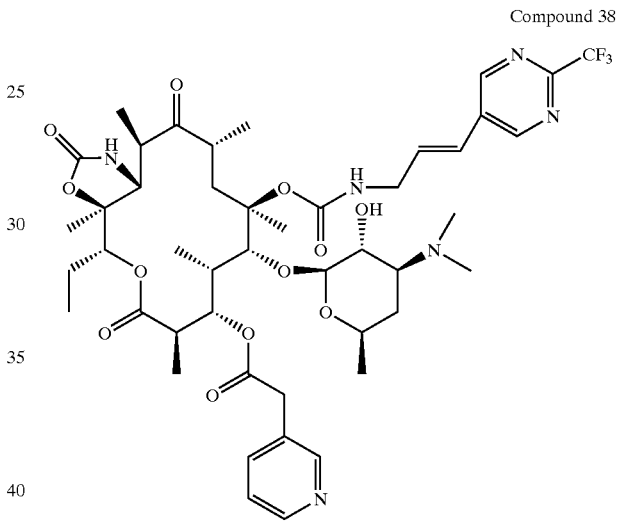

A solution of compound of Example 34 (100 mg, 0.124 mmol), triethylsilane (0.1 mL, 0.62 mmol), trifluoroacetic acid (0.1 mL, 1.30 mmol) and 3-(2-Trifluoromethyl-pyrimidin-5-yl)-propenal (75 mg, 0.37 mmol) (Reference Example 12) in $CH_3CN$ (2 mL) was heated at 65° C. for 28 h. The reaction was cooled to room temperature and diluted with ethyl acetate (50 mL). The organic solution was washed with sat. aq. $NaHCO_3$ (10 mL) and brine (5 mL), dried over $MgSO_4$ and concentrated. The crude product was purified by chromatography (silica gel, 96:4:0.3 dichloromethane/methanol/conc. $NH_4OH$). The purified product was dissolved in MeOH (5 mL) and stirred at room temperature for 72 h. Concentration and purification by chromatography (silica gel, 94:6:0.3 dichloromethane/methanol/conc. $NH_4OH$) yielded 75 mg (64%) of the title compound. MS 949 $(M+H)^+$.

EXAMPLE 51

Compound 39

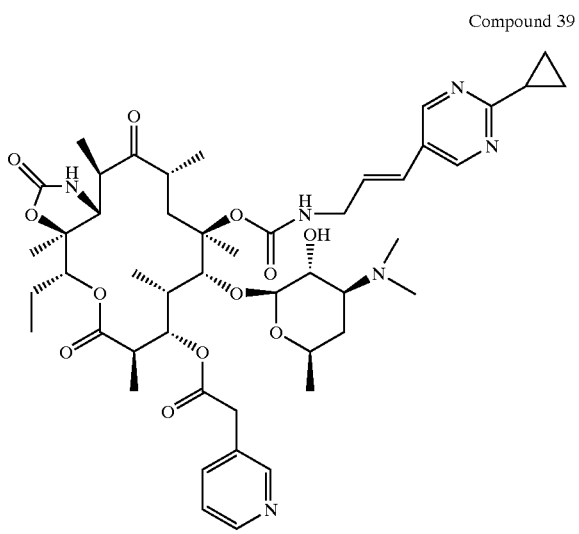

A solution of compound of Example 34 (100 mg, 0.124 mmol), triethylsilane (0.1 mL, 0.62 mmol), trifluoroacetic acid (0.1 mL, 1.30 mmol) and 3-(2-cyclopropyl-pyrimidin-5-yl)-propenal (65 mg, 0.37 mmol) (Reference Example 13) in $CH_3CN$ (2 mL) was heated at 65° C. for 32 h. The reaction was cooled to room temperature and diluted with ethyl acetate (50 mL). The organic solution was washed with sat. aq. $NaHCO_3$ (10 mL) and brine (5 mL), dried over $MgSO_4$ and concentrated. The crude product was purified by chromatography (silica gel, 95:5:0.3 dichloromethane/methanol/conc. $NH_4OH$). The purified product was dissolved in MeOH (5 mL) and stirred at room temperature for 20 h. Concentration and purification by chromatography (silica gel, 94:6:0.3 dichloromethane/methanol/conc. $NH_4OH$) yielded 45 mg (64%) of the title compound. MS 944 $(M+Na)^+$.

EXAMPLE 52

Compound 40

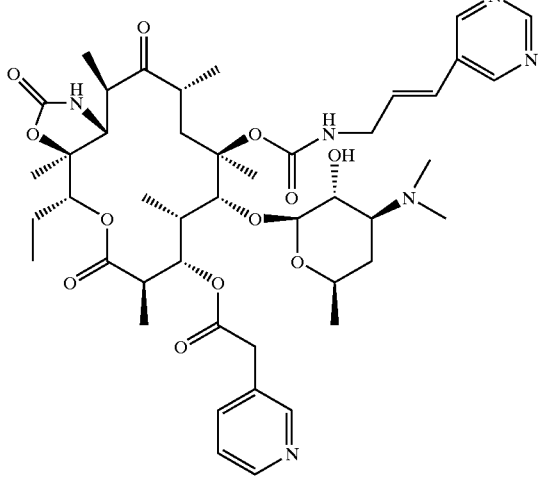

A solution of compound of Example 34 (100 mg, 0.124 mmol), triethylsilane (0.2 mL, 1.25 mmol), trifluoroacetic acid (0.2 mL, 2.60 mmol) and 3-(pyrimidin-5-yl)-propenal (68 mg, 0.51 mmol) (Reference Example 14) in $CH_3CN$ (2 mL) was heated at 65° C. for 49 h. The reaction was cooled to room temperature and diluted with ethyl acetate (50 mL). The organic solution was washed with sat. aq. $NaHCO_3$ (10 mL) and brine (5 mL), dried over $MgSO_4$ and concentrated. The crude product was purified by chromatography (silica gel, 96:4:0.3 dichloromethane/methanol/conc. $NH_4OH$). The purified product was dissolved in MeOH (5 mL) and stirred at room temperature for 72 h. Concentration and purification by chromatography (silica gel, 94:6:0.3 dichloromethane/methanol/conc. $NH_4OH$) yielded 18 mg (16%) of the title compound. MS 882 $(M+H)^+$.

EXAMPLE 53

Compound 41

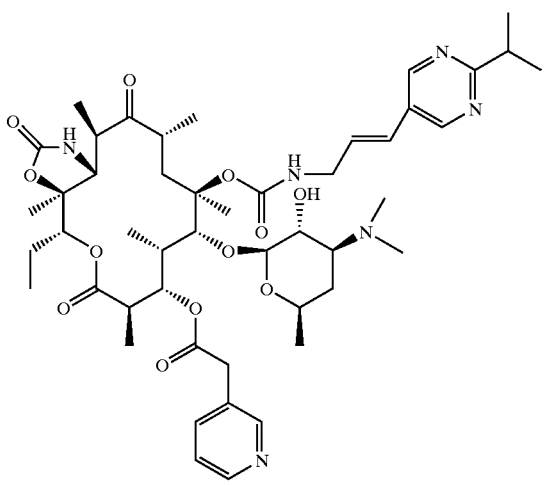

A solution of compound of Example 34 (100 mg, 0.124 mmol), triethylsilane (0.1 mL, 0.62 mmol), trifluoroacetic acid (0.15 mL, 1.95 mmol) and 3-(2-isopropyl-pyrimidin-5-yl)-propenal (65 mg, 0.37 mmol) (Reference Example 15) in $CH_3CN$ (2 mL) was heated at 65° C. for 51 h. The reaction was cooled to room temperature and diluted with ethyl acetate (50 mL). The organic solution was washed with sat. aq. $NaHCO_3$ (10 mL) and brine (5 mL), dried over $MgSO_4$ and concentrated. The crude product was purified by chromatography (silica gel, 95:5:0.3 dichloromethane/methanol/conc. $NH_4OH$). The purified product was dissolved in MeOH (5 mL) and stirred at room temperature for 72 h. Concentration and purification by chromatography (silica gel, 94:6:0.3 dichloromethane/methanol/conc. $NH_4OH$) yielded 25 mg (22%) of the title compound. MS 924 $(M+H)^+$.

EXAMPLE 54

Compound 42

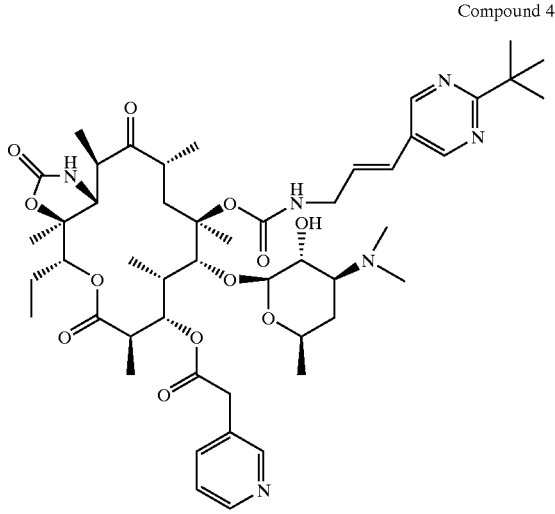

A solution of compound of Example 34 (100 mg, 0.124 mmol), triethylsilane (0.1 mL, 0.62 mmol), trifluoroacetic acid (0.15 mL, 1.95 mmol) and 3-(2-tert-butyl-pyrimidin-5-yl)-propenal (70 mg, 0.37 mmol) (Reference Example 16) in CH$_3$CN (2 mL) was heated at 65° C. for 51 h. The reaction was cooled to room temperature and diluted with ethyl acetate (50 mL). The organic solution was washed with sat. aq. NaHCO$_3$ (10 mL) and brine (5 mL), dried over MgSO$_4$, and concentrated. The crude product was purified by chromatography (silica gel, 95:5:0.3 dichloromethane/methanol/conc. NH$_4$OH). The purified product was dissolved in MeOH (5 mL) and stirred at room temperature for 72 h. Concentration and purification by chromatography (silica gel, 93:7:0.3 dichloromethane/methanol/conc. NH$_4$OH) yielded 28 mg (24%) of the title compound. MS 938 (M+H)$^+$.

EXAMPLE 55

Compound 43

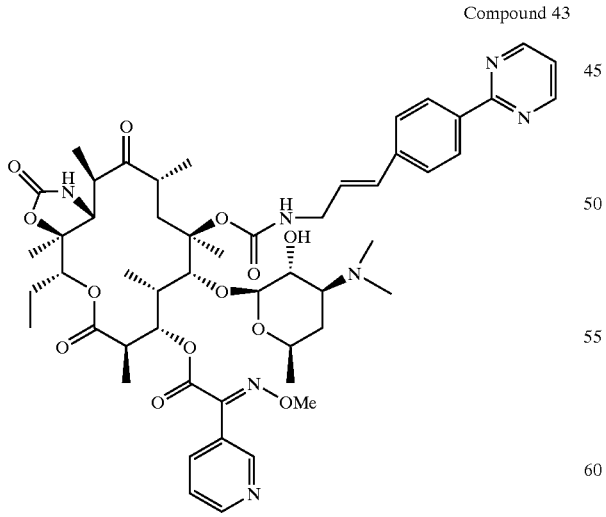

To the solution of compound of Example 1 (85 mg, 0.097 mmol), catalytic amount of dimethylaminopyridine and methoxyimino-pyridin-3-yl-acetic acid (50 mg, 0.23 mmol) in CH$_2$Cl$_2$ (2 mL) was added 1,3-dicyclohexylcarbodiimide (80 mg, 0.39 mmol). The reaction was stirred at room temperature for 24 h before being diluted with ethyl acetate (50 mL). The organic solution was washed with sat. aq. NaHCO$_3$ (5 mL), sat. aq. NH$_4$Cl (5 mL), sat. aq. NaHCO$_3$ (5 mL) and brine (5 mL), dried over MgSO$_4$, and concentrated. The crude product was purified by chromatography (silica gel, 95:5:0.3 dichloromethane/methanol/conc. NH$_4$OH). The purified product was dissolved in methanol (5 mL) and stirred at room temperature for 16 h. Concentration and purification by chromatography (silica gel, 94:6:0.3 dichloromethane/methanol/conc. NH$_4$OH) yielded 31 mg (32%) of the title compound. MS 1023 (M+Na)$^+$.

EXAMPLE 56

Compound 44

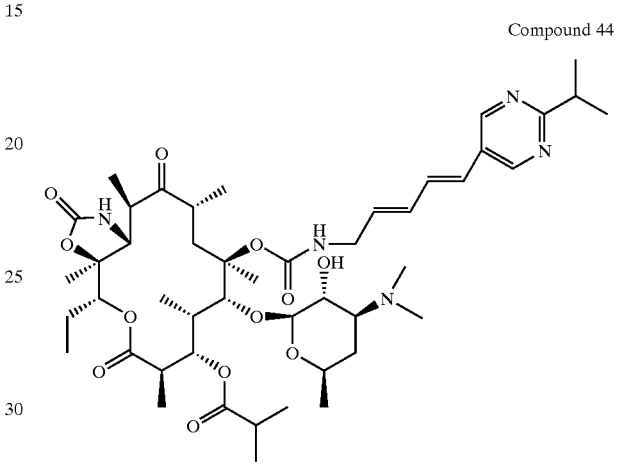

A solution of compound 2H-oxacyclotetradecino[4,3-d]oxazole-2,6,14(1H,7H)-trione, 10-[[2-O-acetyl-3,4,6-trideoxy-3-(dimethylamino)-β-D-xylo-hexopyranosyl]oxy]-11-[(aminocarbonyl)oxy]-4-ethyldecahydro-8-hydroxy-3a,7,9,11,13,15-hexamethyl-, (3aS,4R,7R,8S,9S,10R,11R,13R,15R,15aR)-(0.52 g, 0.76 mmol),

EXAMPLE 57

Carbamic acid, [(2E)-3-(4-pyrazinylphenyl)-2-propenyl]-, (3aS,4R,7R,8S,9S,10R,11R,13R,15R,15aR)-10-[[2-O-acetyl-3,4,6-trideoxy-3-(dimethylamino)-β-D-xylo-hexopyranosyl]oxy]4-ethyltetradecahydro-8-hydroxy-3a,7,9,11,13,15-hexamethyl-2,6,14-trioxo-2H-oxacyclotetradecino[4,3-d]oxazol-11-yl ester

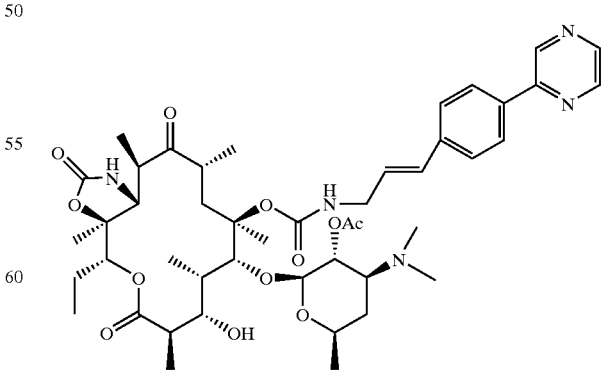

To a mixture of compound 2H-oxacyclotetradecino[4,3-d]oxazole-2,6,14(1H,7H)-trione, 10-[[2-O-acetyl-3,4,6- trideoxy-3-(dimethylamino)-β-D-xylo-hexopyranosyl]oxy]-11-[(aminocarbonyl)oxy]-4-ethyldecahydro-8-hydroxy-3a,7,9,11,13,15-hexamethyl-, (3aS,4R,7R,8S,9S,10R,11R,13R,15R,15aR)-(1.0 g, 1.46 mmol)

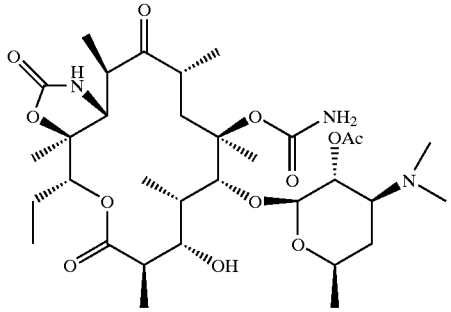

and (2E)-3-[4-(2-pyrazinyl)phenyl]-propenylaldehyde (1.3 q, 6.2 mmol) (Reference Example 18) in CH₃CN (8 mL) was added triethylsilane (1.2 mL, 7.5 mmol) and trifluoroacetic acid (0.58 mL, 7.5 mmol). The reaction was stirred for 2 hours then was heated at 60° C. for 18 h before being quenched with sat. aq. NaHCO₃ (10 mL). The mixture was extracted with ethyl acetate (40 mL×3). The organic layers were combined, washed with brine (15 mL) and dried over MgSO₄. Concentration and purification by chromatography (silica gel, 97:3:0.3 dichloromethane/methanol/conc. NH₄OH) gave 0.81 (63%) of the title compound. MS 880 (M+H)⁺.

EXAMPLE 58

Compound 45

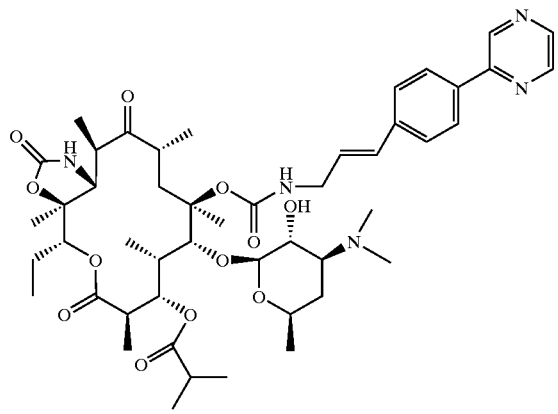

To a mixture of compound of Example 57 (0.125 g, 0.142) and a catalytic amount of 4-dimethylaminopyridine in CH₂Cl₂ (3 mL) was added triethylamine (0.158 mL, 1.14 mmol) then isobutyric anhydride (0.141 mL, 0.852). The mixture was stirred for 18 hours and additional triethylamine (0.158 mL, 1.14 mmol) and isoutyric anhydride (0.141 mL, 0.852) were added. The mixture is stirred for 42 hours and additional triethylamine (0.158 mL, 1.14 mmol) and isoutyric anhydride (0.141 mL, 0.852) were added. The mixture was stirred for 2.5 days and was diluted with ethyl acetate (20 mL). The mixture was washed with sat. aq. NH₄Cl, sat. aq. NaHCO₃, brine, and dried over MgSO₄. The mixture was concentrated and the residue dissolved in methanol (10 mL) and stirred for 18 h. K₂CO₃ (0.12 g, 0.854 mmol) was added and the mixture was stirred for 2.5 hours then concentrated, dissolved in ethyl acetate, washed with sat. aq. NaHCO₃, brine, and dried over MgSO₄. Concentration and purification by chromatography (silica gel, 97:3:0.3 dichloromethane/methanol/conc. NH₄OH) gave 32 mg (25%) of the title compound. MS 908 (M+H)⁺.

EXAMPLE 59

Carbamic acid, [(2E)-3-[4-(3-pyridazinyl)phenyl]-2-propenyl]-, (3aS,4R,7R,8S,9S,10R,11R,13R,15R,15aR)-10-[[2-O-acetyl-3,4,6-trideoxy-3-(dimethylamino)-β-D-xylo-hexopyranosyl]oxy]4-ethyltetradecahydro-8-hydroxy-3a,7,9,11,13,15-hexamethyl-2,6,14-trioxo-2H-oxacyclotetradecino[4,3-d]oxazol-11-yl ester

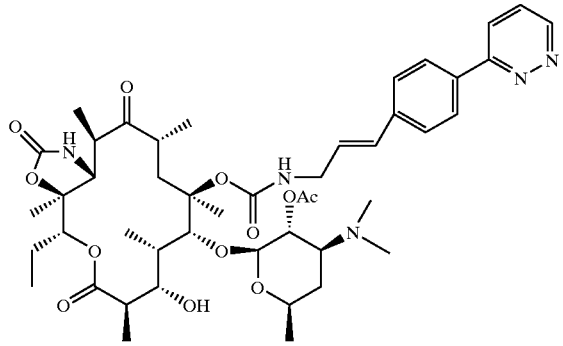

To a mixture of compound 2H-oxacyclotetradecino[4,3-d]oxazole-2,6,14(1H,7H)-trione, 10-[[2-O-acetyl-3,4,6-trideoxy-3-(dimethylamino)-β-D-xylo-hexopyranosyl]oxy]-11-[(aminocarbonyl)oxy]-4-ethyldecahydro-8-hydroxy-3a,7,9,11,13,15-hexamethyl-, (3aS,4R,7R,8S,9S,10R,11R,13R,15R,15aR)-(1.0 g, 1.46 mmol)

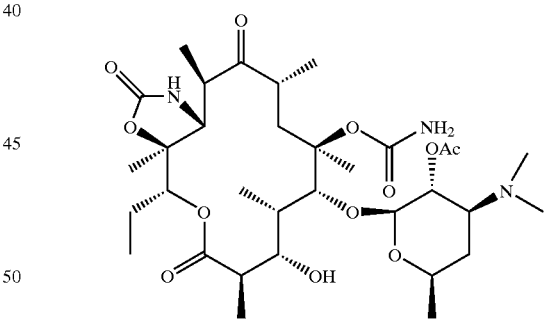

and (2E)-3-[4-(6-pyridazinyl)phenyl]-propenylaldehyde (1.3 g, 6.2 mmol) (Reference Example 19) in CH₃CN (8 mL) was added triethylsilane (1.2 mL, 7.5 mmol) and trifluoroacetic acid (0.58 mL, 7.5 mmol). The reaction was heated at 60° C. for 18 h then additional triethylsilane (1.2 mL, 7.5 mmol) and trifluoroacetic acid (0.58 mL, 7.5 mmol) were added. The reation was heated at 60° C. for 6.5 hours before being quenched with sat. aq. NaHCO₃ (10 mL). The mixture was extracted with ethyl acetate (40 mL×3). The organic layers were combined, washed with brine and dried over MgSO₄. Concentration and purification by chromatography (silica gel, 97:3:0.3 dichloromethane/methanol/conc. NH₄OH) gave 0.79 (62%) of the title compound. MS 880 (M+H)⁺.

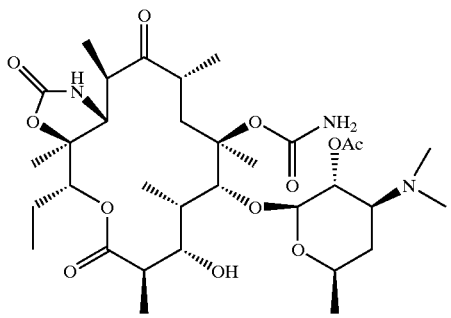

triethylsilane (1.2 mL, 7.53 mmol), trifluoroacetic acid (0.88 mL, 11.42 mmol) and 5-(2-isopropyl-pyrimidin-5-yl)-penta-2,4-dienal (0.46 g, 2.28 mmol) (Reference Example 17) in CH$_3$CN (6 mL) was heated at 65° C. for 23 h. The reaction was cooled to room temperature and diluted with CH$_2$Cl$_2$ (100 mL). The organic solution was washed with sat. aq. NaHCO$_3$ (15 mL) and brine (15 mL), and dried over MgSO$_4$, and concentrated. Purification by chromatography (silica gel, 96:4:0.3 dichloromethane/methanol/conc. NH$_4$OH) yielded 0.27 g (41%) of the product.

To the solution of the purified product (80 mg, 0.092 mmol) and catalytic amount of dimethylaminopyridine (DMAP) in CH$_2$Cl$_2$ (2 mL) was added triethylamine (0.19 mL, 1.37 mmol) and isobutyric anhydride (0.15 mL, 0.90 mmol). The reaction was stirred at room temperature for 6 days before being diluted with ethyl acetate (50 mL). The organic solution was washed with sat. aq. NH$_4$Cl, sat. aq. NaHCO$_3$ and brine, dried over MgSO$_4$ and concentrated. The crude product was dissolved in methanol (5 mL) and stirred at room temperature for 24 h. Potassium carbonate powder (0.1 g) was then added to the solution and the mixture was stirred for another 1 h before the mixture was diluted with ethyl acetate (50 mL). The organic solution was washed with H$_2$O (5 mL) and brine (5 mL), dried over MgSO$_4$, and concentrated. Purification by chromatography (silica gel, 94:6:0.3 dichloromethane/methanol/conc. NH$_4$OH) gave 34 mg (44%) of the title compound. MS 901 (M+H)$^+$.

EXAMPLE 60

Compound 46

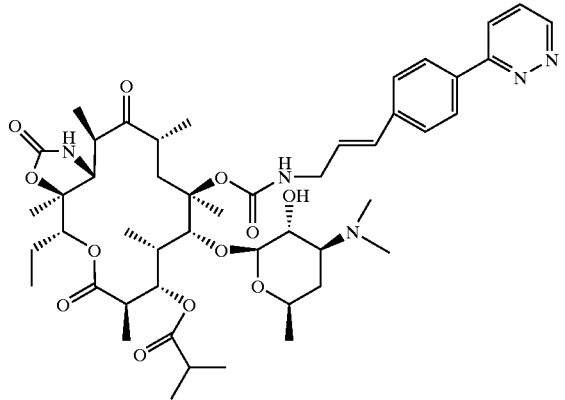

To a mixture of compound of Example 59 (0.1 g, 0.115) and a catalytic amount of 4-dimethylaminopyridine in CH$_2$Cl$_2$ (3 mL) was added triethylamine (0.128 mL, 0.922 mmol) then isobutyric anhydride (0.23 mL, 1.38). The mixture was stirred for 2 days and additional triethylamine (0.128 mL, 0.922 mmol) and isoutyric anhydride (0.115 mL, 0.461) were added. The mixture was stirred for 5 days and was diluted with ethyl acetate. The mixture was washed with sat. aq. NH$_4$Cl, sat. aq. NaHCO$_3$, brine, and dried over MgSO$_4$. The mixture was concentrated and the residue dissolved in methanol and stirred for 18 h. K$_2$CO$_3$ (0.12 g, 0.854 mmol) was added and the mixture was stirred for 3 h then dissolved in ethyl acetate, washed with sat. aq. NaHCO$_3$, brine, and dried over MgSO$_4$. Concentration and purification by chromatography (silica gel, 97:3:0.3 dichloromethane/methanol/conc. NH$_4$OH) gave 42 mg (40%) of the title compound. MS 908 (M+H)$^+$.

EXAMPLE 61

Carbamic acid, [(2E)-3-[4(1H-1,2,4-triazol-1-yl)phenyl]-2-propenyl]-, (3aS,4R,7R,8S,9S,10R,11R,13R,15R,15aR)-10-[[2-O-acetyl-3,4,6-trideoxy-3-(dimethylamino)-β-D-xylo-hexopyranosyl]oxy]-4-ethyltetradecahydro-8-hydroxy-3a,7,9,11,13,15-hexamethyl-2,6,14-trioxo-2H-oxacyclotetradecino[4,3-d]oxazol-11-yl ester

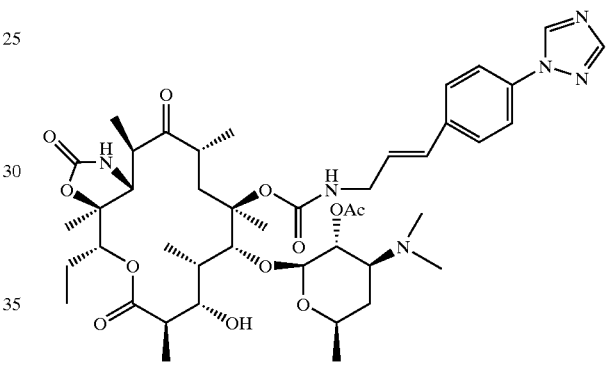

To a mixture of compound 2H-oxacyclotetradecino[4,3-d]oxazole-2,6,14(1H,7H)-trione, 10-[[2-O-acetyl-3,4,6-trideoxy-3-(dimethylamino)-β-D-xylo-hexopyranosyl]oxy]-11-[(aminocarbonyl)oxy]-4-ethyldecahydro-8-hydroxy-3a,7,9,11,13,15-hexamethyl-, (3aS,4R,7R,8S,9S,10R,11R,13R,15R, 15aR)-(1.0 g, 1.46 mmol)

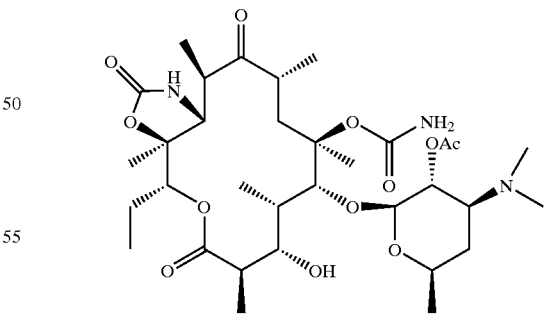

and (2E)-3-[4-(2-(1,2,4-triazole)phenyl]-propenylaldehyde (0.87 g, 4.37 mmol) (Reference Example 20) in CH$_3$CN (8 mL) was added triethylsilane (1.2 mL, 7.5 mmol) and trifluoroacetic acid (0.58 mL, 7.5 mmol). The reaction was heated at 65° C. for 18 h then additional triethylsilane (0.6 mL, 3.76 mmol) and trifluoroacetic acid (0.3 mL, 3.08 mmol) were added. The reation was heated at 65° C. for 4 hours before being quenched with sat. aq. NaHCO$_3$ (10 mL).

The mixture was extracted with ethyl acetate (40 mL×3). The organic layers were combined, washed with brine and dried over MgSO$_4$. Concentration and purification by chromatography (silica gel, 97:3:0.3 dichloromethane/methanol/ conc. NH$_4$OH) gave 0.82 (65%) of the title compound. MS 869 (M+H)$^+$.

EXAMPLE 62

Compound 47

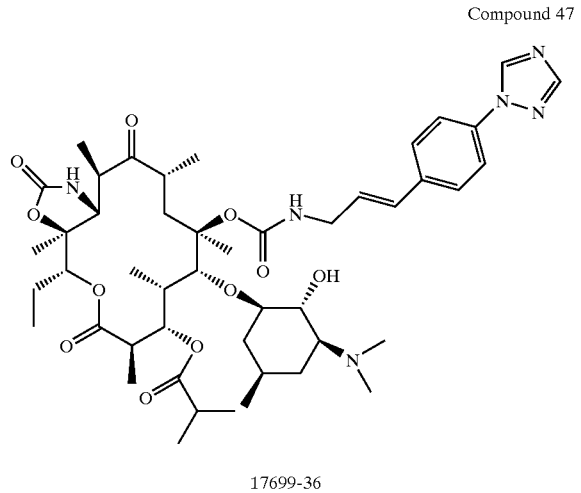

17699-36

To a mixture of compound of Example 61 (0.1 g, 0.115) and a catalytic amount of 4-dimethylaminopyridine in CH$_2$Cl$_2$ (3 mL) was added triethylamine (0.128 mL, 0.922 mmol) then isobutyric anhydride (0.23 mL, 1.38). The mixture was stirred for 5 days and additional isoutyric anhydride (0.1 mL, 0.603) was added. The mixture was stirred for 1 day and was diluted with ethyl acetate. The mixture was washed with sat. aq. NH$_4$Cl, sat. aq. NaHCO$_3$, brine, and dried over MgSO$_4$. The mixture was concentrated and the residue dissolved in methanol and stirred for 20 h. K$_2$CO$_3$ (0.12 g, 0.854 mmol) was added and the mixture was stirred for 3 h then dissolved in ethyl acetate, washed with water, sat. aq. NaHCO$_3$, brine, and dried over MgSO$_4$. Concentration and purification by chromatography (silica gel, 97:3:0.3 dichloromethane/methanol/conc. NH$_4$OH) gave 32 mg (31%) of the title compound. MS 897 (M+H)$^+$.

EXAMPLE 63

Carbamic acid, [(2E)-3-[4-(1H-pyrazol-1-yl) phenyl]-2-propenyl]-, (3aS,4R,7R,8S,9S,10R,11R, 13R,15R,15aR)-10-[[2-O-acetyl-3,4,6-trideoxy-3-(dimethylamino)-β-D-xylo-hexopyranosyl]oxy]4-ethyltetradecahydro-8-hydroxy-3a,7,9,11,13,15-hexamethyl-2,6,14-trioxo-2H-oxacyclotetradecino[4,3-d]oxazol-11-yl ester

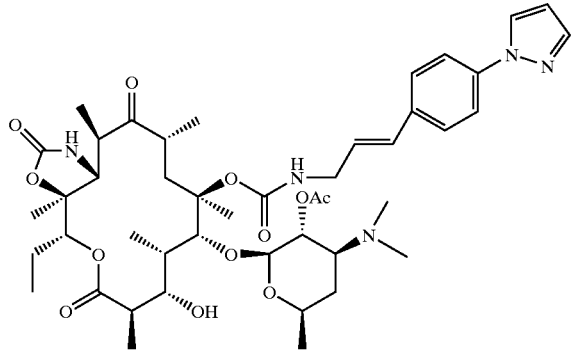

To a mixture of compound 2H-oxacyclotetradecino[4,3-d]oxazole-2,6,14(1H,7H)-trione, 10-[[2-O-acetyl-3,4,6-trideoxy-3-(dimethylamino)-β-D-xylo-hexopyranosyl]oxy]-1-[(aminocarbonyl)oxy]-4-ethyldecahydro-8-hydroxy-3a,7,9,11,13,15-hexamethyl-, (3aS,4R,7R,8S,9S,10R,11R,13R,15R,15aR)-(1.0 g, 1.46 mmol)

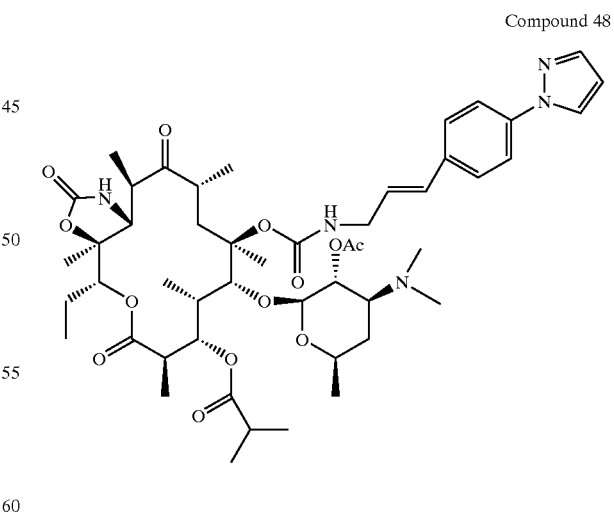

and (2E)-3-[4-(1H-pyrazole)phenyl]-propenylaldehyde (0.87 g, 4.37 mmol) (Reference Example 21) in CH$_3$CN (8 mL) was added triethylsilane (1.2 mL, 7.5 mmol) and trifluoroacetic acid (0.58 mL, 7.5 mmol). The reaction was heated at 65° C. for 18 h before being quenched with sat. aq. NaHCO$_3$ (10 mL). The mixture was extracted with ethyl acetate (40 mL×3). The organic layers were combined, washed with brine and dried over MgSO$_4$. Concentration and purification by chromatography (silica gel, 97:3:0.3 dichloromethane/methanol/conc. NH$_4$OH) gave 0.60 g (47%) of the title compound. MS 868 (M+H)$^+$.

EXAMPLE 64

Compound 48

To a mixture of compound of Example 63 (0.1 g, 0.115) and a catalytic amount of 4-dimethylaminopyridine in CH$_2$Cl$_2$ (3 mL) was added triethylamine (0.128 mL, 0.922 mmol) then isobutyric anhydride (0.23 mL, 1.38). The mixture was stirred for 2 days and additional triethylamine (0.128 mL, 0.922 mmol) and isoutyric anhydride (0.115 mL, 0.461) were added. The mixture was stirred for 5 days and was diluted with ethyl acetate. The mixture was washed with sat. aq. NH$_4$Cl, sat. aq. NaHCO$_3$, brine, and dried over MgSO$_4$. The mixture was concentrated and the residue dissolved in methanol and stirred for 18 h. K$_2$CO$_3$ (0.12 g, 0.854 mmol) was added and the mixture was stirred for 2 h. Additional K$_2$CO$_3$ (0.12 g, 0.854 mmol) was added and the mixture was stirred for 2 hours then dissolved in ethyl acetate, washed with sat. aq. NaHCO$_3$, brine, and dried over MgSO$_4$. Concentration and purification by chromatography (silica gel, 97:3:0.3 dichloromethane/methanol/conc. NH$_4$OH) gave 47 mg (46%) of the title compound. MS 896 (M+H)$^+$.

EXAMPLE 65

Carbamic acid, [(2E)-3-[4-(1-methyl-1H-pyrazol-3-yl)phenyl]-2-propenyl]-, (3aS,4R,7R,8S,9S,10R,11R,13R,15R,15aR)-10-[[2-O-acetyl-3,4,6-trideoxy-3-(dimethylamino)-β-D-xylo-hexopyranosyl]oxy]-4-ethyltetradecahydro-8-hydroxy-3a,7,9,11,13,15-hexamethyl-2,6,14-trioxo-2H-oxacyclotetradecino[4,3-d]oxazol-11-yl ester

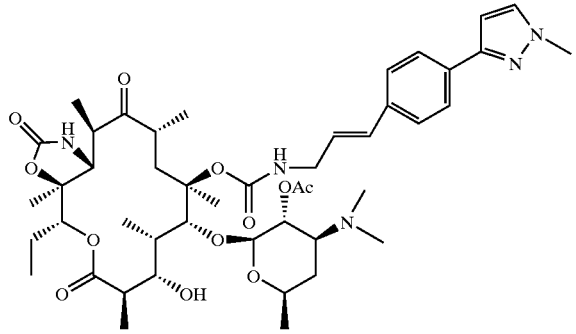

To a mixture of compound 2H-oxacyclotetradecino[4,3-d]oxazole-2,6,14(1H,7H)-trione, 10-[[2-O-acetyl-3,4,6-trideoxy-3-(dimethylamino)-β-D-xylo-hexopyranosyl]oxy]-11-[[(aminocarbonyl)oxy]-4-ethyldecahydro-8-hydroxy-3a,7,9,11,13,15-hexamethyl-, (3aS,4R,7R,8S,9S,10R,11R,13R,15R,15aR)-(0.61 g, 0.926 mmol)

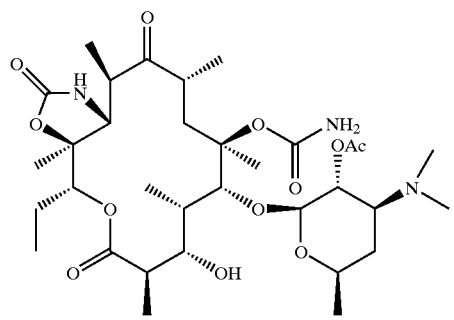

and (2E)-3-{4-[3-(1H-methylpyrazole)]phenyl}-propenylaldehyde (0.59 g, 2.78 mmol) (Reference Example 22) in CH$_3$CN (7 mL) was added triethylsilane (1.0 mL, 6.48 mmol) and trifluoroacetic acid (0.50 mL, 6.48 mmol). The reaction was heated at 65° C. for 18 h before being quenched with sat. aq. NaHCO$_3$ (10 mL). The mixture was extracted with ethyl acetate (30 mL×3). The organic layers were combined, washed with brine and dried over MgSO$_4$. Concentration and purification by chromatography (silica gel, 97:3:0.3 dichloromethane/methanol/conc. NH$_4$OH) gave 0.41 (50%) of the title compound. MS 881 (M+H)$^+$.

EXAMPLE 66

Compound 49

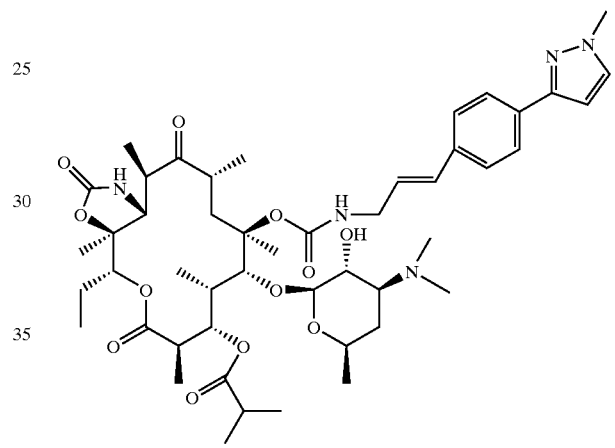

To a mixture of compound of Example 65 (0.1 g, 0.113) and a catalytic amount of 4-dimethylaminopyridine in CH$_2$Cl$_2$ (3 mL) was added triethylamine (0.128 mL, 0.91 mmol) then isobutyric anhydride (0.23 mL, 1.38). The mixture was stirred for 5 days and additional isoutyric anhydride (0.23 mL, 1.36) was added. The mixture was stirred for 6 days and additional isobutyric anhydride (0.15 mL, 0.68) was added. The mixture was stirred for 3 days and was diluted with ethyl acetate. The mixture was washed with sat. aq. NH$_4$Cl, sat. aq. NaHCO$_3$, brine, and dried over MgSO$_4$. The mixture was concentrated and the residue dissolved in methanol and stirred for 18 h. K$_2$CO$_3$ (0.125 g, 0.904 mmol) was added and the mixture was stirred for 3 h then concentration and purification by chromatography (silica gel, 97:3:0.3 dichloromethane/methanol/conc. NH$_4$OH) gave 66 mg (64%) of the title compound. MS 910 (M+H)$^+$.

EXAMPLE 67

Compound 50

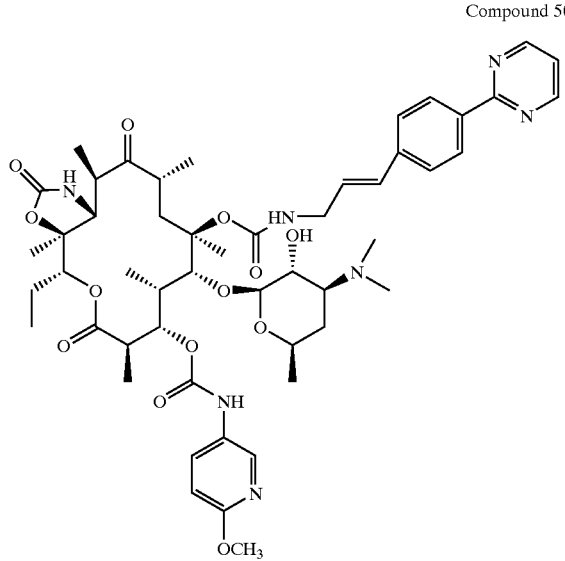

To the solution of compound of Example 1 (56 mg, 0.064 mmol) and catalytic amount of dimethylaminopyridine in CH$_2$Cl$_2$ (2 mL) was added 4-methoxyphenyl isocyanate (0.05 mL, 0.36 mmol). The reaction was stirred at room temperature for 24 h before being diluted with ethyl acetate (50 mL). The organic solution was washed with sat. aq. NaHCO$_3$ (10 mL) and brine, dried over MgSO$_4$, and concentrated. Purification by chromatography (silica gel, 93:7:0.3 dichloromethane/methanol/conc. NH$_4$OH) yielded 65 mg of product. This purified product was dissolved in methanol (5 mL) and stirred at room temperature for 24 h. Concentration and purification by chromatography (silica gel, 97:3:0.3 dichloromethane/methanol/conc. NH$_4$OH) yielded 34 mg (54%) of the title compound. MS 987 (M+H)$^+$.

EXAMPLE 68

Compound 51

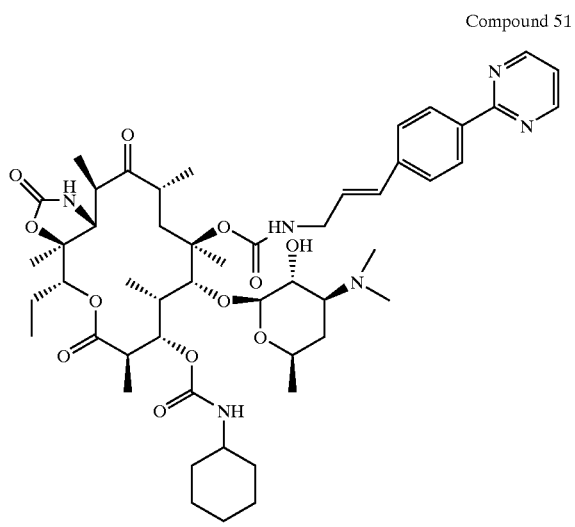

To the solution of compound of Example 1 (80 mg, 0.09 mmol) and catalytic amount of dimethylaminopyridine in toluene (2 mL) was added cyclohexyl isocyanate (0.06 mL, 0.47 mmol). The reaction was heated to reflux for 16 h. The toluene was then removed and the residue was dissolved in methanol (5 mL) and stirred at room temperature for 20 h. Concentration and purification by chromatography (silica gel, 94:6:0.3 dichloromethane/methanol/conc. NH$_4$OH) yielded 50 mg (57%) of the title compound. MS 963 (M+H)$^+$.

EXAMPLE 69

Compound 52

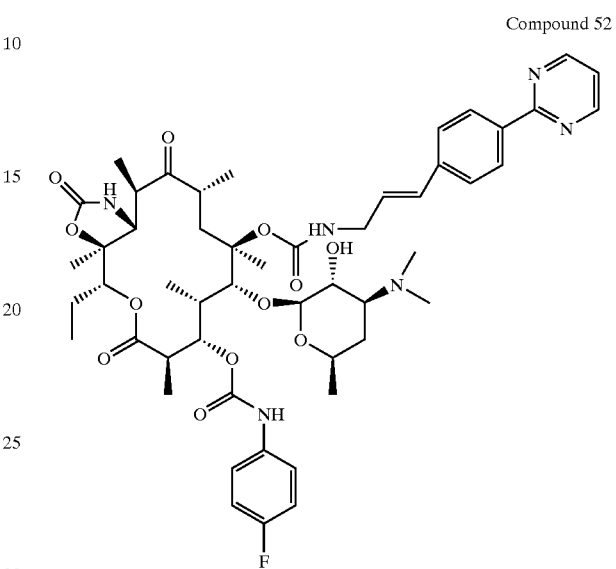

To the solution of compound of Example 1 (90 mg, 0.10 mmol) and catalytic amount of dimethylaminopyridine in toluene (2 mL) was added 4-fluorophenyl isocyanate (0.035 mL, 0.31 mmol). The reaction was stirred at room temperature for 6 h before being diluted with methanol (5 mL) and stirred at room temperature for 16 h. Concentration and purification by chromatography (silica gel, 96:4:0.3 dichloromethane/methanol/conc. NH$_4$OH to 94:6:0.3 dichloromethane/methanol/conc. NH$_4$OH) yielded 48 mg (48%) of the title compound. MS 976 (M+H)$^+$.

EXAMPLE 70

Compound 53

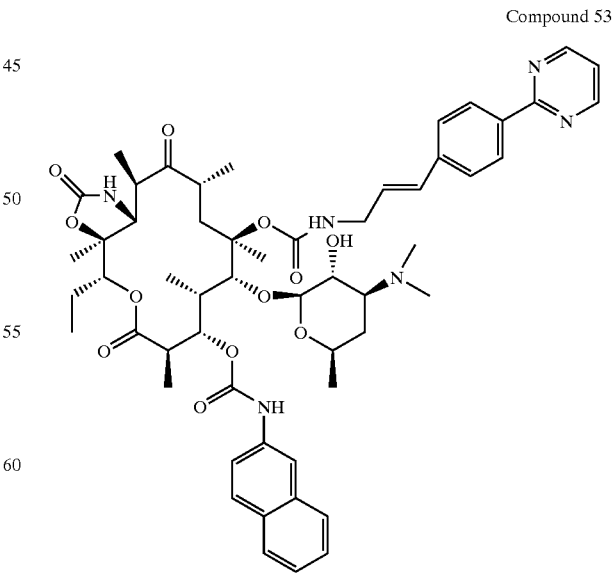

To the solution of compound of Example 1 (94 mg, 0.11 mmol) and catalytic amount of dimethylaminopyridine in toluene (2 mL) was added 2-naphthyl isocyanate (54 mg, 0.32 mmol). The reaction was stirred at room temperature for 20 h before being diluted with methanol (5 mL) and stirred at room temperature for 60 h. The mixture was filtered and the solution was concentrated to give the crude product. Purification by chromatography (silica gel, 95:5:0.3 dichloromethane/methanol/conc. NH$_4$OH) yielded 77 mg (72%) of the title compound. MS 1007 (M+H)$^+$.

EXAMPLE 71

Compound 54

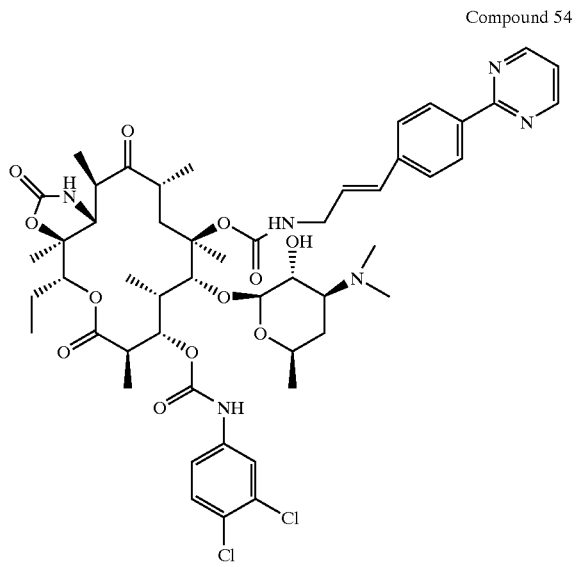

To the solution of compound of Example 1 (100 mg, 0.11 mmol) and catalytic amount of dimethylaminopyridine in toluene (2 mL) was added 3,4-dichlorophenyl isocyanate (64 mg, 0.34 mmol). The reaction was stirred at room temperature for 24 h before being diluted with methanol (5 mL) and stirred at room temperature for 60 h. The mixture was filtered and the solution was concentrated to give the crude product. Purification by chromatography (silica gel, 95:5:0.3 dichloromethane/methanol/conc. NH$_4$OH) yielded 79 mg (68%) of the title compound. MS 1026 (M+H)$^+$.

EXAMPLE 72

Compound 55

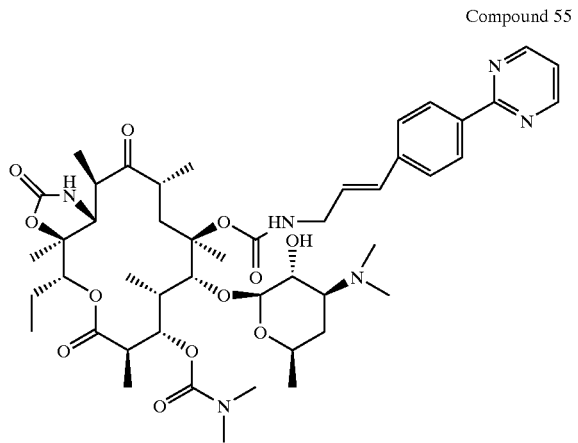

To the solution of compound of Example 1 (82 mg, 0.093 mmol) and catalytic amount of dimethylaminopyridine in CH$_2$Cl$_2$ (2 mL) at 0° C. was added triethylamine (0.13 mL, 0.93 mmol) and diphosgen (0.06 mL, 0.50 mmol). The reaction was warmed to room temperature and stirred for 16 h. Dimethylamine (2 M solution in THF, 0.6 mL, 1.2 mmol) was added to the reaction and the mixture was stirred for another 3 h before being diluted with ethyl acetate (50 mL). The organic solution was washed with sat. aq. NH$_4$Cl (5 mL×2), sat. aq. NaHCO$_3$ (5 mL) and brine, dried over MgSO$_4$, and concentrated. The crude product was dissolved in methanol (5 mL) and stirred at room temperature for 72 h. Concentration and purification by chromatography (silica gel, 95:5:0.3 dichloromethane/methanol/conc. NH$_4$OH) yielded 35 mg (41%) of the title compound. MS 909 (M+H)$^+$.

EXAMPLE 73

Compound 56

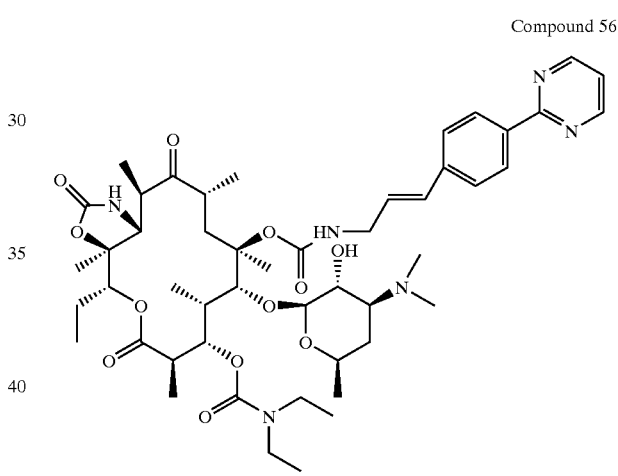

To the solution of compound of Example 1 (90 mg, 0.10 mmol) and catalytic amount of dimethylaminopyridine in CH$_2$Cl$_2$ (2 mL) at 0° C. was added triethylamine (0.15 mL, 1.1 mmol) and diphosgen (0.07 mL, 0.58 mmol). The reaction was warmed to room temperature and stirred for 16 h. Diethylamine (0.16 mL, 1.55 mmol) was added to the reaction and the mixture was stirred for another 24 h before being diluted with ethyl acetate (50 mL). The organic solution was washed with sat. aq. NH$_4$Cl (5 mL×2), sat. aq. NaHCO$_3$ (5 mL) and brine, dried over MgSO$_4$, and concentrated. The crude product was dissolved in methanol (5 mL) and stirred at room temperature for 24 h. Concentration and purification by chromatography (silica gel, 95:5:0.3 dichloromethane/methanol/conc. NH$_4$OH) yielded 30 mg (31%) of the title compound. MS 959 (M+Na)$^+$.

EXAMPLE 74

Compound 57

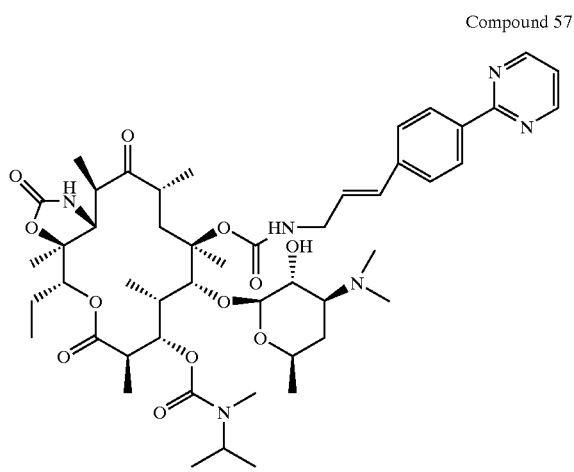

To the solution of compound of Example 1 (90 mg, 0.10 mmol) and catalytic amount of dimethylaminopyridine in $CH_2Cl_2$ (2 mL) at 0° C. was added triethylamine (0.15 mL, 1.1 mmol) and diphosgen (0.07 mL, 0.58 mmol). The reaction was warmed to room temperature and stirred for 16 h. Isopropylethylamine (0.16 mL, 1.55 mmol) was added to the reaction and the mixture was stirred for another 24 h before being diluted with ethyl acetate (50 mL). The organic solution was washed with sat. aq. $NH_4Cl$ (5 mL×2), sat. aq. $NaHCO_3$ (5 mL) and brine, dried over $MgSO_4$, and concentrated. The crude prouduct was dissolved in methanol (5 mL) and stirred at room temperature for 48 h. Concentration and purification by chromatography (silica gel, 95:5:0.3 dichloromethane/methanol/conc. $NH_4OH$) yielded 36 mg (38%) of the title compound. MS 937 $(M+H)^+$.

EXAMPLE 75

Compound 58

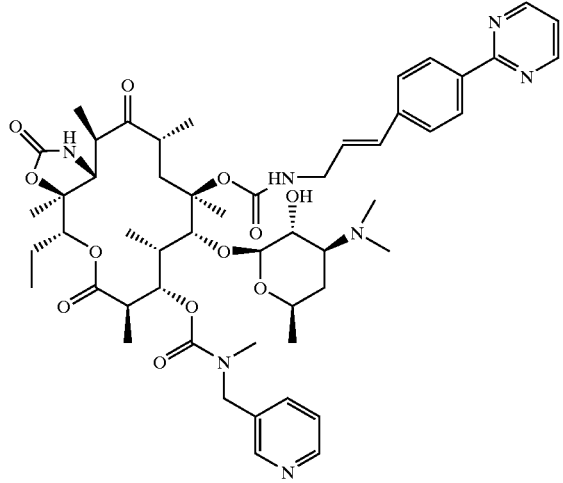

To the solution of compound of Example 1 (94 mg, 0.107 mmol) and catalytic amount of dimethylaminopyridine in $CH_2Cl_2$ (2 mL) at 0° C. was added triethylamine (0.12 mL, 0.86 mmol) and diphosgen (0.05 mL, 0.41 mmol). The reaction was warmed to room temperature and stirred for 24 h. N-methyl-N-(3-pyridylmethyl)amine (105 mg in 0.5 mL $CH_2Cl_2$, 0.86 mmol) was added to the reaction and the mixture was stirred for another 24 h before being diluted with ethyl acetate (50 mL). The organic solution was washed with sat. aq. $NH_4Cl$ (5 mL×2), sat. aq. $NaHCO_3$ (5 mL) and brine, dried over $MgSO_4$, and concentrated. The crude product was dissolved in methanol (5 mL) and stirred at room temperature for 24 h. Concentration and purification by chromatography (silica gel, 93:7:0.3 dichloromethane/methanol/conc. $NH_4OH$) yielded 14 mg (13%) of the title compound. MS 986 $(M+H)^+$.

EXAMPLE 76

Compound 59

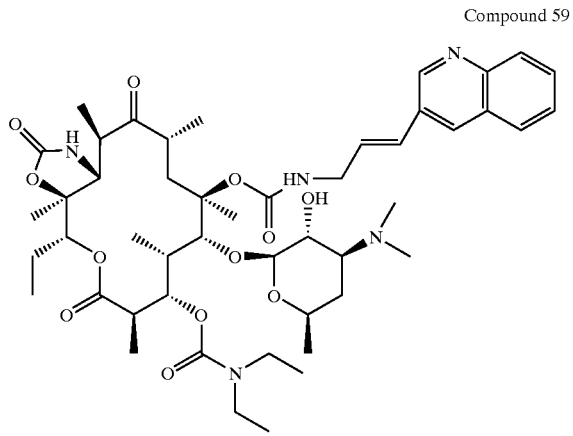

To the solution of compound of Example 40 (60 mg, 0.070 mmol) and catalytic amount of dimethylaminopyridine in $CH_2Cl_2$ (2 mL) at 0° C. was added pyridine (0.06 mL, 0.74 mmol) and diphosgen (0.04 mL, 0.33 mmol). The reaction was warmed to room temperature and stirred for 24 h. Diethylamine (0.11 mL, 1.07 mmol) was added to the reaction and the mixture was stirred for another 24 h before being diluted with ethyl acetate (70 mL). The organic solution was washed with sat. aq. $NH_4Cl$ (5 mL×2), sat. aq. $NaHCO_3$ (10 mL) and brine, dried over $MgSO_4$, and concentrated. The residue was dissolved in methanol (5 mL) and stirred at room temperature for 60 h. Concentration and purification by chromatography (silica gel, 94:6:0.3 dichloromethane/methanol/conc. $NH_4OH$) yielded 14 mg (22%) of the title compound. MS 911 $(M+H)^+$.

EXAMPLE 77

Compound 60

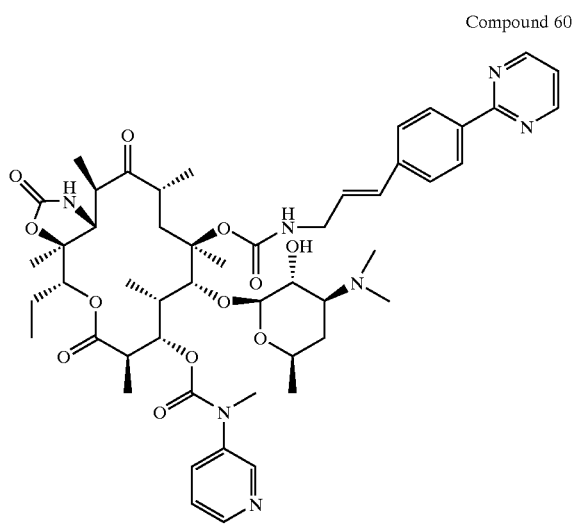

To the solution of compound of Example 1 (85 mg, 0.097 mmol) and catalytic amount of dimethylaminopyridine in CH$_2$Cl$_2$ (2 mL) at 0° C. was added pyridine (0.20 mL, 2.48 mmol) and diphosgen (0.05 mL, 0.41 mmol). The reaction was warmed to room temperature and stirred for 36 h. N-methyl-N-(3-pyridy)amine (160 mg in 0.5 mL CH$_2$Cl$_2$, 1.48 mmol) was added to the reaction and the mixture was stirred for another 24 h before being diluted with ethyl acetate (50 mL). The organic solution was washed with sat. aq. NH$_4$Cl (5 mL×2), sat. aq. NaHCO$_3$ (5 mL) and brine, dried over MgSO$_4$, and concentrated. The residue was dissolved in methanol (5 mL) and stirred at room temperature for 24 h. Concentration and purification by chromatography (silica gel, 93:7:0.3 dichloromethane/methanol/conc. NH$_4$OH) yielded 16 mg (13%) of the title compound. MS 972 (M+H)$^+$.

EXAMPLE 78

Compound 61

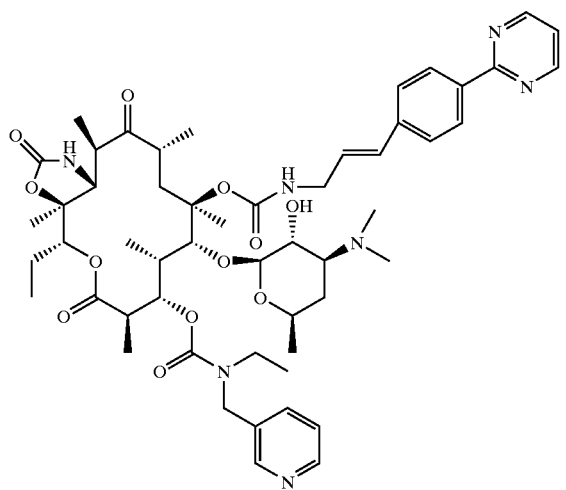

To the solution of compound of Example 1 (75 mg, 0.085 mmol) and catalytic amount of dimethylaminopyridine in CH$_2$Cl$_2$ (2 mL) at 0° C. was added pyridine (0.20 mL, 2.48 mmol) and diphosgen (0.05 mL, 0.41 mmol). The reaction was warmed to room temperature and stirred for 36 h. N-ethyl-N-(3-pyridymethyl)amine (240 mg in 0.5 mL CH$_2$Cl$_2$, 1.76 mmol) was added to the reaction and the mixture was stirred for another 24 h before being diluted with ethyl acetate (50 mL). The organic solution was washed with sat. aq. NH$_4$Cl (5 mL×2), sat. aq. NaHCO$_3$ (5 mL) and brine, dried over MgSO$_4$, and concentrated. The residue was dissolved in methanol (5 mL) and stirred at room temperature for 72 h. Concentration and purification by chromatography (silica gel, 93:7:0.3 dichloromethane/methanol/conc. NH$_4$OH) yielded 20 mg (23%) of the title compound. MS 1001 (M+H)$^+$.

EXAMPLE 79

Compound 62

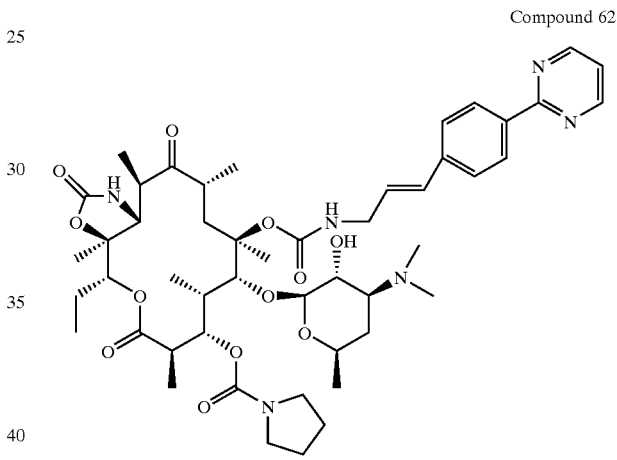

To the solution of compound of Example 1 (92 mg, 0.105 mmol) and catalytic amount of dimethylaminopyridine in CH$_2$Cl$_2$ (2 mL) at 0° C. was added pyridine (0.10 mL, 1.24 mmol) and diphosgen (0.063 mL, 0.52 mmol). The reaction was warmed to room temperature and stirred for 36 h. Pyrrolidine (0.175 mL CH$_2$Cl$_2$, 2.10 mmol) was added to the reaction and the mixture was stirred for another 24 h before being diluted with ethyl acetate (50 mL). The organic solution was washed with sat. aq. NH$_4$Cl (5 mL×2), sat. aq. NaHCO$_3$ (5 mL) and brine, dried over MgSO$_4$, and concentrated. The crude product was purified by chromatography (silica gel, 96:4:0.3 dichloromethane/methanol/conc. NH$_4$OH). The purified product was dissolved in methanol (5 mL) and stirred at room temperature for 24 h. Concentration and purification by chromatography (silica gel, 95:5:0.3 dichloromethane/methanol/conc. NH$_4$OH) yielded 35 mg (36%) of the title compound. MS 936 (M+H)$^+$.

EXAMPLE 80

Compound 63

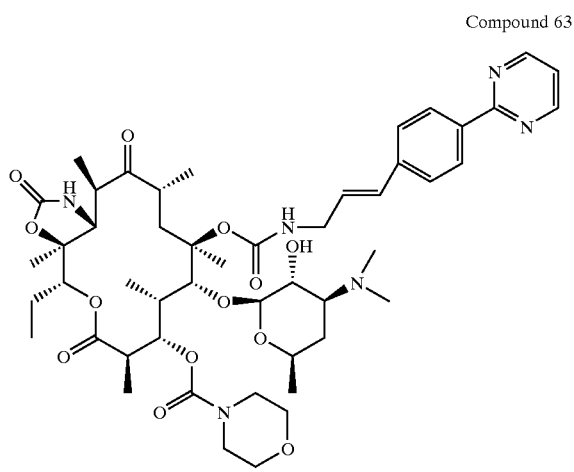

To the solution of compound of Example 1 (90 mg, 0.102 mmol) and catalytic amount of dimethylaminopyridine in CH$_2$Cl$_2$ (2 mL) at 0° C. was added pyridine (0.10 mL, 1.24 mmol) and diphosgen (0.060 mL, 0.50 mmol). The reaction was warmed to room temperature and stirred for 24 h. Morpholine (0.20 mL, 2.30 mmol) was added to the reaction and the mixture was stirred for another 24 h before being diluted with ethyl acetate (50 mL). The organic solution was washed with sat. aq. NH$_4$Cl (5 mL×2), sat. aq. NaHCO$_3$ (5 mL) and brine, dried over MgSO$_4$, and concentrated. The crude product was purified by chromatography (silica gel, 97:3:0.3 dichloromethane/methanol/conc. NH$_4$OH). The purified product was dissolved in methanol (5 mL) and stirred at room temperature for 24 h. Concentration and purification by chromatography (silica gel, 95:5:0.3 dichloromethane/methanol/conc. NH$_4$OH) yielded 30 mg (31%) of the title compound. MS 952 (M+H)$^+$.

EXAMPLE 81

Compound 64

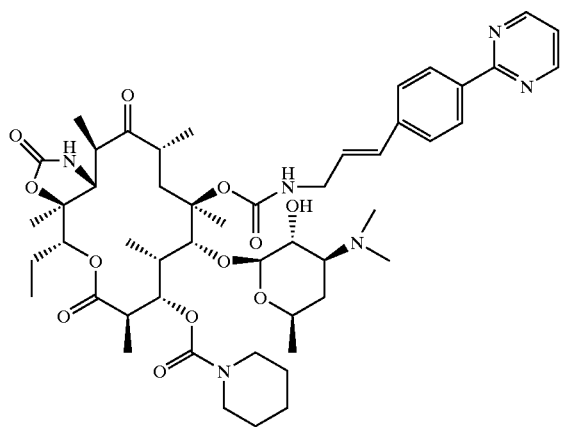

To the solution of compound of Example 1 (120 mg, 0.136 mmol) and catalytic amount of dimethylaminopyri dine in CH$_2$Cl$_2$ (2 mL) at 0° C. was added pyridine (0.20 mL, 2.48 mmol) and diphosgene (0.080 mL, 0.66 mmol). The reaction was warmed to room temperature and stirred for 24 h. Piperidine (0.20 mL, 2.02 mmol) was added to the reaction and the mixture was stirred for another 16 h before being diluted with ethyl acetate (50 mL). The organic solution was washed with sat. aq. NH$_4$Cl (5 mL×2), sat. aq. NaHCO$_3$ (5 mL) and brine, dried over MgSO$_4$, and concentrated. The crude product was purified by chromatography (silica gel, 97:3:0.3 dichloromethane/methanol/conc. NH$_4$OH). The purified product was dissolved in methanol (5 mL) and stirred at room temperature for 60 h. Concentration and purification by chromatography (silica gel, 95:5:0.3 dichloromethane/methanol/conc. NH$_4$OH) yielded 41 mg (32%) of the title compound. MS 949 (M+H)$^+$.

EXAMPLE 82

Compound 65

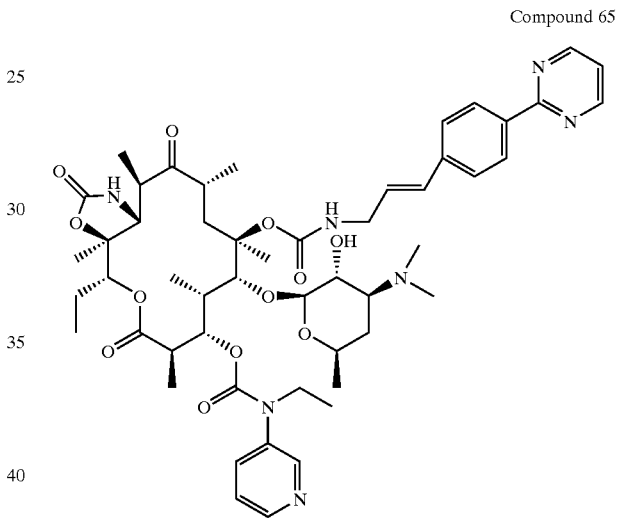

To the solution of compound of Example 1 (120 mg, 0.136 mmol) and catalytic amount of dimethylaminopyridine in CH$_2$Cl$_2$ (2 mL) at 0° C. was added pyridine (0.25 mL, 3.09 mmol) and phosgen (20% in toluene, 0.28 mL, 0.53 mmol). The reaction was warmed to room temperature and stirred for 7 h. N-ethyl-N-(3-pyridyl)amine (180 mg, 1.48 mmol) was added to the reaction and the mixture was stirred for another 16 h before being diluted with ethyl acetate (50 mL). The organic solution was washed with sat. aq. NH$_4$Cl (5 mL×2), sat. aq. NaHCO$_3$ (5 mL) and brine, dried over MgSO$_4$, and concentrated. The crude product was purified by chromatography (silica gel, 96:4:0.3 dichloromethane/methanol/conc. NH$_4$OH). The purified product was dissolved in methanol (5 mL) and stirred at room temperature for 72 h. Concentration and purification by chromatography (silica gel, 94:6:0.3 dichloromethane/ methanol/conc. NH$_4$OH) yielded 10 mg (7%) of the title compound. MS 987 (M+H)$^+$.

EXAMPLE 83

Compound 66

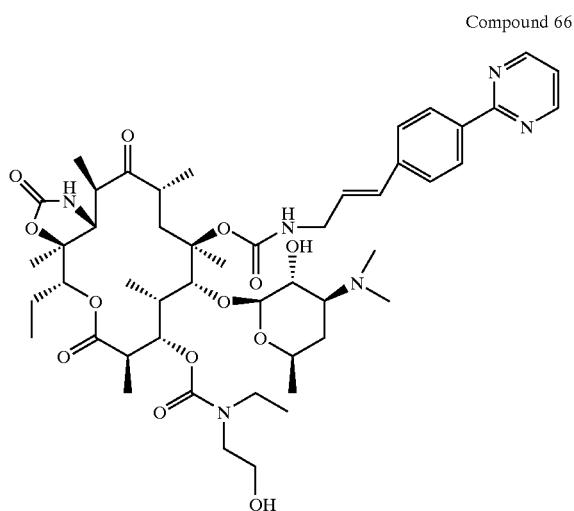

To the solution of compound of Example 1 (120 mg, 0.136 mmol) and catalytic amount of dimethylaminopyridine in CH$_2$Cl$_2$ (2 mL) at 0° C. was added pyridine (0.20 mL, 2.48 mmol) and diphosgen (0.08 mL, 0.66 mmol). The reaction was warmed to room temperature and stirred for 20 h. 2-(Ethylamino)ethanol (0.2 mL, 2.05 mmol) was added to the reaction and the mixture was stirred for another 16 h before being diluted with ethyl acetate (50 mL). The organic solution was washed with sat. aq. NH$_4$Cl (5 mL×2), sat. aq. NaHCO$_3$ (5 mL) and brine, dried over MgSO$_4$, and concentrated. The crude product was purified by chromatography (silica gel, 94:6:0.3 dichloromethane/methanol/conc. NH$_4$OH). The purified product was dissolved in methanol (5 mL) and stirred at room temperature for 72 h. Concentration and purification by chromatography (silica gel, 92:8:0.3 dichloromethane/methanol/conc. NH$_4$OH) yielded 17 mg (13%) of the title compound. MS 954 (M+H)$^+$.

EXAMPLE 84

Compound 67

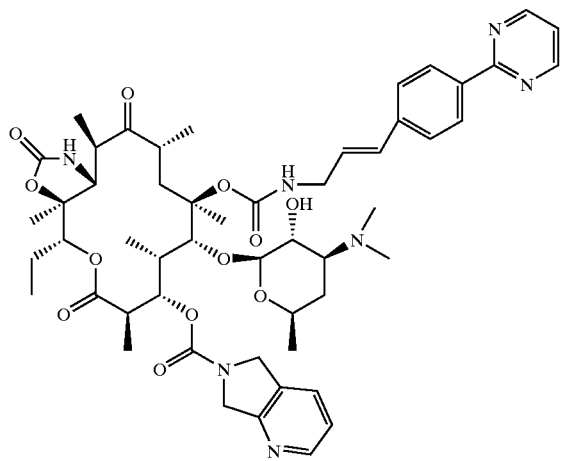

To the solution of compound of Example 1 (120 mg, 0.136 mmol) and catalytic amount of dimethylaminopyri dine in CH$_2$Cl$_2$ (2 mL) at 0° C. was added pyridine (0.20 mL, 2.48 mmol) and diphosgene (0.08 mL, 0.66 mmol). The reaction was warmed to room temperature and stirred for 24 h. 6,7-Dihydro-5H-pyrrolo[3,4-□]pyridine (0.4 g in 2 mL DMF, 2.07 mmol) was added to the reaction followed by diisopropylethylamine (0.2 mL). The mixture was stirred for another 16 h before being diluted with ethyl acetate (50 mL). The organic solution was washed with sat. aq. NH$_4$Cl (5 mL×2), sat. aq. NaHCO$_3$ (5 mL) and brine, dried over MgSO$_4$, and concentrated. The crude product was purified by chromatography (silica gel, 95:5:0.3 dichloromethane/methanol/conc. NH$_4$OH). The purified product was dissolved in methanol (5 mL) and stirred at room temperature for 72 h. Concentration and purification by chromatography (silica gel, 94:6:0.3 dichloromethane/methanol/conc. NH$_4$OH) yielded 7 mg (5%) of the title compound. MS 986 (M+H)$^+$.

EXAMPLE 85

Compound 68

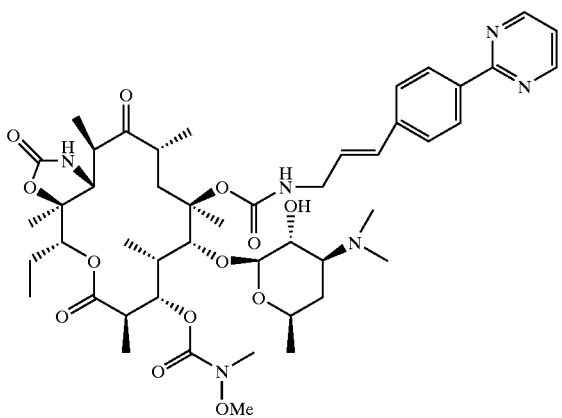

To the solution of compound of Example 1 (115 mg, 0.13 mmol) and catalytic amount of dimethylaminopyridine in CH$_2$Cl$_2$ (2 mL) at 0° C. was added pyridine (0.20 mL, 2.48 mmol) and diphosgene (0.06 mL, 0.50 mmol). The reaction was warmed to room temperature and stirred for 24 h. A solution of N,O-dimethylhydroxylamine hydrochloride (190 mg, 1.95 mmol) in CH$_2$Cl$_2$ (1 mL)/Pr$_2$EtN (0.2 mL) was added to the reaction and the mixture was stirred for another 16 h before being diluted with CH$_2$Cl$_2$ (50 mL). The organic solution was washed with sat. aq. NH$_4$Cl (5 mL×2), sat. aq. NaHCO$_3$ (5 mL) and brine, dried over MgSO$_4$, and concentrated. The crude product was dissolved in methanol (5 mL) and stirred at room temperature for 60 h. Concentration and purification by chromatography (silica gel, 94:6:0.3 dichloromethane/methanol/conc. NH$_4$OH) yielded 30 mg (25%) of the title compound. MS 926 (M+H)$^+$.

EXAMPLE 86

Compound 69

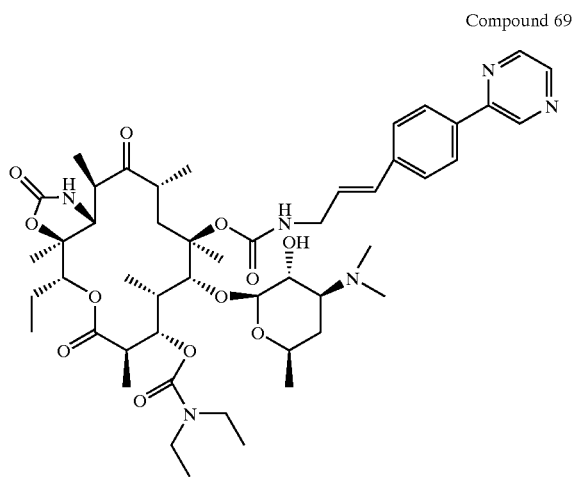

To a mixture of compound of Example 57 (0.125 g, 0.142 mmol) and a catalytic amount of 4-dimethylaminopyridine in CH$_2$Cl$_2$ (6 mL) at 0° C. was added triethylamine (0.3 mL, 2.13 mmol) then diphosgene (0.05 mL, 0.426 mmol). The reaction was stirred at ambient temperature for 18 h then additional 4-dimethylaminopyridine (cat.) and diphosgene (0.05 mL, 0.426 mmol) were added. The mixture was stirred for 7 hours and diethylamine (0.66 mL, 6.39 mmol) was added. The mixture was stirred for three days and diluted with ethyl actate. The mixture was extracted with sat. aq. NH$_4$Cl (2×), sat. aq. NaHCO$_3$ (2×), brine, and dried over MgSO$_4$. Concentration and purification by chromatography (silica gel, 97:3:0.3 dichloromethane/methanol/conc. NH$_4$OH) gave 20 mg which was dissolved in methanol (3 ml) and stirred for 48 h. Concentration and purification by chromatography (silica gel, 97:3:0.3 dichloromethane/methanol/conc. NH$_4$OH) gave 16 mg (12%) of the title compound. MS 937 (M+H)$^+$.

EXAMPLE 87

Compound 70

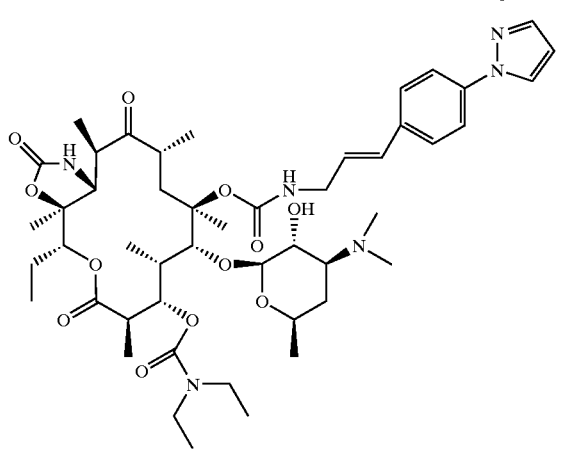

To a mixture of compound of Example 63 (0.125 g, 0.144 mmol) and a catalytic amount of 4-dimethylaminopyridine in CH$_2$Cl$_2$ (6 mL) at 0° C. was added triethylamine (0.3 mL, 2.13 mmol) then diphosgene (0.087 mL, 0.720 mmol). The reaction was stirred at ambient temperature for 18 h then additional diphosgene (0.020 mL, 0.166 mmol) was added. The mixture was stirred for 8 h and diethylamine (0.66 mL, 6.39 mmol) was added. The mixture was stirred for 18 h and diluted with ethyl actate (40 ml). The mixture was extracted with sat. aq. NH$_4$Cl (2×20 ml), sat. aq. NaHCO$_3$ (2×20 ml), brine, and dried over MgSO$_4$. Concentration and purification by chromatography (silica gel, 98:2:0.3 dichloromethane/methanol/conc. NH$_4$OH) gave 70 mg which was dissolved in methanol (5 ml) and stirred for 24 h. Concentration and purification by chromatography (silica gel, 97:3:0.3 dichloromethane/methanol/conc. NH$_4$OH) gave 56 mg (42%) of the title compound. MS 925 (M+H)$^+$.

EXAMPLE 88

Compound 71

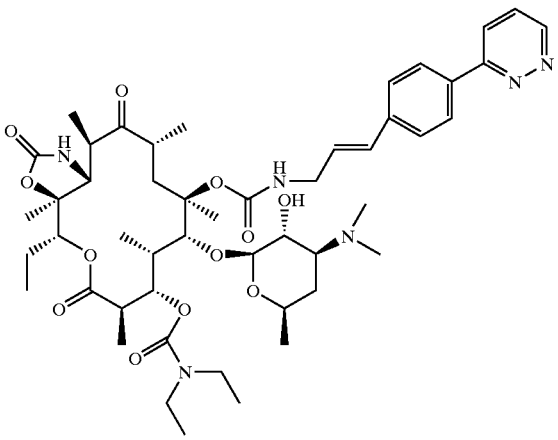

To a mixture of compound of Example 59 (0.125 g, 0.142 mmol) and a catalytic amount of 4-dimethylaminopyridine in CH$_2$Cl$_2$ (6 mL) at 0° C. was added pyridine (0.17 mL, 2.13 mmol) then diphosgene (0.085 mL, 0.710 mmol). The reaction was stirred at ambient temperature for 18 h and diethylamine (0.66 mL, 6.39 mmol) was added. The mixture was stirred for 72 h and diluted with ethyl actate. The mixture was extracted with sat. aq. NH$_4$Cl (2×), sat. aq. NaHCO$_3$ (2×), brine, and dried over MgSO$_4$. The residue was dissolved in methanol (10 ml) and stirred for 42 h. Concentration and purification by chromatography (silica gel, 97:3:0.3 dichloromethane/methanol/conc. NH$_4$OH) gave 32.5 mg (24%) of the title compound. MS 937 (M+H)$^+$.

EXAMPLE 89

Compound 72

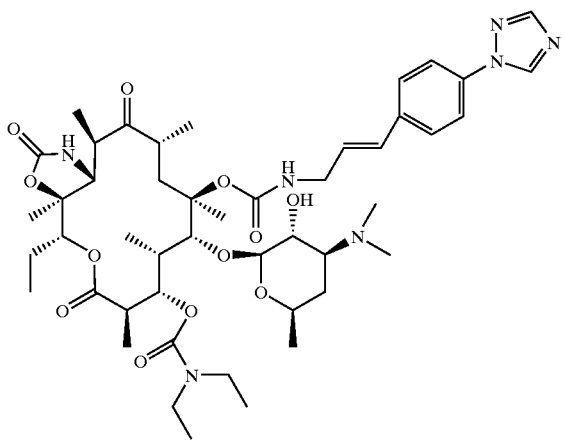

To a mixture of compound of Example 61 (0.125 g, 0.144 mmol) and a catalytic amount of 4-dimethylaminopyridine in CH$_2$Cl$_2$ (6 mL) at 0° C. was added pyridine (0.22 mL, 2.73 mmol) then diphosgene (0.11 mL, 0.912 mmol). The reaction was stirred at ambient temperature for 18 h and diethylamine (0.85 mL, 8.20 mmol) was added. The mixture was stirred for 6 h and diluted with ethyl actate (20 mL). The mixture was extracted with sat. aq. NH$_4$Cl, sat. aq. NaHCO$_3$, brine, and dried over MgSO$_4$. Concentration and purification by chromatography (silica gel, 97:3:0.3 dichloromethane/methanol/conc. NH$_4$OH) gave 45 mg which was dissolved in methanol (3 ml) and stirred for 18 h. Concentration and purification by chromatography (silica gel, 97:3:0.3 dichloromethane/methanol/conc. NH$_4$OH) gave 12 mg (9%) of the title compound. MS 926 (M+H)$^+$.

EXAMPLE 90

Compound 73

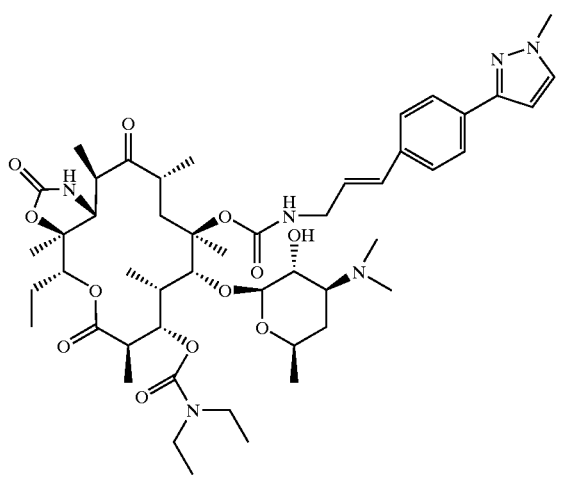

To a mixture of compound of Example 65 (0.125 g, 0.142 mmol) and a catalytic amount of 4-dimethylaminopyridine in CH$_2$Cl$_2$ (6 mL) at 0° C. was added pyridine (0.17 mL, 2.13 mmol) then diphosgene (0.085 mL, 0.709 mmol). The reaction was stirred at ambient temperature for 18 h and diethylamine (0.66 mL, 6.38 mmol) was added. The mixture was stirred for 5 h and diluted with ethyl actate. The mixture was extracted with sat. aq. NH$_4$Cl (2x), sat. aq. NaHCO$_3$ (2x), brine, and dried over MgSO$_4$. The mixture was concentrated and dissolved in methanol (5 ml) and stirred for 22 h. Concentration and purification by chromatography (silica gel, 97:3:0.3 dichloromethane/methanol/conc. NH$_4$OH) gave 10 mg (8%) of the title compound. MS 939 (M+H)$^+$.

EXAMPLE 91

1H-Pyrrole-1-carboxylic acid, 3-cyano-, (3aS,4R, 7R,8S,9S,10R,11R,13R,15R,15aR)-10-[[2-O-acetyl-3,4,6-trideoxy-3-(dimethylamino)-β-D-xylo-hexopyranosyl]oxy]-4-ethyltetradecahydro-8-hydroxy-3a,7,9,11,13,15-hexamethyl-2,6,14-trioxo-2H-oxacyclotetradecino[4,3-d]oxazol-11-yl ester

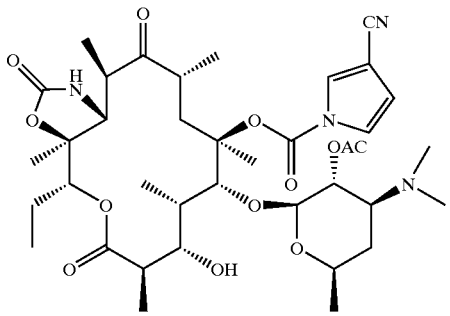

To the mixture of compound 2H-oxacyclotetradecino[4, 3-d]oxazole-2,6,14(1H,7H)-trione, 10-[[2-O-acetyl-3,4,6-trideoxy-3-(dimethylamino)-β-D-xylo-hexopyranosyl]oxy]-11-[(aminocarbonyl)oxy]-4-ethyldecahydro-8-hydroxy-3a, 7,9,11,13,15-hexamethyl-, (3aS,4R,7R,8S,9S,10R,11R,13R, 15R,15aR)-(1.57 g, 2.29 mmol)

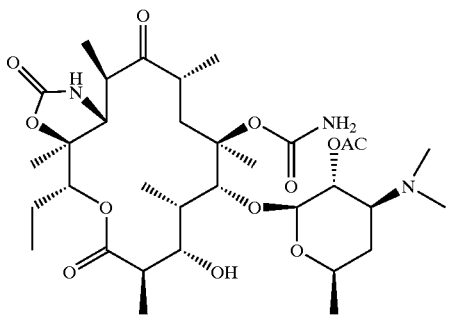

and 2-formyl-4,4-dimethoxy-butyronitrile (1.8 g, 11.46 mmol) in CH$_3$CN (15 mL) was added trifluoroacetic acid (2.56 mL, 33.2 mmol). The reaction was heated at 65° C. for 42 h before being cooled to room temperature and quenched with sat. aq. NaHCO$_3$ (15 mL). The mixture was extracted with ethyl acetate (50 mL×2). The organic layers were combined, washed with brine (15 mL) and dried over MgSO$_4$. Concentration and purification by chromatography (silica gel, 96:4:0.3 dichloromethane/methanol/conc. NH$_4$OH) gave 1.20 g (69%) of the title compound. MS 761 (M+H)$^+$.

EXAMPLE 92

Carbonic acid, (3aS,4R,7R,8S,9S,10R,11R,13R, 15R,15aR)-10-[[2-O-acetyl-3,4,6-trideoxy-3-(dimethylamino)-β-D-xylo-hexopyranosyl]oxy]-4-ethyltetradecahydro-8-hydroxy-3a,7,9,11,13,15-hexamethyl-2,6,14-trioxo-2H-oxacyclotetradecino[4,3-d]oxazol-11-yl(2E)-3-[4-(2-pyrimidinyl)phenyl]-2-propenyl ester

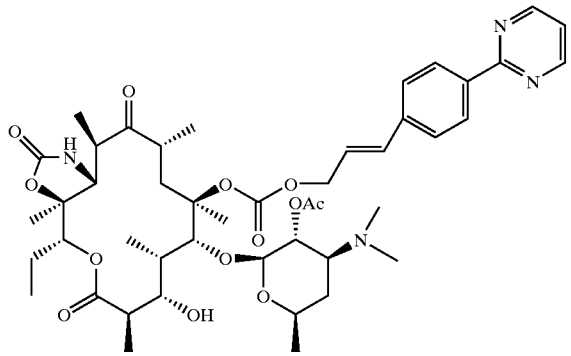

To the solution of 3-(4-pyrimidin-2-yl-phenyl)-prop-2-en-1-ol (300 mg, 1.4 mmol) (Reference Example 23) in THF (4.5 mL) and DMSO (0.5 mL) at room temperature was added 1,8-diaza-bicyclo[5,4,0]undec-7-ene (0.21 mL, 1.4 mmol). The solution was stirred at room temperature for 5 min before being cooled to 0° C. and compound of Example 91 (270 mg, 0.35 mmol) was added. The reaction was stirred at 0° C. for 2 h before being diluted with CH$_2$Cl$_2$ (75 mL). The organic solution was washed with sat. aq. NH$_4$Cl, sat. aq. NaHCO$_3$ and brine, dried over MgSO$_4$ and concentrated. Purification by chromatography (silica gel, 96:4:0.3 dichloromethane/methanol/conc. NH$_4$OH) gave 0.15 g (48%) of the title compound. MS 881 (M+H)$^+$.

EXAMPLE 93

Compound 74

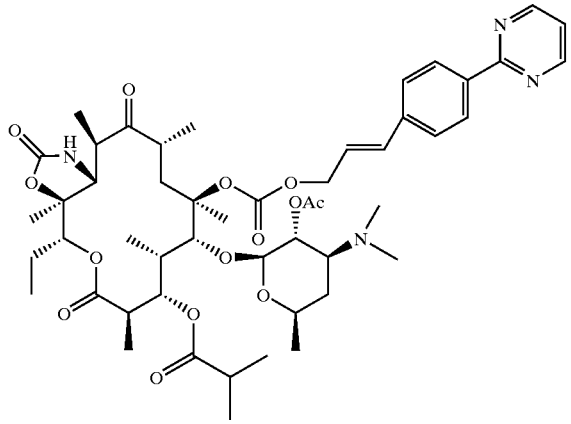

To the solution of compound of Example 92 (67 mg, 0.076 mmol) and catalytic amount of dimethylaminopyridine (DMAP) in CH$_2$Cl$_2$ (2 mL) was added triethylamine (0.36 mL, 2.59 mmol) and isobutyric anhydride (0.29 mL, 1.75 mmol). The reaction was stirred at room temperature for 7 days. MeOH (1 mL) was then added into the solution and reaction was stirred for another 5 min before being diluted with CH$_2$Cl$_2$ (50 mL). The organic solution was washed with sat. aq. NH$_4$Cl, sat. aq. NaHCO$_3$ and brine, dried over MgSO$_4$ and concentrated. The crude product was dissolved in methanol (5 mL) and stirred at room temperature for 24 h. Potassium carbonate powder (0.1 g) was then added to the solution and the reaction was stirred for another 1 h before being diluted with ethyl acetate (50 mL). The organic solution was washed with H$_2$O (5 mL) and brine (5 mL), dried over MgSO$_4$, and concentrated. Purification by chromatography (silica gel, 95:5:0.3 dichloromethane/methanol/conc. NH$_4$OH) gave 29 mg (42%) of the title compound. MS 910 (M+H)$^+$.

EXAMPLE 94

Compound 75

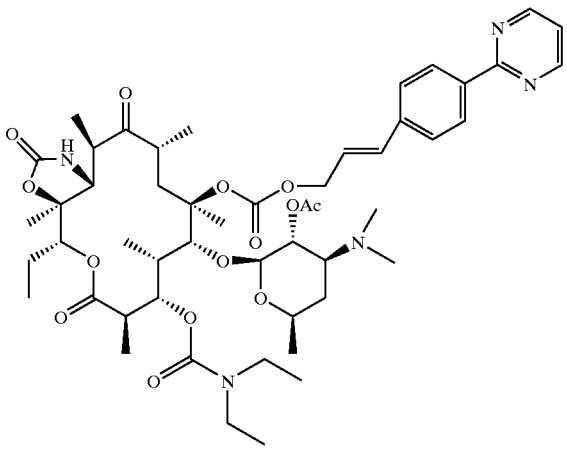

To the solution of compound of Example 92 (58 mg, 0.066 mmol) and catalytic amount of dimethylaminopyridine in CH$_2$Cl$_2$ (2 mL) at 0° C. was added pyridine (0.2 mL) and diphosgene (0.04 mL, 0.33 mmol). The reaction was warmed to room temperature and stirred for 16 h. Diethylamine (0.2 mL, 2.0 mmol) was then added to the reaction and the mixture was stirred for another 24 h before being diluted with ethyl acetate (50 mL). The organic solution was washed with sat. aq. NH$_4$Cl (5 mL×2), sat. aq. NaHCO$_3$ (5 mL) and brine, dried over MgSO$_4$, and concentrated. The crude product was dissolved in methanol (5 mL) and stirred at room temperature for 24 h. Concentration and purification by chromatography (silica gel, 96:4:0.3 dichloromethane/methanol/conc. NH$_4$OH) yielded 20 mg (32%) of the title compound. MS 939 (M+H)$^+$.

EXAMPLE 95

Compound 76

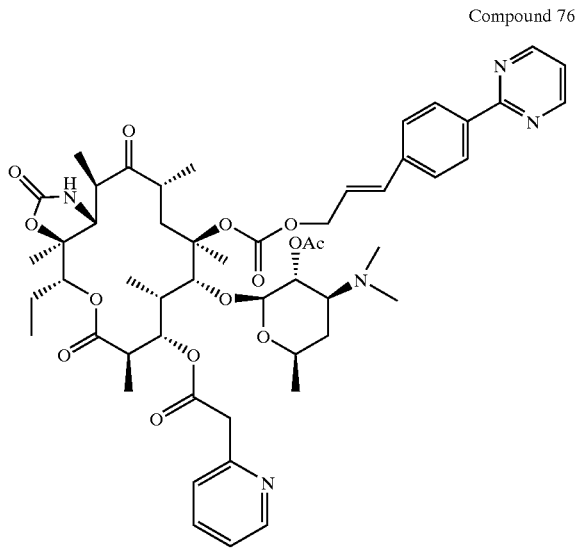

To the solution of compound of Example 92 (55 mg, 0.062 mmol), catalytic amount of dimethylaminopyridine and 2-pyridylacetic acid hydrochloride (32 mg, 0.18 mmol) in $CH_2Cl_2$ (2 mL) was added 1-[3-(dimethylamino)propyl]-3-ethylcarbodiimide hydrochloride (60 mg, 0.31 mmol). The reaction was stirred at room temperature for 16 h before being diluted with ethyl acetate (50 mL). The organic solution was washed with sat. aq. $NaHCO_3$ (5 mL), sat. aq. $NH_4Cl$ (5 mL), sat. aq. $NaHCO_3$ (5 mL) and brine (5 mL), dried over $MgSO_4$, and concentrated. The crude product was dissolved in methanol (5 mL) and stirred at room temperature for 20 h. Concentration and purification by chromatography (silica gel, 94:6:0.3 dichloromethane/methanol/conc. $NH_4OH$) yielded 49 mg (82%) of the title compound. MS 959 $(M+H)^+$.

EXAMPLE 96

3-Pyridineacetic acid, (3aS,4R,7R,8S,9S,10R,11R,13R,15R,15aR)-10-[[2-O-acetyl-3,4,6-trideoxy-3-(dimethylamino)-β-D-xylo-hexopyranosyl]oxy]-11-[[(3-cyano-1H-pyrrol-1-yl)carbonyl]oxy]4-ethyltetradecahydro-3a,7,9,11,13,15-hexamethyl-2,6,14-trioxo-2H-oxacyclotetradecino[4,3-d]oxazol-8-yl ester

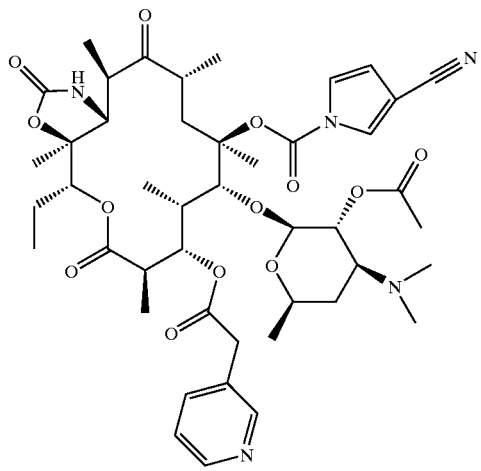

To a mixture of compound of Example 34 (0.35 g, 0.435 mmol) and 2-formyl-4,4-dimethoxy-butyronitrile (0.30 g, 1.91 mmol) in $CH_3CN$ was added trifluoroacetic acid (0.33 mL, 4.35 mmol). The mixture was heated to 60° C. for 18 hours and additional 2-formyl-4,4-dimethoxy-butyronitrile (0.15 g, 0.186 mmol) and trifluoroacetic acid (0.15 mL, 1.95 mmol) were added. The mixture is was heated to 60° C. for 18 hours before being cooled, diluted with ethyl acetate, washed with sat. aq. $NaHCO_3$, water, brine, and dried over $MgSO_4$. Concentration and chromatography (silica gel, 98:2:0.3 dichloromethane/methanol/conc. $NH_4OH$) gave 0.16 g (41%) of the title compound. MS 880 $(M+H)^+$.

EXAMPLE 97

Compound 87

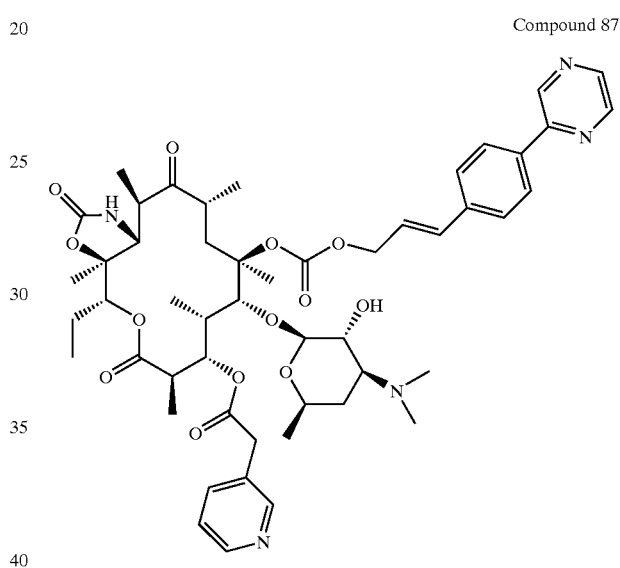

To a mixture of (2E)-3-[4-(2-pyrizinyl)phenyl]-2-propen-1-ol (0.14 g, 0.682 mmol) (Reference Example 24) in THF (1.0 mL) and DMSO (0.2 mL) was added 1,8-diazabicyclo[5.4.0]undec-7-ene (0.1 mL, 0.669 mmol). The mixture is stirred for 15 min, then cooled to 0° C. Compound of Example 96 dissolved in THF (1.5 mL) was added and the mixture was stirred at 0° C. for 2 h before being diluted with ethyl acetate, washed with sat. aq. $NH_4Cl$, sat. aq. $NaHCO_3$, brine, dried over $MgSO_4$ and concentrated. The residue was dissolved in THF (1 mL) and a mixture of (2E)-3-[4-(2-pyrizinyl)phenyl]-2-propen-1-ol (0.05 g, 0.238 mmol) and 1,8-diazabicyclo[5.4.0]undec-7-ene (0.1 mL, 0.669 mmol) dissolved in THF (1 mL). The mixture was stirred for 6 hours then was diluted with ethyl acetate, washed with sat. aq. $NH_4Cl$, sat. aq. $NaHCO_3$, brine, dried over $MgSO_4$ and concentrated. The residue is dissolved in methanol and stirred for 18 h. Concentration and chromatography (silica gel, 97:3:0.3 dichloromethane/methanol/conc. $NH_4OH$) gave 62 mg (38%) of the title compound. MS 958 $(M+H)^+$.

EXAMPLE 98

Compound 77

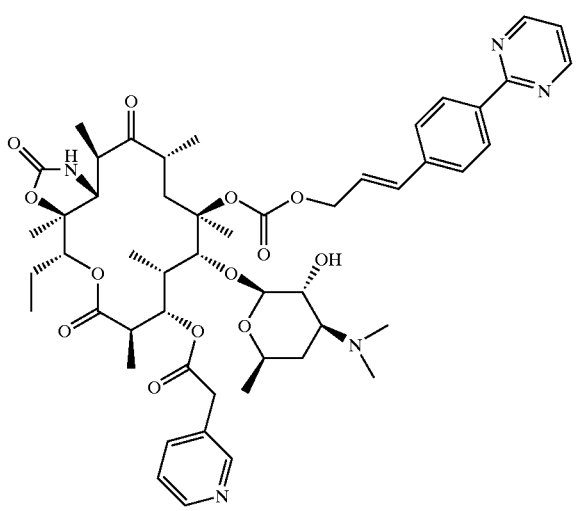

To a mixture of (2E)-3-[4-(2-pyrimadinyl)phenyl]-2-propen-1-ol (0.14 g, 0.671 mmol) (Reference Example 23) in THF (2.0 mL) and DMSO (0.1 mL) was added 1,8-diazabicyclo[5.4.0]undec-7-ene (0.052 mL, 0.341 mmol). The mixture is stirred for 15 min and compound of Example 96 (0.1 g, 0.114 mmol) was added. The mixture was stirred for 18 h before being diluted with ethyl acetate, washed with sat. aq. NH$_4$Cl, brine, dried over MgSO$_4$ and concentrated. The residue is dissolved in methanol and stirred for 20 h. Concentration and chromatography (silica gel, 97:3:0.3 dichloromethane/methanol/conc. NH$_4$OH) gave 46 mg (42%) of the title compound. MS 958 (M+H)$^+$.

EXAMPLE 99

Compound 78

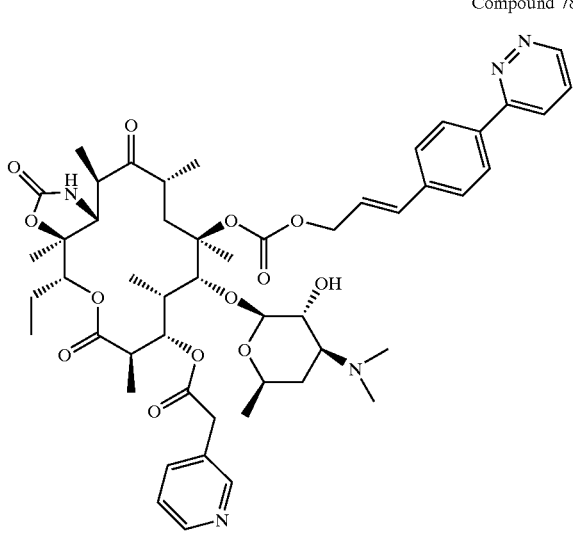

To a mixture of (2E)-3-[4-(2-pyridazinyl)phenyl]-2-propen-1-ol (0.14 g, 0.671 mmol) (Reference Example 25) in THF (3.0 mL) and DMSO (0.3 mL) was added 1,8-diazabicyclo[5.4.0]undec-7-ene (0.102 mL, 0.671 mmol). The mixture is stirred for 15 min and was added to compound of Example 96 (0.18 g, 0.224) in THF (1 mL). The mixture was stirred for 22 h before being diluted with ethyl acetate, washed with sat. aq. NH$_4$Cl, sat. aq. NaHCO$_3$, brine, dried over MgSO$_4$ and concentrated. The residue is dissolved in methanol and stirred for 20 h. Concentration and chromatography (silica gel, 97:3:0.3 dichloromethane/methanol/conc. NH$_4$OH) gave 87 mg (41%) of the title compound. MS 958 (M+H)$^+$.

EXAMPLE 100

Compound 79

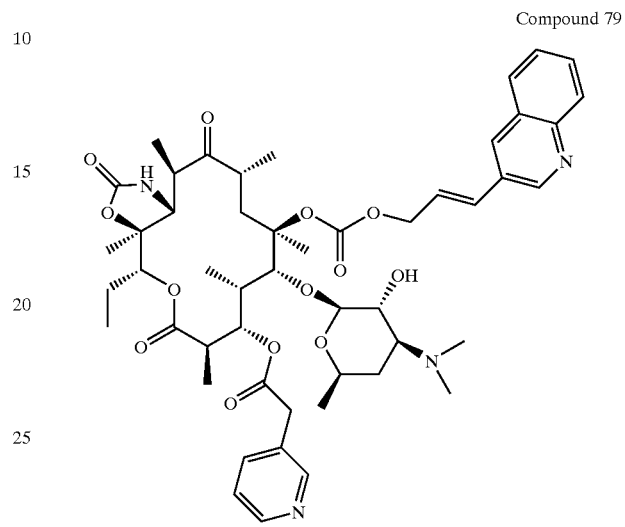

To a mixture of (2E)-3-(3-quinoline)-2-propen-1-ol (0.063 g, 0.341 mmol) (Reference Example 26) in THF (2.0 mL) and DMSO (0.1 mL) was added 1,8-diazabicyclo[5.4.0]undec-7-ene (0.051 mL, 0.341 mmol). The mixture is stirred for 15 min and compound of Example 96 (0.10 g, 0.114) was added. The mixture was stirred for 17 h before being diluted with ethyl acetate (20 mL), washed with sat. aq. NH$_4$Cl, brine, dried over MgSO$_4$ and concentrated. The residue is dissolved in methanol (5 mL) and stirred for 18 h. Concentration and chromatography (silica gel, 97:3:0.3 dichloromethane/methanol/conc. NH$_4$OH) gave 84 mg (79%) of the title compound. MS 931 (M+H)$^+$.

EXAMPLE 101

Compound 80

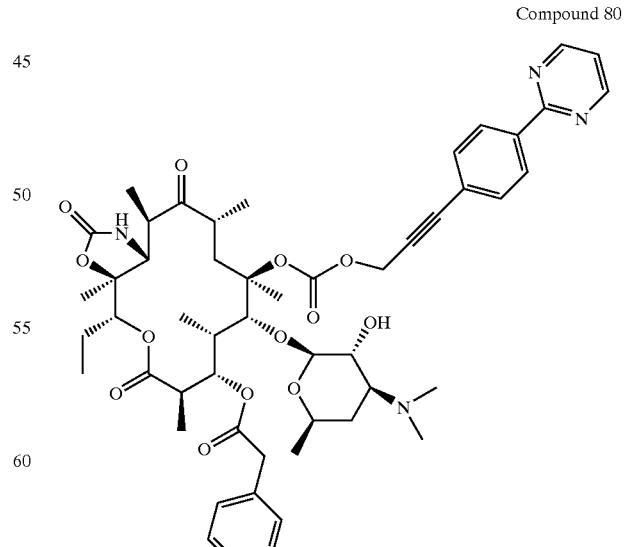

To a mixture of 3-[4-(2-pyrimadinyl)phenyl]-2-propyn-1-ol (0.0724 g, 0.341 mmol) (Reference Example 27) in THF (2.0 mL) and DMSO (0.1 mL) was added 1,8-diazabicyclo[5.4.0]undec-7-ene (0.051 mL, 0.341 mmol). The mixture is stirred for 15 min and compound of Example 96 (0.1 g, 0.114 mmol) was added. The mixture was stirred for 17 h before being diluted with ethyl acetate (20 mL), washed with sat. aq. NH$_4$Cl, brine, dried over MgSO$_4$ and concentrated. The residue is dissolved in methanol and stirred for 18 h. Concentration and chromatography (silica gel, 97:3:0.3 dichloromethane/methanol/conc. NH$_4$OH) gave 78 mg (72%) of the title compound. MS 956 (M+H)$^+$.

EXAMPLE 102

Carbonic acid, (3aS,4R,7R,8S,9S,10R,11R,13R,15R,15aR)-10-[[2-O-acetyl-3,4,6-trideoxy-3-(dimethylamino)-β-D-xylo-hexopyranosyl]oxy]4-ethyltetradecahydro-8-hydroxy-3a,7,9,11,13,15-hexamethyl-2,6,14-trioxo-2H-oxacyclotetradecino[4,3-d]oxazol-11-yl(2E)-3-[4-(3-pyridazinyl)phenyl]-2-propenyl ester

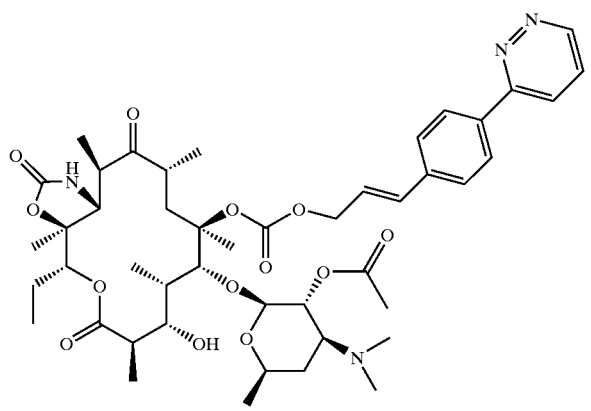

To a mixture of (2E)-3-[4-(2-pyridazinyl)phenyl]-2-propen-1-ol (0.29 g, 1.366 mmol) (Reference Example 25) in THF (10 mL) and DMSO (1 mL) was added 1,8-diazabicyclo[5.4.0]undec-7-ene (0.208 mL, 1.366 mmol). The mixture is stirred for 15 min and was added to compound of Example 91 (0.347 g, 0.455). The mixture was stirred for 5 h before being diluted with ethyl acetate, washed with sat. aq. NH$_4$Cl, sat. aq. NaHCO$_3$, brine, and dried over MgSO$_4$. Concentration and chromatography (silica gel, 97:3:0.3 dichloromethane/methanol/conc. NH$_4$OH) gave 259 mg (651%) of the title compound. MS 881 (M+H)$^+$.

EXAMPLE 103

Compound 81

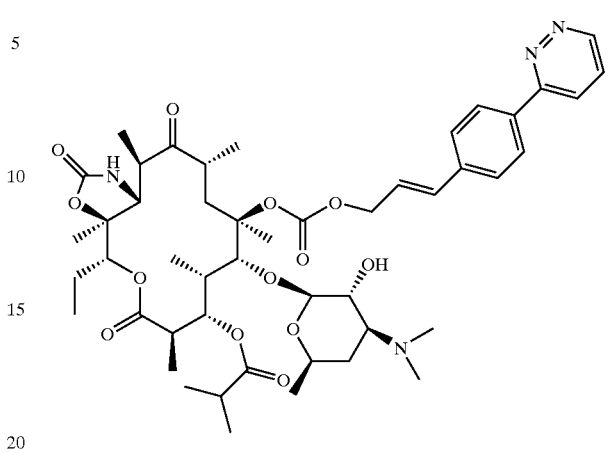

To a mixture of compound of Example 102 (0.1 g, 0.114) and a catalytic amount of 4-dimethylaminopyridine in CH$_2$Cl$_2$ (3 mL) was added triethylamine (0.126 mL, 0.908 mmol) then isobutyric anhydride (0.226 mL, 1.36). The mixture was stirred for 5 days and was diluted with ethyl acetate. The mixture was washed with sat. aq. NH$_4$Cl, sat. aq. NaHCO$_3$, brine, and dried over MgSO$_4$. The mixture was concentrated and the residue dissolved in methanol and stirred for 20 h. Concentration and purification by chromatography (silica gel, 97:3:0.3 dichloromethane/methanol/conc. NH$_4$OH) gave 54 mg (52%) of the title compound. MS 909 (M+H)$^+$.

EXAMPLE 104

Compound 82

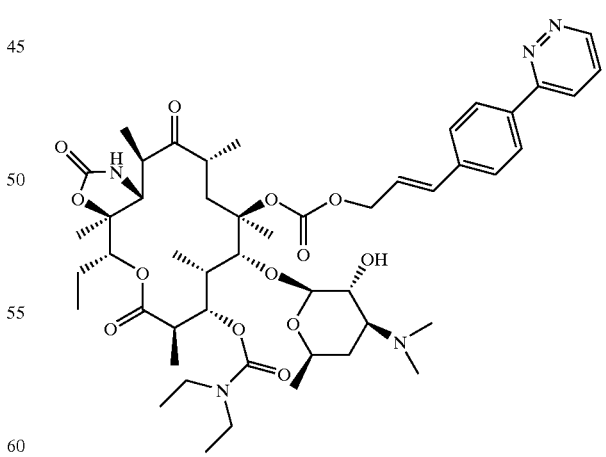

To a mixture of compound of Example 102 (0.535 g, 0.061 mmol) and a catalytic amount of 4-dimethylaminopyridine in CH$_2$Cl$_2$ (3 mL) at 0° C. was added pyridine (0.074 mL, 0.911 mmol) then diphosgene (0.060 mL, 0.304 mmol). The reaction was stirred at ambient temperature for 18 h and diethylamine (0.28 mL, 2.73 mmol) was added. The mixture was stirred for 4 h and diluted with ethyl actate. The mixture was extracted with sat. aq. NH$_4$Cl, sat. aq. NaHCO$_3$, brine, and dried over MgSO$_4$. The mixture was concentrated and dissolved in methanol (3 ml) and stirred for 18 h. Concentration and purification by chromatography (silica gel, 97:3:0.3 dichloromethane/methanol/conc. NH$_4$OH) gave 25 mg (44%) of the title compound. MS 938 (M+H)$^+$.

EXAMPLE 105

Carbonic acid, (3aS,4R,7R,8S,9S,10R,11R,13R,15R,15aR)-10-[[2-O-acetyl-3,4,6-trideoxy-3-(dimethylamino)-β-D-xylo-hexopyranosyl]oxy]4-ethyltetradecahydro-8-hydroxy-3a,7,9,11,13,15-hexamethyl-2,6,14-trioxo-2H-oxacyclotetradecino[4,3-d]oxazol-11-yl(2E)-3-(4-pyrazinylphenyl)-2-propenyl ester

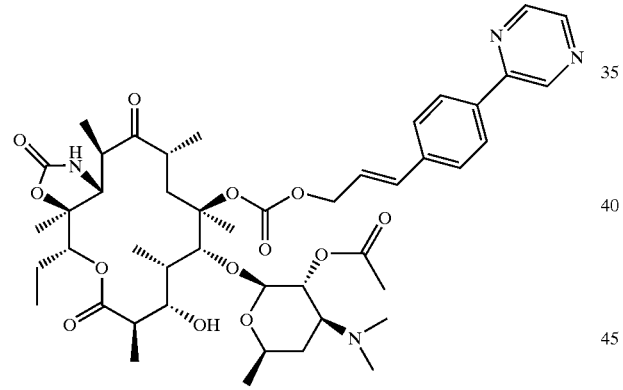

To a mixture of (2E)-3-[4-(2-pyrizinyl)phenyl]-2-propen-1-ol (0.415 g, 1.955 mmol) (Reference Example 24) in THF (12 mL) and DMSO (1.25 mL) was added 1,8-diazabicyclo[5.4.0]undec-7-ene (0.29 mL, 1.955 mmol). The mixture is stirred for 10 min then compound of Example 91 (496 mg, 0.652 mmol) was added. The mixture was stirred for 5 hours then was diluted with ethyl acetate, washed with sat. aq. NH$_4$Cl, sat. aq. NaHCO$_3$, brine, and dried over MgSO$_4$. Concentration and chromatography (silica gel, 97:3:0.3 dichloromethane/methanol/conc. NH$_4$OH) gave 268 mg (47%) of the title compound. MS 881 (M+H)$^+$.

EXAMPLE 106

Compound 83

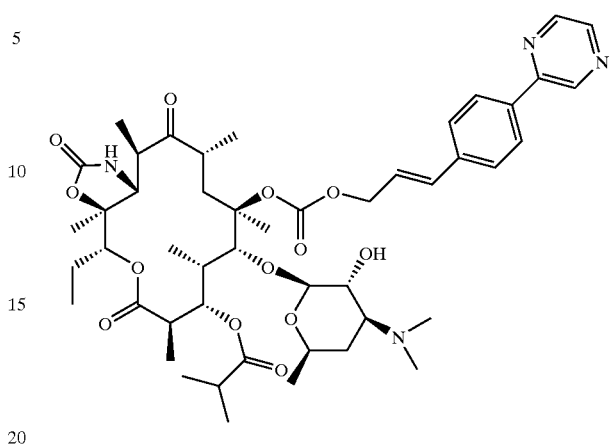

To a mixture of compound of Example 105 (0.1 g, 0.114) and a catalytic amount of 4-dimethylaminopyridine in CH$_2$Cl$_2$ (3 mL) was added triethylamine (0.126 mL, 0.908 mmol) then isobutyric anhydride (0.226 mL, 1.36). The mixture was stirred for 5 days and was diluted with ethyl acetate. The mixture was washed with sat. aq. NH$_4$Cl, sat. aq. NaHCO$_3$, brine, and dried over MgSO$_4$. The mixture was concentrated and the residue dissolved in methanol (5 mL) and stirred for 20 h. Concentration and purification by chromatography (silica gel, 97:3:0.3 dichloromethane/methanol/conc. NH$_4$OH) gave 63 mg (61%) of the title compound. MS 909 (M+H)$^+$.

EXAMPLE 107

Compound 84

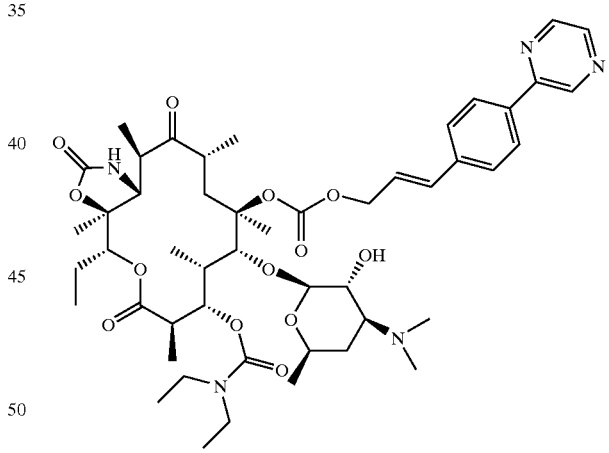

To a mixture of compound of Example 105 (0.156 g, 0.177 mmol) and a catalytic amount of 4-dimethylaminopyridine in CH$_2$Cl$_2$ (6 mL) at 0° C. was added pyridine (0.215 mL, 2.658 mmol) then diphosgene (0.107 mL, 0.886 mmol). The reaction was stirred at ambient temperature for 20 h and diethylamine (0.825 mL, 7.974 mmol) was added. The mixture was stirred for 4 h and diluted with ethyl actate. The mixture was extracted with sat. aq. NH$_4$Cl, sat. aq. NaHCO$_3$, brine, and dried over MgSO$_4$. The mixture was concentrated and dissolved in methanol and stirred for 18 h. Concentration and purification by chromatography (silica gel, 97:3:0.3 dichloromethane/methanol/conc. NH$_4$OH) gave 43 mg (26%) of the title compound. MS 938 (M+H)$^+$.

103

EXAMPLE 108

Carbonic acid, (3aS,4R,7R,8S,9S,10R,11R,13R,15R,15aR)-10-[[2-O-acetyl-3,4,6-trideoxy-3-(dimethylamino)-β-D-xylo-hexopyranosyl]oxy]-4-ethyltetradecahydro-8-hydroxy-3a,7,9,11,13,15-hexamethyl-2,6,14-trioxo-2H-oxacyclotetradecino[4,3-d]oxazol-11-yl(2E)-3-(3-quinolinyl)-2-propenyl ester

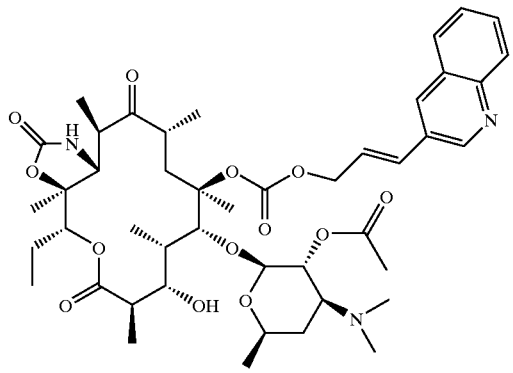

To a mixture of (2E)-3-(3-quinoline)-2-propen-1-ol (0.365 g, 1.971 mmol) (Reference Example 26) in THF (12.0 mL) and DMSO (1.25 mL) was added 1,8-diazabicyclo[5.4.0]undec-7-ene (0.3 mL, 1.971 mmol). The mixture is stirred for 10 min and compound of Example 91 (0.5 g, 0.657) was added. The mixture was stirred for 17 h before being diluted with ethyl acetate (20 mL), washed with sat. aq. NH$_4$Cl, brine, and dried over MgSO$_4$. Concentration and chromatography (silica gel, 97:3:0.3 dichloromethane/methanol/conc. NH$_4$OH) gave 320 mg (56%) of the title compound. MS 854 (M+H)$^+$.

EXAMPLE 109

Compound 85

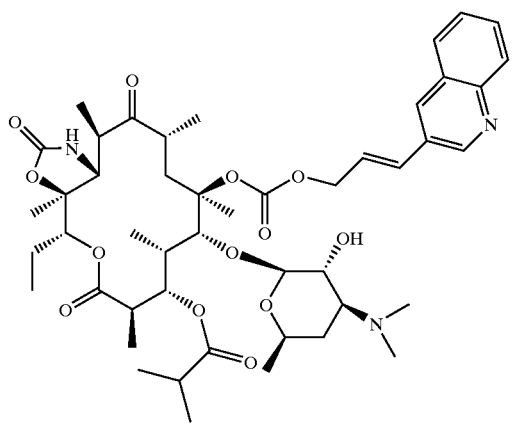

To a mixture of compound of Example 108 (0.1 g, 0.117) and a catalytic amount of 4-dimethylaminopyridine in CH$_2$Cl$_2$ (3 mL) was added triethylamine (0.131 mL, 0.938 mmol) then isobutyric anhydride (0.233 mL, 1.41). The mixture was stirred for 5 days and was diluted with ethyl acetate. The mixture was washed with sat. aq. NH$_4$Cl, sat. aq. NaHCO$_3$, brine, and dried over MgSO$_4$. The mixture was concentrated and the residue dissolved in methanol and stirred for 20 h. Concentration and purification by chromatography (silica gel, 97:3:0.3 dichloromethane/methanol/conc. NH$_4$OH) gave 69 mg (67%) of the title compound. MS 882 (M+H)$^+$.

EXAMPLE 110

Compound 86

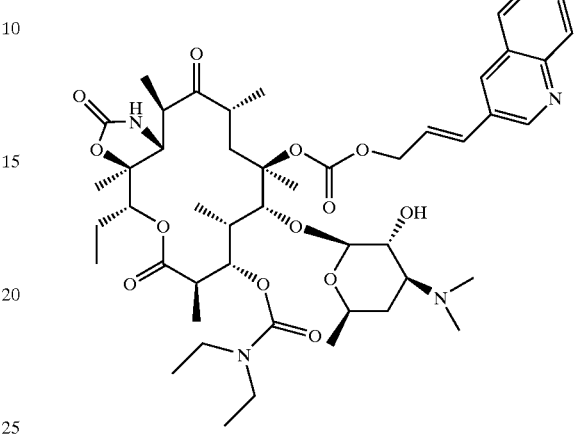

To a mixture of compound of Example 108 (0.22 g, 0.253 mmol) and a catalytic amount of 4-dimethylaminopyridine in CH$_2$Cl$_2$ (6 mL) at 0° C. was added pyridine (0.31 mL, 3.874 mmol) then diphosgene (0.155 mL, 1.29 mmol). The reaction was stirred at ambient temperature for 20 h and diethylamine (1.2 mL, 11.62 mmol) was added. The mixture was stirred for 4 h and diluted with ethyl actate. The mixture was extracted with sat. aq. NH$_4$Cl, sat. aq. NaHCO$_3$, brine, and dried over MgSO$_4$. The mixture was concentrated and dissolved in methanol and stirred for 22 h. Concentration and purification by chromatography (silica gel, 97:3:0.3 dichloromethane/methanol/conc. NH$_4$OH) gave 71 mg (30%) of the title compound. MS 911 (M+H)$^+$.

EXAMPLE 111

Compound 87

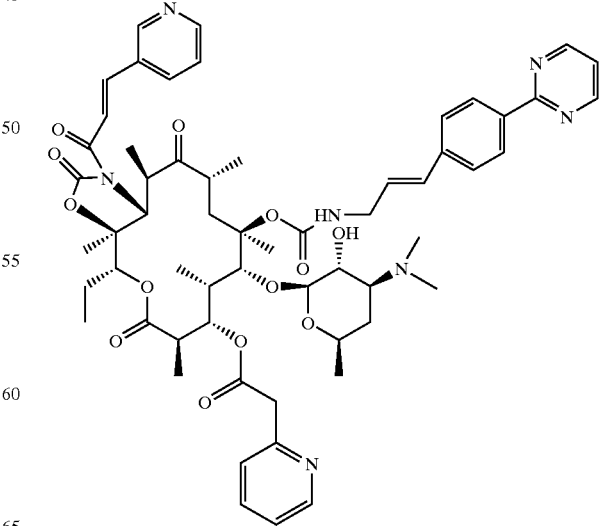

To a solution of compound of Example 1 (80 mg, 0.09 mmol), catalytic amount of dimethylaminopyridine and trans-3-(3-pyridyl)acrylic acid (60 mg, 0.40 mmol) in CH$_2$Cl$_2$ (2 mL) was added 1,3-cyclohexylcarbodiimide (125 mg, 0.61 mmol). The reaction was stirred at room temperature for 72 h before being diluted with methanol (5 mL) and stirred for 20 h. The reaction was then diluted with ethyl acetate (50 mL), washed with sat. aq. NaHCO$_3$ (10 mL) and brine (5 mL), and dried over MgSO$_4$. Concentration and purification by chromatography (silica gel, 96:4:0.3 dichloromethane/methanol/conc. NH$_4$OH to 94:6:0.3 dichloromethane/methanol/conc. NH$_4$OH) yielded 45 mg (40%) of the title compound. MS 1122 (M+Na)$^+$.

EXAMPLE 112

Compound 88

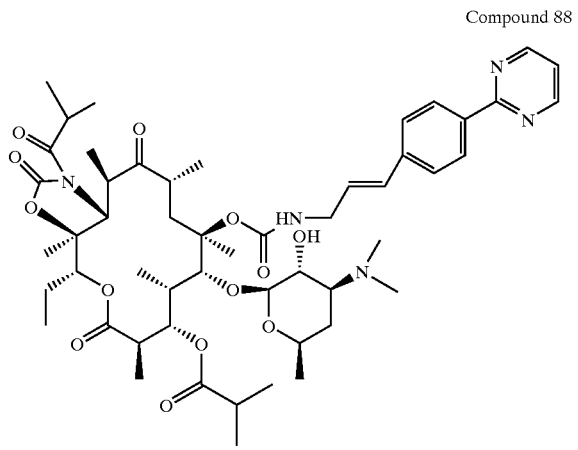

To the solution of compound of Example 1 (65 mg, 0.074 mmol) and dimethylaminopyridine (DMAP) (cat.) in CH$_2$Cl$_2$ (2 mL) was added triethylamine (0.1 mL, 0.72 mmol) and isobutyric anhydride (0.1 mL, 0.60 mmol). The reaction was stirred at room temperature for 72 h before being diluted with methanol (5 mL) and stirred at room temperature for 20 h. The reaction was then diluted with ethyl acetate (50 mL), washed with sat. aq. NaHCO$_3$ and brine, dried over MgSO$_4$, and concentrated. Purification by chromatography (silica gel, 96:4:0.3 dichloromethane/methanol/conc. NH$_4$OH) gave 38 mg (53%) of the title compound. MS 978 (M)$^+$.

EXAMPLE 113

Compound 89

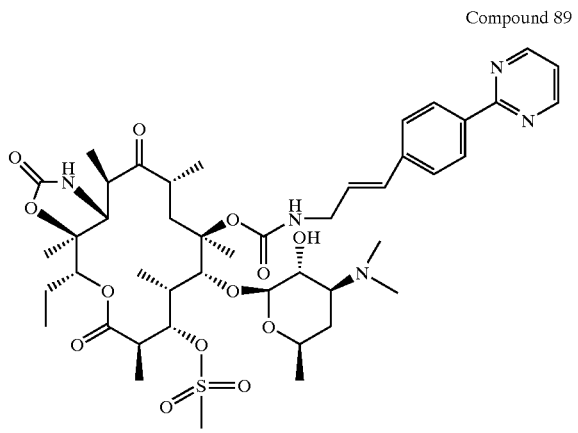

To a solution of compound of Example 1 (47 mg, 0.053 mmol) and catalytic amount of DMAP in CH$_2$Cl$_2$ (2 mL) was added triethylamine (0.1 mL, 0.72 mmol) and methanesulfonyl chloride (0.05 mL, 0.65 mmol). The reaction was stirred at room temperature for 20 h before being quenched with sat. aq. NaHCO$_3$ (10 mL). The mixture was extracted with ethyl acetate (50 mL), washed with brine (10 mL), dried over MgSO$_4$, and concentrated. The crude product was dissolved in MeOH (5 mL) and stirred at room temperature for 16 h. Concentration and purification by chromatography (silica gel, 96:4:0.3 dichloromethane/methanol/conc. NH$_4$OH) yielded 15 mg (31%) of the title compound. MS 916 (M)$^+$.

EXAMPLE 114

Compound 90

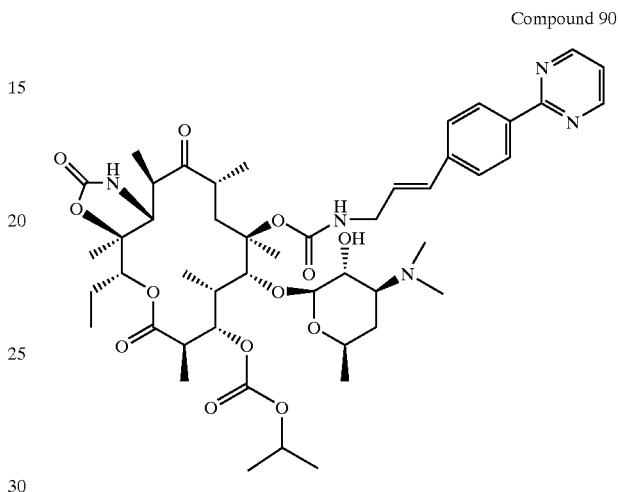

To a solution of compound of Example 1 (60 mg, 0.068 mmol) and catalytic amount of dimethylaminopyridine in CH$_2$Cl$_2$ (2 mL) and pyridine (0.3 mL) at 0° C. was added diphosgene (0.05 mL, 0.41 mmol). The reaction was warmed to room temperature and stirred for 16 h. Isopropanol (0.2 mL) was added to the reaction and the mixture was stirred for another 24 h before being diluted with ethyl acetate (50 mL). The organic solution was washed with sat. aq. NH$_4$Cl (5 mL×2), sat. aq. NaHCO$_3$ (5 mL) and brine, dried over MgSO$_4$, and concentrated. The residue was dissolved in methanol (5 mL) and stirred at room temperature for 72 h. Concentration and purification by chromatography (silica gel, 94:6:0.3 dichloromethane/methanol/conc. NH$_4$OH) yielded 23 mg (37%) of the title compound. MS 924 (M+H)$^+$.

REFERENCE EXAMPLE 1

2H-oxacyclotetradecino[4,3-d]oxazole-2,6,14(1H, 7H)-trione, 10-[[2-O-acetyl-3,4,6-trideoxy-3-(dimethylamino)-β-D-xylo-hexopyranosyl]oxy]-11-[(aminocarbonyl)oxy]-4-ethyldecahydro-8-hydroxy-3a,7,9,11,13,15-hexamethyl-, (3aS,4R,7R,8S,9S,10R,11R,13R,15R,15aR)—

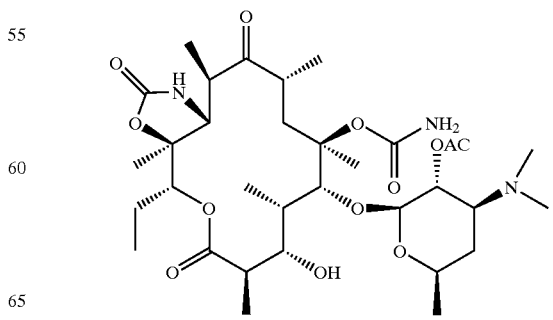

Step A

Triethylamine (42.0 mL, 301 mmol), DMAP (0.6 g, 4.9 mmol), and acetic anhydride (28.5 mL, 302 mmol) were added to a 0° C. suspension of erythromycin (36.7 g, 50 mmol) in dichloromethane (250 mL). The mixture was allowed to warm to room temperature and stir for 18 h. Methanol (10 mL) was added and stirring was continued for 5 min. The mixture was diluted with ether (750 mL), washed with sat. aq. NaHCO$_3$, water, and brine (500 mL each), dried (MgSO$_4$), and concentrated to provide the title compound as a colorless foam. The material was used in the next step without further purification. MS 860 (M+H)$^+$.

Step B

Sodium hexamethyldisilazide (1.0M in THF, 60.0 mL, 60.00 mmol) was added over 25 min to a 0° C. solution of the compound from step A (50.0 mmol) in THF (500 mL). After 2 h at 0° C., the mixture was diluted with water (250 mL) and brine (250 mL) and extracted with ethyl acetate (3×250 mL). The combined organic layers were dried (MgSO$_4$) and concentrated. The material was used in the next step without further purification. If desired, pure material could be obtained by chromatography (SiO$_2$, 95:5:0.2 dichloromethane/methanol/conc. NH$_4$OH). MS 800 (M+H)$^+$.

Step C

Trichloroacetylisocyanate (18.0 mL, 151 mmol) was added over 20 min to a 0° C. solution of the compound from step B (50 mmol) in dichloromethane (350 mL). After 3 h at 0° C., the reaction was quenched by the addition of methanol (30 mL) and concentrated. The residue was dissolved in a mixture of methanol (450 mL), water (45 mL), and triethylamine (18 mL), heated to reflux for 2 h, and concentrated. The residue was dissolved in ethyl acetate (500 mL), washed with sat. aq. NaHCO$_3$ (250 mL) and brine (250 mL), dried (MgSO$_4$), and concentrated. The resulting mixture of C-10 epimers was dissolved in THF (500 mL) at 0° C. and potassium t-butoxide (1.0 M in THF, 60.0 mL, 60.0 mmol) was added over 15 min. The resulting mixture was stirred at 0° C. to 5° C. for 6 h. Sat. aq. NaHCO$_3$ (250 mL) was added, the bulk of the THF was removed in vacuo, and the resulting solution was extracted with ethyl acetate (3×250 mL). The combined organic extracts were washed with brine (250 mL), dried (MgSO$_4$), and concentrated. The material was used in the next step without further purification. If desired, pure material could be obtained by chromatography (SiO$_2$, 95:5:0.2 dichloromethane/methanol/conc. NH$_4$OH). MS 844 (M+H)$^+$.

Step D

A solution of the compound from step C (50 mmol), triethylamine (13.0 mL, 93.3 mmol), and acetic anhydride (8.8 mL, 93.3 mmol) in dichloromethane (250 mL) was stirred at room temperature for 20 h. The solution was washed with sat. aq. NaHCO$_3$ (2×250 mL) and brine (250 mL), dried (MgSO$_4$), and concentrated. The material was used in the next step without further purification. MS 886 (M+H)$^+$.

Step E

The compound from step D (50 mmol) was dissolved in 1.2 N HCl (400 mL) and ethanol (160 mL) and stirred at room temperature for 20 h. The mixture was cooled to 0° C., made basic with 10% NaOH, and extracted with ethyl acetate (3×300 mL). The combined organic layers were washed with water (300 mL) and brine (300 mL), dried (MgSO$_4$), and concentrated. Purification by chromatography (SiO$_2$, 94:6:0.5 dichloromethane/methanol/conc. NH$_4$OH) yields 10.4 g (30% based on erythromycin) of the title compound as a colorless solid. MS 686 (M+H)$^+$.

REFERENCE EXAMPLE 2

Preparation of (2E)-3-[4-(2-pyrimidinyl)phenyl]-propenylaldehyde

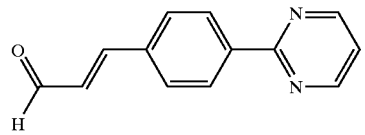

A mixture of 4-(2-pyrimidinyl)benzaldehyde (1.83 g, 9.94 mmol, prepared as described in WO 9828264), (1,3-dioxolan-2-ylmethyl)triphenylphosphonium bromide (6.45 g, 15.02 mmol), and TDA-1 (3.20 mL, 10.00 mmol) in dichloromethane (50 mL) and sat. aq. K$_2$CO$_3$ (50 mL) was heated to reflux for 20 h. The layers were separated and the aqueous layer was extracted with dichloromethane (2×25 mL). The combined organic layers were washed with water (50 mL) and brine (50 mL), dried (MgSO$_4$), and concentrated. THF (25 mL) and 10% HCl (25 mL) were added and the mixture was stirred for 1 h at rt. The mixture was cooled to 0° C., the precipitated solids were removed by filtration, washed with water and air-dried. Recrystallization from 2-propanol provided 1.20 g (57%) of the title compound as a light yellow solid. MS 211 (M+H)$^+$.

REFERENCE EXAMPLE 3

Preparation of (2E)-3-(3-pyridyl)propenylaldehyde

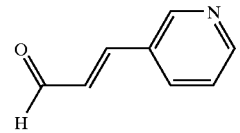

Step A:

To a solution of 3-(3-pyridyl)acrylic acid (1.0 g, 6.7 mmol) in MeOH (35 mL) at 0° C. was added SOCl$_2$ (0.15 mL, 2.05 mmol). The reaction was slowly warmed up to room temperature and stirred for 16 h. The solution was then concentrated and neutralized with sat. aq. NaHCO$_3$. The mixture was extracted with CH$_2$Cl$_2$ (100 mL), and the resulting solution was washed with sat. aq. NaCl, dried over MgSO$_4$ and concentrated.

Step B:

To the solution of the crude product from Step A (1.02 g, 6.3 mmol) in CH$_2$Cl$_2$ (50 mL) at −78° C. was added diisobutylaluminum hydride (1.0 M in CH$_2$Cl$_2$, 16 mL). The reaction was stirred at −78° C. for 10 min before being quenched with MeOH (5 mL) followed by 2.5 N aq. NaOH (50 mL). The mixture was extracted with CH$_2$Cl$_2$ (50 mL×2). The resulting solution was washed with sat. aq. NaCl, dried over MgSO$_4$ and concentrated.

Step C:

To the solution of the crude product from Step B (0.5 g, 3.8 mmol) in CH$_2$Cl$_2$ (20 mL) was added MnO2 (2.5 g). The mixture was stirred at room temperature for 16 h. Filtration, concentration and purification by chromatography (silica gel, 98:2 dichloromethane/methanol) gave 0.37 g (42%) of the title compound as white solid MS 134 (M+H)$^+$.

REFERENCE EXAMPLE 4
Preparation of trans, trans-5-(3-pyridyl)-2,4-pentadienyl aldehyde

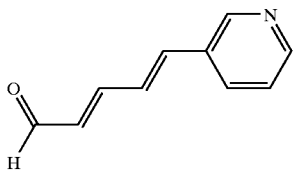

Step A:
A solution of the compound from Reference Example 3 (1.0 g, 7.5 mL) and (carbethoxymethylene)triphenylphosphorane (3.4 g, 9.8 mmol) in benzene was stirred at room temperature for 5 h. The mixture was then concentrated and purified by chromatography (silica gel, 97:3 dichloromethane/methanol).

Step B:
To a solution of the compound from Step A (7.5 mmol) in CH$_2$Cl$_2$ (50 mL) at −78° C. was added diisobutylaluminum hydride (1.0 M solution in hexane, 20 mL). The reaction was stirred at −78° C. for 30 min before being quenched with MeOH (5 mL) followed by 2.5 N aq. NaOH (70 mL). The mixture was extracted with CH$_2$Cl$_2$ (100 mL×2), and the resulting solution was washed with sat. aq. NaCl, dried over MgSO$_4$ and concentrated. Purification by chromatography (silica gel, 96:4 dichloromethane/methanol) gave 0.67 g (55%) of the desired compound as off-white solid.

Step C:
A solution of the compound from Step B (0.67 g, 4.2 mmol) and MnO$_2$ (6.0 g) in CH$_2$Cl$_2$ (40 mL) was stirred at room temperature for 16 h. Filtration, concentration and purification by chromatography (silica gel, 97:3 dichloromethane/methanol) gave 0.55 g (83%) of the title compound as off-white solid MS160 (M+H)$^+$.

REFERENCE EXAMPLE 5
Preparation of trans, trans-5-(2-pyridyl)-2,4-pentadienyl aldehyde

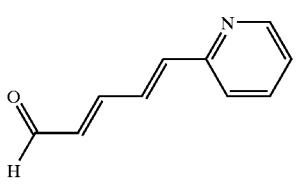

Step A:
To a solution of triethyl 4-phosphonocrotonate (3.5 mL, 15.8 mmol) in THF (100 mL) at 0° C. was added NaHMDS (1.0 M solution in THF, 14.7 mL). The solution was stirred at 0° C. for 20 min before 2-pyridinecarboxaldehyde (1.0 mL, 10.5 mmol) was added. The reaction was kept at 0° C. for 1.5 h before being quenched with H$_2$O. The mixture was extracted with EtOAc (100 mL), and the resulting solution was washed with sat. aq. NaCl, dried over MgSO$_4$ and concentrated. Purification by chromatography (silica gel, 98.5:1.5 dichloromethane/methanol) gave 1.7 g (79%) of the desired compound as yellow oil.

Step B:
To a solution of the compound from Step A (1.7 g, 8.4 mmol) in CH$_2$Cl$_2$ (100 mL) at −78° C. was added diisobutylaluminum hydride (1.0 M solution in hexane, 25 mL). The reaction was stirred at −78° C. for 25 min before being quenched with MeOH (5 mL) followed by 2.5 N aq. NaOH (50 mL). The mixture was extracted with CH$_2$Cl$_2$ (100 mL×2), and the resulting solution was washed (silica gel, 96:4 dichloromethane/methanol) gave 1.3 g (96%) of the desired compound as yellow oil.

Step C:
A solution of the compound from Step B (1.3 g g, 8.1 mmol) and MnO$_2$ (8.0 g) in CH$_2$Cl$_2$ (80 mL) was stirred at room temperature for 16 h. Filtration, concentration and purification by chromatography (silica gel, 98.5:1.5 dichloromethane/methanol) gave 0.9 g (70%) of the title compound as yellow solid MS160 (M+H)$^+$.

REFERENCE EXAMPLE 6
Preparation of trans-3-[5-(2-bromopyridyl)]propenyl aldehyde

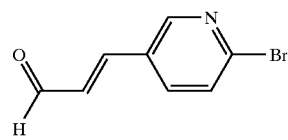

2-Propylmagnesium chloride (2.0 M in THF, 5.00 mL 10.00 mmol) was added to a solution of 2,5-dibromopyridine (2.37 g, 10.00 mmol) in THF (5.0 mL) at RT. The resulting brown suspension was stirred for 1 h and then cooled to 0° C. 3-Dimethylaminoacrolein (95%, 1.30 mL, 12.36 mmol) was added and the mixture was warmed to RT and stirred for 2 h. 2 N HCl was added and after 5 min the mixture was cooled to 0° C. The precipitated solids were removed by filtration and partitioned between ethyl acetate (75 mL) and 10% NaOH (25 mL). The ethyl acetate layer was washed with brine (25 mL), dried (MgSO$_4$), and concentrated. Recrystallization from ethyl acetate provided 550 mg (26%) of the title compound as shiny brown flakes MS 212 (M+H)$^+$.

REFERENCE EXAMPLE 7
Preparation of trans-3-(3-quinoline)propenyl aldehyde

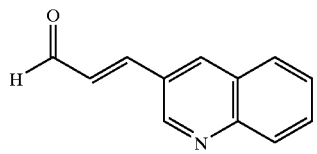

A mixture of 3-quinolinecarboxaldehyde (2.8 g g, 17.8 mmol), (1,3-dioxolan-2-ylmethyl)triphenylphosphonium bromide (11.5 g, 26.8 mmol), and TDA-1 (5.7 mL, 17.8 mmol) in dichloromethane (90 mL) and sat. aq. K$_2$CO$_3$ (90 mL) was heated to reflux for 6 h. The layers were separated and the aqueous layer was extracted with dichloromethane (2×50 mL). The combined organic layers were washed with water (50 mL) and brine (50 mL), dried (MgSO$_4$), and concentrated. THF (50 mL) and 10% HCl (50 mL) were added and the mixture was stirred for 2 h at rt. The reaction mixture was cooled to 0° C., made basic with 10% NaOH, and extracted with ethyl CH$_2$Cl$_2$ (2×50 mL). The combined organic layers were washed with water (50 mL) and brine (50 mL), dried (MgSO$_4$), and concentrated. Purification by chromatography (silica gel, 98.5:1.5 dichloromethane/methanol) gave 2.6 g (80%) of the title compound as yellow solid MS 184 (M+H)$^+$.

REFERENCE EXAMPLE 8

Preparation of trans-3-(4-quinoline)propenyl aldehyde

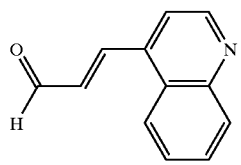

The title compound was prepared by a procedure analogous to Reference Example 7 by substituting 4-quinolinecarboxaldehyde for the 3-quinolinecarboxaldehyde of Reference Example 7 MS 184 (M+H)$^+$.

REFERENCE EXAMPLE 9

Preparation of trans, trans-5-quinolin-3-yl-penta-2,4-dienal

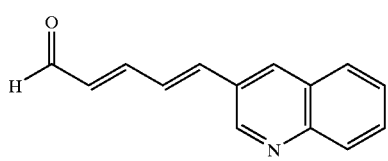

The title compound was prepared by a procedure analogous to Reference Example 5 by substituting 3-quinolinecarboxaldehyde for the 2-pyridinecarboxaldehyde of Reference Example 5. MS 210 (M+H)$^+$.

REFERENCE EXAMPLE 10

Preparation of 3-(6-trifluoromethyl-pyridin-3-yl)-propenal

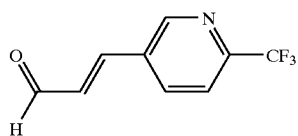

The title compound was prepared by a procedure analogous to Reference Example 7 by substituting 6-trifluoromethyl-3-pyridinecarboxaldehyde for the 3-quinolinecarboxaldehyde of Reference Example 7. MS 202 (M+H)$^+$.

REFERENCE EXAMPLE 11

Preparation of 5-pyrazin-2-yl-penta-2,4-dienal

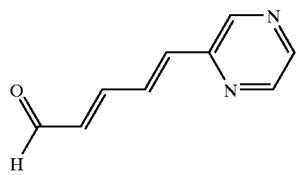

The title compound was prepared by a procedure analogous to Reference Example 5 by substituting 2-pyrazinecarboxaldehyde for the 2-pyridinecarboxaldehyde of Reference Example 5. MS 161 (M+H)$^+$.

REFERENCE EXAMPLE 12

Preparation of 3-(2-trifluoromethyl-pyrimidin-5-yl)-propenal

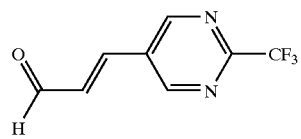

The title compound was prepared by a procedure analogous to Reference Example 7 by substituting 2-trifluoromethyl-5-pyrimidinecarboxaldehyde (prepared as described in WO0066566) for the 3-quinolinecarboxaldehyde of Reference Example 7. MS 203 (M+H)$^+$.

REFERENCE EXAMPLE 13

Preparation of 3-(2-cyclopropyl-pyrimidin-5-yl)-propenal

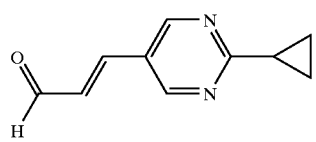

Step A:

To a solution of ethyl 3-(2-cyclopropylpyrimidin-5-yl) acrylate (prepared as described in WO0066566) (0.77 g, 3.5 mmol) in CH$_2$Cl$_2$ (35 mL) at −78° C. was added diisobutylaluminum hydride (1.0 M solution in hexane, 9 mL). The reaction was stirred at −78° C. for 30 min before being quenched with MeOH (5 mL) followed by 2.5 N aq. NaOH (20 mL). The mixture was extracted with CH$_2$Cl$_2$ (50 mL×4), and the resulting organic solution was washed with sat. aq. NaCl, dried over MgSO$_4$ and concentrated.

Step B:

A solution of crude product from Step A and MnO$_2$ (2 g) in CH$_2$Cl$_2$ (20 mL) was stirred at room temperature for 16 h. Filtration, concentration and purification by chromatography (silica gel, 98:2 dichloromethane/methanol) gave 0.32 g (52%) of the title compound as yellow solid MS 175 (M+H)$^+$.

REFERENCE EXAMPLE 14

Preparation of 3-(pyrimidin-5-yl)-propenal

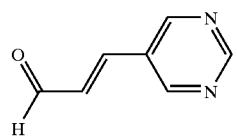

The title compound was prepared by a procedure analogous to Reference Example 13 by substituting ethyl 3-(5-pyridiminyl)acrylate (prepared as described in WO0066566) for the ethyl 3-(2-cyclopropylpyrimidin-5-yl)acrylate of Reference Example 13. MS 135 (M+H)$^+$.

REFERENCE EXAMPLE 15
Preparation of 3-(2-isopropyl-pyrimidin-5-yl)-propenal

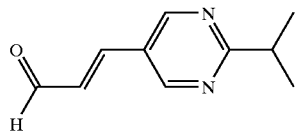

The title compound was prepared by a procedure analogous to Reference Example 13 by substituting ethyl 3-(2-isopropyl-pyridimin-5-yl)acrylate (prepared as described in WO0066566) for the ethyl 3-(2-cyclopropylpyrimidin-5-yl)acrylate of Reference Example 13. MS 177 (M+H)$^+$.

REFERENCE EXAMPLE 16
Preparation of 3-(2-tert-butyl-pyrimidin-5-yl)-propenal

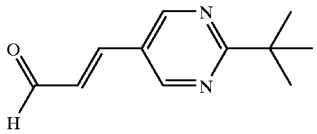

The title compound was prepared by a procedure analogous to Reference Example 13 by substituting ethyl 3-(2-tert-butyl-pyridimin-5-yl)acrylate (prepared as described in WO0066566) for the ethyl 3-(2-cyclopropylpyrimidin-5-yl)acrylate of Reference Example 13. MS 191 (M+H)$^+$.

REFERENCE EXAMPLE 17
Preparation of 5-(2-isopropyl-pyrimidin-5-yl)-penta-2,4-dienal

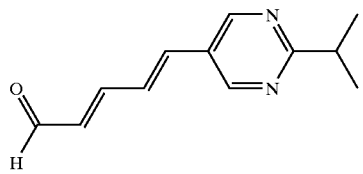

The title compound was prepared by a procedure analogous to Reference Example 5 by substituting 3-(2-isopropyl-pyrimidin-5-yl)-propenal (Reference Example 15) for the 2-pyridinecarboxaldehyde of Reference Example 5. MS 203 (M+H)$^+$.

REFERENCE EXAMPLE 18
Preparation of (2E)-3-[4-(2-pyrazinyl)phenyl]propenylaldehyde

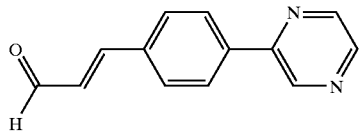

Step A:
1 M aq. Na$_2$CO$_3$ (20 mL) and ethanol (10 mL) were added to a solution 15 of 2-chloropyrazine (2.30 g, 20.06 mmol), 4-formylphenylboronic acid (3.90 g, 26.01 mmol) and [1,4-bis(diphenylphosphino)butane]palladium(II) dichloride (0.60 g, 0.99 mmol) in toluene (40 mL) and the mixture was heated to reflux for 18 h. The cooled reaction mixture was diluted with ethyl acetate, washed with sat. aq. NaHCO$_3$ and brine, dried (MgSO$_4$), and concentrated. Purification by chromatography (SiO$_2$, 4:1 hexane/ethyl acetate) yielded 1.56 g (42%) of 4-pyrazinylbenzaldehyde.

Step B:
The title compound was prepared by a procedure analogous to Reference Example 2 by substituting 4-pyrazinylbenzaldehyde for the 4-(2-pyrimidinyl)-benzaldehyde of Reference Example 2. MS 211 (M+H)$^+$.

REFERENCE EXAMPLE 19
Preparation of (2E)-3-[4-(6-pyridazinyl)phenyl]propenylaldehyde

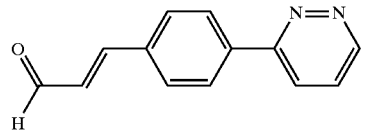

The title compound was prepared by a procedure analogous to Reference Example 18 by substituting 3-chloropyridazine (prepared as described in WO 9724124) for the 2-chloropyrazine of Reference Example 18. MS 211 (M+H)$^+$.

REFERENCE EXAMPLE 20
Preparation of (2E)-3-[4-(2-(1,2,4-triazole))phenyl]propenylaldehyde

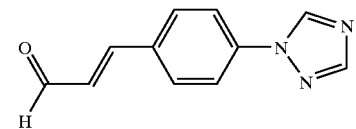

The title compound was prepared by a procedure analogous to Reference Example 2 by substituting 4-(1H-1,2,4-triazol-1-yl)benzaldehyde (prepared as described in *J. Med Chem.* 1998, 41, 2390) for the 4-(2-pyrimidinyl)-benzaldehyde of Reference Example 2. MS 200 (M+H)$^+$.

REFERENCE EXAMPLE 21
Preparation of (2E)-3-[4-(1H-pyrazole)phenyl]propenylaldehyde

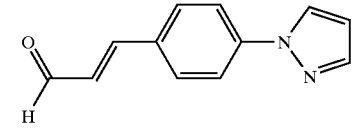

A mixture of 4-(1H-pyrazol-1-yl)benzaldehyde (prepared as described in *J. Med Chem.* 1998, 41, 2390) (1.65 g, 9.58 mmol), (1,3-dioxolan-2-ylmethyl)triphenylphosphonium bromide (6.45 g, 15.02 mmol), and TOA-1 (3.20 mL, 10.00 mmol) in dichloromethane (50 mL) and sat. aq. K$_2$CO$_3$ (50 mL) was heated to reflux for 20 h. The layers were separated and the aqueous layer was extracted with dichloromethane (2×25 mL). The combined organic layers were washed with water (50 mL) and brine (50 mL), dried (MgSO$_4$), and concentrated. THF (25 mL) and 10% HCl (25 mL) were added and the mixture was stirred for 1 h at rt. The reaction mixture was cooled to 0° C., made basic with 10% NaOH, and extracted with ethyl acetate (3×25 mL). The combined organic layers were washed with water (50 mL) and brine (50 mL), dried (MgSO$_4$), and concentrated. Purification by chromatography (SiO$_2$, 3:1 hexane/ethyl acetate) provided 1.69 g (89%) of the title compound as a yellow solid. MS 199 (M+H)$^+$.

REFERENCE EXAMPLE 22

Preparation of (2E)-3-{4-[3-(1H-methylpyrazole)]phenyl}-propenylaldehyde

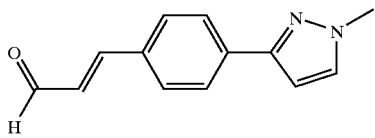

The title compound was prepared by a procedure analogous to Reference Example 2 by substituting 4-(1-methyl-1H-pyrazol-3-yl)benzaldehyde (prepared as described in *J. Med. Chem.* 1998, 41, 2390) for the 4-(2-pyrimidinyl)-benzaldehyde of Reference Example 2. MS 213 (M+H)$^+$.

REFERENCE EXAMPLE 23

Preparation of 3-(4-pyrimidin-2-yl-phenyl)prop-2-en-1-ol

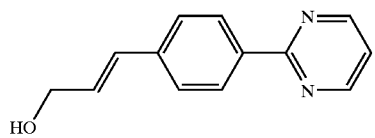

DIBAL (1.0 M in THF, 18.0 mL) was added over 10 min to a −78° C. suspension of (2E)-3-[4-(2-pyrimidinyl)phenyl]-2-propenal (2.50 g, 11.89 mmol, prepared as described in Reference Example 2) in dichloromethane (100 mL). The resulting suspension was stirred for 30 min at −78° C., methanol (2 mL) was added cautiously, and stirring was continued for 5 min at −78° C. The mixture was poured into a mixture of 10% aq. citric acid (300 mL) and dichloromethane (200 mL) and allowed to stir for 1 h. The organic layer was separated, washed with sat. aq. NaHCO$_3$ (200 mL) and brine (200 mL), dried (MgSO$_4$), filtered through Celite, and concentrated. The resulting material was triturated with ether and dried in vacuo to provide 2.08 g (82%) of the title compound. MS 213 (M+H)$^+$.

REFERENCE EXAMPLE 24

Preparation of 3-(4-(2-pyrazinyl)phenyl)prop-2-en-1-ol

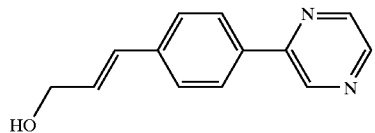

Sodium borohydride (90 mg, 2.38 mmol) was added to a suspension of (2E)-3-[4-(3-pyrazinyl)phenyl]-2-propenal (400 mg, 1.90 mmol, prepared as described in Reference Example 18) in ethanol (5 mL) maintained in a room temperature water bath. After 20 min, the reaction was quenched with water (10 mL), allowed to stir for 10 min, and then concentrated to remove the ethanol. The solids were removed by filtration, washed with water, and dried in vacuo to provide 360 mg (89%) of the title compound. MS 213 (M+H)$^+$.

REFERENCE EXAMPLE 25

Preparation of 3-(4-(2-pyridazinyl)phenyl)prop-2-en-1-ol

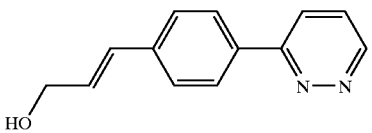

The title compound was prepared by a procedure analogous to Reference Example 24 by substituting 3-(4-(2-pyridazinyl)phenyl)propenyl aldehyde (prepared as described in Reference Example 19) for the 3-(4-(2-pyrazinyl)phenyl)propenyl aldehyde of Reference Example 24. MS 213 (M+H)$^+$.

REFERENCE EXAMPLE 26

Preparation of (2E)-3-(3-quinoline)-2-propen-1-ol

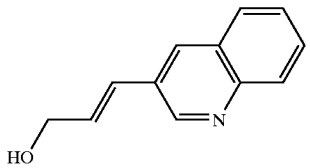

The title compound was prepared by a procedure analogous to Reference Example 24 by substituting trans-3-(3-quinoline)propenyl aldehyde (prepared as described in Reference Example 7) for the 3-(4-(2-pyrazinyl)phenyl)propenyl aldehyde of Reference Example 24. MS 186 (M+H)$^+$.

REFERENCE EXAMPLE 27

Preparation of 3-[4-(2-pyrimidinyl)phenyl]2-propyn-1-ol

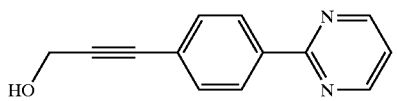

Step A:

A solution of 4-iodophenylboronic acid (19.8 g, 80.0 mmol) and Pd(PPh$_3$)$_4$ (0.93 mg, 0.80 mmol) in pyrrolidine (100 mL) was stirred at room temperature for 5 min. The resulting solution was cooled to 0° C., and propargyl alcohol (9.4 mL, 161.5 mmol) was then added. The reaction was stirred at 0° C. for 1 h before being warmed up to room temperature and stirred for 18 h. The mixture was concentrated and the residue was dissolved in 2 N NaOH (200 mL). The aqueous solution was washed with CH$_2$Cl$_2$ (100 mL×2) before being cooled to 0° C. and acidified with 10% aq. HCl. The resulting mixture was filtrated and the solid was washed with H$_2$O and dried in vacuo.

Step B:

A solution of 2-bromopyrimidine (1.0 g, 6.29 mmol) and Pd(PPh$_3$)$_4$ (0.22 g, 0.19 mmol) in DME (28 mL) was stirred in at room temperature for 10 min before a slurry of NaHCO$_3$ (1.58 g, 18.81 mmol) and the compound from Step A (1.32 g, 7.5 mmol) in H$_2$O (25 mL) was added. The reaction was heated to reflux for 4 h. The mixture was then cooled to room temperature and diluted with CH$_2$Cl$_2$ (100 mL) and H$_2$O (100 mL). The aqueous layer was extracted with CH$_2$Cl$_2$ (25 mL). The organic layers were combined, dried over MgSO$_4$ and concentrated. Purification by chromatography (SiO$_2$, 3:2 hexane/ethyl acetate) provided 1.04 (7%) of the title compound as a pale yellow solid MS 211 (M+H)$^+$.

What is claimed is:
1. A compound of Formula 1

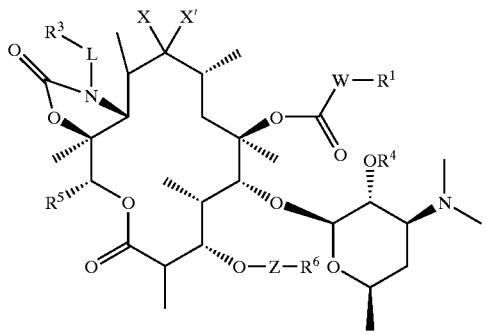

Formula 1 wherein
- $R^1$ is selected from hydrogen, optionally substituted $C_1$–$C_8$-alkyl, optionally substituted $C_2$–$C_8$-alkenyl, and optionally substituted $C_2$–$C_8$-alkynyl, wherein the substituents are independently selected from halogen, alkyl, alkenyl, alkynyl, cycloalkyl, oxo, aryl, heteroaryl, heterocyclo, CN, nitro, —$COOR_a$, —$OCOR_a$, —$OR_a$, —$SR_a$, —$SOR_a$, —$SO_2R_a$, —$NR_aR_b$, —$CONR_aR_b$, —$OCONR_aR_b$, —$NHCOR_a$, —$NHCOOR_a$, and —$NHCONR_aR_b$, wherein $R_a$ and $R_b$ are independently selected from hydrogen, alkyl, alkenyl, alkynyl, cycloalkyl, aryl, heteroaryl, heterocyclo, aralkyl, heteroaralkyl, and heterocycloalkyl;
- $R^2$ is selected from hydrogen, alkoxy, optionally substituted $C_1$–$C_8$-alkyl, optionally substituted $C_2$–$C_8$-alkenyl, and optionally substituted $C_2$–$C_8$-alkynyl, wherein the substituents are independently selected from halogen, alkyl, alkenyl, alkynyl, cycloalkyl, oxo, aryl, heteroaryl, heterocyclo, CN, nitro, —$COOR_a$, —$OCOR_a$, —$OR_a$, —$SR_a$, —$SOR_a$, —$SO_2R_a$, —$NR_aR_b$, —$CONR_aR_b$, —$OCONR_aR_b$, —$NHCOR_a$, —$NHCOOR_a$, and —$NHCONR_aR_b$, wherein $R_a$ and $R_b$ are independently selected from hydrogen, alkyl, alkenyl, alkynyl, cycloalkyl, aryl, heteroaryl, heterocyclo, aralkyl, heteroaralkyl, and heterocycloalkyl;
- $R^3$ is selected from hydrogen, optionally substituted alkyl, optionally substituted alkenyl, optionally substituted alkynyl, cycloalkyl, optionally substituted aryl, and optionally substituted heteroaryl;
- $R^4$ is hydrogen or a hydroxy protecting group;
- $R^5$ is selected from hydrogen, $C_1$–$C_8$-alkyl, $C_2$–$C_{10}$-alkenyl, $C_2$–$C_{10}$-alkynyl, aryl, heteroaryl, heterocyclo, aryl($C_1$–$C_{10}$)alkyl, aryl($C_2$–$C_{10}$)alkenyl, aryl($C_2$–$C_{10}$)alkynyl, heterocyclo($C_1$–$C_{10}$)alkyl, heterocyclo($C_2$–$C_{10}$)alkenyl, and heterocyclo($C_2$–$C_{10}$)alkynyl, $C_3$–$C_6$-cycloalkyl, $C_5$–$C_8$-cycloalkenyl, alkoxyalkyl containing 1–6 carbon atoms in each alkyl or alkoxy group, and alkylthioalkyl containing 1–6 carbon atoms in each alkyl or thioalkyl group;
- L is absent or C(O);
- W is O;
- X and X', together with the carbon atom to which they are attached, form C=O, C=$NR_c$, or C=$NOR_c$, wherein $R_c$ is independently selected from hydrogen, alkyl, alkenyl and alkynyl; and
- Z is selected from C(O), C(O)—O, C(O)—$NR^2$, and $SO_2$; and
- $R^6$ is selected from optionally substituted aryl, optionally substituted heteroaryl, optionally substituted heterocyclyl, optionally substituted cycloalkyl, optionally substituted $C_1$–$C_8$-alkyl, optionally substituted $C_2$–$C_8$-alkenyl, and optionally substituted $C_2$–$C_8$-alkynyl, wherein the substituents are selected from halogen, alkyl, alkenyl, alkynyl, cycloalkyl, oxo, alkoxyimino, aryl, heteroaryl, heterocyclo, CN, nitro, —$COOR_a$, —$OCOR_a$, —$OR_a$, —$SR_a$, $SOR_a$, —$SO_2R_a$, —$NR_aR_b$, —$CONR_aR_b$, —$OCONR_aR_b$, —$NHCOR_a$, —$NHCOOR_a$, and —$NHCONR_aR_b$, wherein $R_a$ and $R_b$ are independently selected from hydrogen, alkyl, alkenyl, alkynyl, cycloalkyl, aryl, heteroaryl, heterocyclo, aralkyl, heteroaralkyl, and heterocycloalkyl, or $NR^2R^6$ taken together form heterocyclyl having at least one N atom;

or an optical isomer, enantiomer, diastereomer, racemate or racemic mixture thereof, or a pharmaceutically acceptable salt, esters or pro-drugs thereof.

2. The compound of claim 1 wherein L is absent and $R^3$ is hydrogen.

3. The compound of claim 1 wherein $R^4$ is hydrogen and $R^5$ is $C_1$–$C_8$-alkyl.

4. The compound of claim 1 wherein $R^1$ is substituted $C_2$–$C_8$-alkenyl.

5. The compound of claim 4 wherein the $C_2$–$C_8$-alkenyl is substituted with aryl.

6. The compound of claim 5 wherein the aryl is substituted with heteroaryl.

7. The compound of claim 6 wherein the heteroaryl is selected from

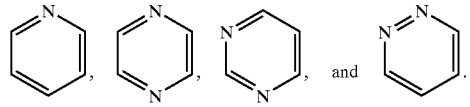

8. The compound of claim 4 wherein the $C_2$–$C_8$ alkenyl is substituted with heteroaryl.

9. The compound of claim 8 wherein the heteroaryl is

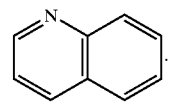

10. The compound of claim 1 wherein Z is C(O) or C(O)—$NR^2$, $R^2$ and $R^6$ are independently $C_1$–$C_8$-alkyl optionally substituted with heteroaryl.

11. The compound of claim 8 wherein the heteroaryl is

12. The compound of claim 4 wherein the $C_2$–$C_8$-alkenyl is propenyl.

13. The compound of claim 4 wherein the $C_2$–$C_8$-alkenyl is substituted with alkenyl.

14. A pharmaceutical composition comprising a compound of claim 1 and a pharmaceutically acceptable carrier.

15. A method of treating a subject having a condition caused by or contributed to by bacterial infection, which comprises administering to the subject a therapeutically effective amount of the compound of Formula 1 as defined in claim 1.

16. The method of claim 15 wherein the condition is selected from community-acquired pneumonia, upper and lower respiratory tract infections, skin and soft tissue infections, meningitis, hospital-acquired lung infections, and bone and joint infections.

17. The method of claim 15 wherein the bacterium is selected from *S. aureus, S. epidermidis, S. pneumoniae, Enterococcus* spp., *Moraxella catarrhalis* and *H. influenzae*.

18. The method of claim 15 wherein the bacterium is a Gram-positive coccus.

19. The method of claim 18 wherein the Gram-positive coccus is antibiotic-resistant.

20. The method of claim 19 wherein the Gram-positive coccus is erythromycin-resistant.

21. The method of claim 15 wherein the bacterium is a Gram-positive or Gram-negative respiratory pathogen.

22. A compound of the formula:

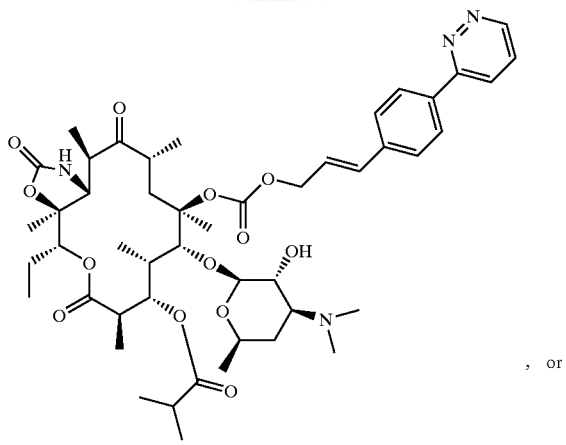

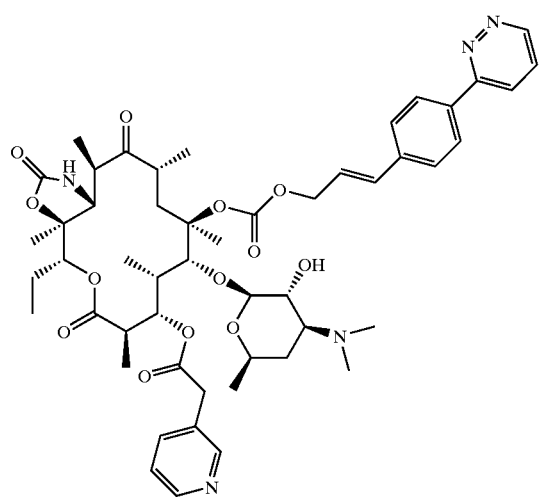

, or

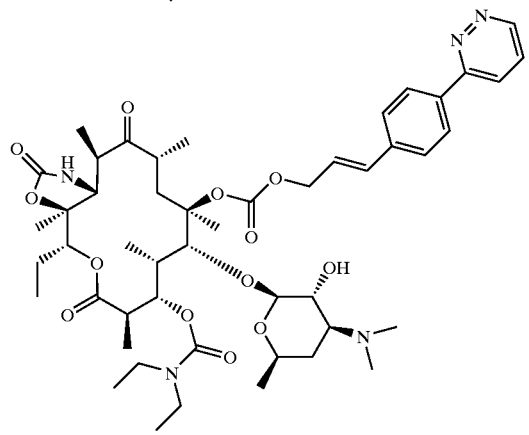

* * * * *